(12) United States Patent
Clarke et al.

(10) Patent No.: US 9,447,152 B2
(45) Date of Patent: Sep. 20, 2016

(54) BASE-DETECTING PORE

(75) Inventors: James Anthony Clarke, Oxford (GB); Lakmal Jayasinghe, Oxford (GB); Terence Reid, Oxford (GB); John Hagan Pryce Bayley, Oxford (GB)

(73) Assignee: Oxford Nanopore Technologies Limited, Oxford (GB)

( * ) Notice: Subject to any disclaimer, the term of this patent is extended or adjusted under 35 U.S.C. 154(b) by 917 days.

(21) Appl. No.: 13/002,717

(22) PCT Filed: Jul. 6, 2009

(86) PCT No.: PCT/GB2009/001690
§ 371 (c)(1),
(2), (4) Date: Mar. 30, 2011

(87) PCT Pub. No.: WO2010/004273
PCT Pub. Date: Jan. 14, 2010

(65) Prior Publication Data
US 2011/0177498 A1    Jul. 21, 2011

Related U.S. Application Data

(60) Provisional application No. 61/078,687, filed on Jul. 7, 2008.

(51) Int. Cl.
*C12Q 1/68* (2006.01)
*C07K 14/245* (2006.01)

(52) U.S. Cl.
CPC ........... *C07K 14/245* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 5,561,043 A | 10/1996 | Cantor et al. | |
| 5,777,078 A | 7/1998 | Bayley et al. | |
| 5,795,782 A | 8/1998 | Church et al. | |
| 5,817,771 A | 10/1998 | Bayley et al. | |
| 5,985,834 A | 11/1999 | Engel et al. | |
| 6,015,714 A | 1/2000 | Baldarelli et al. | |
| 6,127,166 A | 10/2000 | Bayley et al. | |
| 6,251,610 B1 | 6/2001 | Gupte et al. | |
| 6,362,002 B1 | 3/2002 | Denison et al. | |
| 6,426,231 B1 | 7/2002 | Bayley et al. | |
| 6,451,563 B1 | 9/2002 | Wittig et al. | |
| 6,824,659 B2 | 11/2004 | Bayley et al. | |
| 6,916,665 B2 | 7/2005 | Bayley et al. | |
| 6,927,070 B1 | 8/2005 | Bayley et al. | |
| 8,105,846 B2 | 1/2012 | Bayley et al. | |
| 2002/0028458 A1 | 3/2002 | Lexow | |
| 2002/0094526 A1 | 7/2002 | Bayley et al. | |
| 2003/0087232 A1 | 5/2003 | Christians et al. | |
| 2003/0099951 A1 | 5/2003 | Akeson et al. | |
| 2003/0108902 A1 | 6/2003 | Abarzua | |
| 2003/0118595 A1 | 6/2003 | Niemeyer et al. |
| 2003/0166137 A1 | 9/2003 | Zuker et al. |
| 2003/0215881 A1 | 11/2003 | Bayley et al. |
| 2004/0214177 A1 | 10/2004 | Bension |
| 2004/0229315 A1 | 11/2004 | Lee et al. |
| 2005/0053961 A1 | 3/2005 | Akeson et al. |
| 2005/0260655 A1 | 11/2005 | Liu et al. |
| 2007/0015182 A1 | 1/2007 | Abarzua |
| 2007/0122885 A1 | 5/2007 | Reeves et al. |
| 2008/0166724 A1 | 7/2008 | Gerber et al. |
| 2008/0206252 A1 | 8/2008 | Pennica et al. |
| 2009/0256116 A1 | 10/2009 | Shumaker-Parry et al. |
| 2009/0298075 A1 | 12/2009 | Travers et al. |
| 2010/0221212 A1 | 9/2010 | Stagliano et al. |
| 2011/0019186 A1 | 1/2011 | Himmelhaus et al. |
| 2011/0177498 A1 | 7/2011 | Clarke et al. |
| 2011/0311965 A1 | 12/2011 | Maglia et al. |
| 2012/0064599 A1 | 3/2012 | Jayasinghe et al. |
| 2013/0143802 A1 | 6/2013 | Chilkoti |
| 2013/0195908 A1 | 8/2013 | Leonetti et al. |
| 2014/0051069 A1 | 2/2014 | Jayasinghe et al. |
| 2014/0206842 A1 | 7/2014 | Majeed et al. |
| 2015/0008126 A1 | 1/2015 | Maglia et al. |
| 2015/0031020 A1 | 1/2015 | Jayasinghe et al. |
| 2015/0175663 A1 | 6/2015 | Yokoi et al. |

FOREIGN PATENT DOCUMENTS

| | | |
|---|---|---|
| GB | 2130219 | 5/1984 |
| GB | 2453377 | 4/2009 |
| JP | 11-137260 | 5/1999 |
| WO | 99/05167 A1 | 2/1999 |
| WO | 00/28312 A1 | 5/2000 |
| WO | 01/40516 A2 | 6/2001 |
| WO | 01/42782 A1 | 6/2001 |
| WO | 01/59453 A2 | 8/2001 |
| WO | 02/42496 A2 | 5/2002 |
| WO | 03/095669 A1 | 11/2003 |
| WO | 2005/056750 A2 | 6/2005 |
| WO | 2006/020775 A2 | 2/2006 |
| WO | 2006/028508 A2 | 3/2006 |
| WO | 2007/057668 A1 | 5/2007 |
| WO | 2007/075987 A1 | 7/2007 |
| WO | 2008/045575 A2 | 4/2008 |
| WO | 2008/083554 A1 | 7/2008 |
| WO | 2008/102120 A1 | 8/2008 |
| WO | 2008/102121 A1 | 8/2008 |
| WO | 2008/124107 A1 | 10/2008 |
| WO | 2010/004265 A1 | 1/2010 |

OTHER PUBLICATIONS

Bowie et al. (Science, 1990, 247:1306-1310).*

(Continued)

*Primary Examiner* — Brian J Gangle
(74) *Attorney, Agent, or Firm* — Wolf, Greenfield & Sacks, P.C.

(57) ABSTRACT

The invention relates to a mutant α-hemolysin (α-HL) pore which is useful for detecting one or more nucleotides by stochastic sensing. The pore is particularly useful for sequencing DNA or RNA. A molecular adaptor that allows detection of the nucleotide(s) is covalently attached to the pore. The pore is specifically modified to facilitate positioning of the adaptor and may be modified to facilitate covalent attachment.

32 Claims, 38 Drawing Sheets

(56) References Cited

OTHER PUBLICATIONS

Burgess et al. (J. Cell Biol. 111:2129-2138, 1990).*
Lazar et al. (Mol. Cell. Biol., 8:1247-1252, 1988).*
Astier, Yann et al., "Stochastic Detection of Motor Protein-RNA Complexes by Single-Channel Current Recording," ChemPhysChem, vol. 8:2189-2194 (2007).
Benner, Seico et al., "Sequence-specific detection of individual DNA polymerase complexes in real time using a nanopore," Nature Nanotechnology, vol. 2:718-724 (2007).
Cockroft, Scott L. et al., "A Single-Molecule Nanopore Device Detects DNA Polymerase Activity with Single-Nucleotide Resolution," J.Am. Chem. Soc., vol. 130:818-820 (2008).
Eliseev, Alexey V. et al., "Aminocyclodextrins as Selective Hosts with Several Binding Sites for Nucleotides," Angew. Chem. Int. Ed. Engl., vol. 32(9):1331-1333 (1993).
Eliseev, Alexey V. et al., "Molecular Recognition of Nucleotides, Nucleosides, and Sugars by Aminocyclodextrins," J. Am. Chem. Soc., vol. 116:6081-6088 (1994).
Tadey, Tanya et al., "Capillary electrophoretic separation of nucleotide isomers via complexation with cyclodextrin and borate," Journal of Chromatography B, vol. 657:365-372 (1994).
Tohda, Koji et al., "Channel Mimetic Sensing Membranes for Nucleotides Based on Multitopic Hydrogen Bonding," Israel Journal of Chemistry, vol. 37:267-275 (1997).
Travers, Kevin J. et al., "A flexible and efficient template format for circular consensus sequencing and SNP detection," Nucleic Acids Research, vol. 38(15):e159, doi:10.1093/nar/gkq543 (2010).
Tung, Ching-Hsuan, "Preparation and Applications of Peptide-Oligonucleotide Conjugates," Bioconjugate Chemistry, vol. 11(5):605-618 (2000).
Van De Goor, Tom A., "Nanopore Detection: Threading DNA Through a Tiny Hole," PharmaGenomics, vol. 4 (3):28-30 (2004).
Wang, Qian et al., "Bioconjugation by Copper(I)-Catalyzed Azide-Alkyne [3+2] Cycloaddition," J. Am. Chem. Soc., vol. 125:3192-3193 (2003).
Wang, Hui et al., "Nanopores with a spark for single-molecule detection," Nature Biotechnology, vol. 19:622-623 (2001).
Wemmer, David E. et al., "Preparation and melting of single strand circular DNA loops," Nucleic Acids Research, vol. 13(23):8611-8621 (1985).
Xie, Hongzhi et al., "Single-Molecule Observation of the Catalytic Subunit of cAMP-Dependent Protein Kinase Binding to an Inhibitor Peptide," Chemistry & Biology, vol. 12:109-120 (2005).
Yamagata, Atsushi et al., "Overexpression, purification and characterization of RecJ protein from Thermus thermophilus HB8 and its core domain," Nucleic Acids Research, vol. 29(22):4617-4624 (2001).
International Preliminary Report on Patentability and Written Opinion for Application No. PCT/GB2009/001679, 6 pages, dated Jan. 11, 2011.
International Search Report for Application No. PCT/GB2009/001679, 3 pages, dated Nov. 5, 2009.
International Preliminary Report on Patentability for Application No. PCT/GB2006/004265, 7 pages, dated May 20, 2008.
International Preliminary Report on Patentability for Application No. PCT/GB2008/003372, 6 pages, dated Apr. 7, 2010.
Ashkenasy, Nurit et al., "Recognizing a Single Base in an Individual DNA Strand: A Step Toward DNA Sequencing in Nanopores," Angew. Chem. Int. Ed., vol. 44:1401-1404 (2005).
Astier, Yann et al., "Toward Single Molecule DNA Sequencing: Direct Identification of Ribonucleoside and Deoxyribonucleoside 5'-Monophosphates by Using an Engineered Protein Nanopore Equipped with a Molecule Adapter," J. Am. Chem. Soc., vol. 128(5):1705-1710 (2006).
Bayley, Hagan et al., "Stochastic sensors inspired by biology," Nature, vol. 413:226-230 (2001).
Braha, Orit et al., "Carriers versus Adapters in Stochastic Sensing," ChemPhysChem, vol. 6:889-892 (2005).
Braha, Orit et al., "Designed protein pores as components for biosensors," Chemistry & Biology, vol. 4:497-505 (1997).
Busam, Robert D., "Structure of *Escherichia coli* exonuclease I in complex with thymidine 5'-monophosphate," Acta Cryst., vol. D64:206-210 (2008).
Cheley, Stephen et al., "A functional protein pore with a 'retro' transmembrane domain," Protein Science, vol. 8:1257-1267 (1999).
Cheley, Stephen et al., "Spontaneous oligomerization of a *staphylococcal* alpha-hemolysin conformationally constrained by removal of residues that form the transmembrane beta-barrel," Protein Engineering, vol. 10 (12):1433-1443 (1997).
Chen, Min et al., "Outer membrane protein G: Engineering a quiet pore for biosensing," PNAS, vol. 105 (17):6272-6277 (2008).
Dapprich, Johannes, "Single-Molecule DNA Digestion by Lambda-Exonuclease," Cytometry, vol. 36:163-168 (1999).
Genschel, Jochen et al., "Interaction of *E. coli* Single-Stranded DNA Binding Protein (SSB) with Exonuclease I. The Carboxy-Terminus of SSB Is the Recognition Site fo the Nuclease," Biol. Chem., vol. 381:183-192 (2000).
Gu, Li-Qun et al., "Stochastic sensing of organic analytes by a pore-forming protein containing a molecular adapter," Nature, vol. 398:686-690 (1999).
Guan, Xiyun et al., "Stochastic Sensing of TNT with a Genetically Engineered Pore," ChemBioChem, vol. 6:1875-1881 (2005).
Han, Eugene S. et al., "RecJ exonuclease: substrates, products and interaction with SSB," Nucleic Acids Research, vol. 34(4):1084-1091 (2006).
Hornblower, Breton et al., "Single-molecule analysis of DNA-protein complexes using nanopores," Nature Methods, vol. 4(4):315-317 (2007).
Howorka, S. et al., "Improved Protocol for High-Throughput Cysteine Scanning Mutagenesis," Biotechniques, vol. 25(5):764-766 (1998).
Kovall, Rhett et al., "Toroidal Structure of Lambda-Exonuclease," Science, vol. 277:1824-1827 (1997).
Lovett, Susan T. et al., "Identification and purification of a single-stranded-DNA-specific exonuclease encoded by the recJ gene of *Escherichia coli*," Proc. Natl. Acad. Sci. USA, vol. 86:2627-2631 (1989).
Mol, Clifford D. et al., "Structure and function of the multifunctional DNA-repair enzyme exonuclease III," Nature, vol. 374:381-386 (1995).
Sanchez-Quesada, Jorge et al., "Cyclic Peptides as Molecular Adapters for a Pore-Forming Protein," Journal of the American Chemical Society, vol. 122(48):11757-11766 (2000).
Sanderson, Katherine, "Standard and Pores. Could the next generation of genetic sequencing machines be built froma collection of miniscule holes?" Nature News, vol. 456(7218):23-25 (2008).
Shin, Seong-Ho et al., "Kinetics of a Reversible Covalent-Bond-Forming Reaction Observed at the Single-Molecule Level," Angew. Chem. Int. Ed., vol. 41(19):3707-3709 (2002).
Song, Langzhou et al., "Structure of *Staphylococcal* alpha-Hemolysin, a Heptameric Transmembrane Pore," Science, vol. 274:1859-1866 (1996).
Thomas, Kirk R. et al., "Processivity of DNA Exonucleases," The Journal of Biological Chemistry, vol. 253(2):424-429 (1978).
Walker, Barbara et al., "Key Residues for Membrane Binding, Oligomerization and Pore Forming Activity of *Staphylococcal* alpha-Hemolysin Identified by Cysteine Scanning Mutagenesis and Targeted Chemical Modification," The Journal of Biological Chemistry, vol. 270 (39):23065-23071 (1995).
Wu, Hai-Chen et al., "Protein Nanopores with Covalently Attached Molecular Adapters," J. Am. Chem. Soc., vol. 129:16142-16148 (2007).
International Search Report for Application No. PCT/GB2009/001690, dated Oct. 13, 2009.
International Preliminary Report on Patentability and Written Opinion for Application No. PCT/GB2009/001690, dated Jan. 11, 2011.
Akeson, Mark et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77:3227-3233 (1999).
Amblard, Franck et al., "The Cu(I)-catalyzed Huisgen azide-alkyne 1,3-dipolar cycloaddition reaction in nucleotide and oligonucleotide chemistry," Chem. Rev., vol. 109(9):4207-4220 (2009).

(56) References Cited

OTHER PUBLICATIONS

Ashkenasy, Nurit et al., "Single Nucleobase Sensitivity of a-Hemolysin (a-HL) Transmembrane Protein Pore: Toward Single DNA Sequencing," ACS National Meeting, vol. 45(13), Abstract No. 74 (2005).
Bayley, Hagan, "Sequencing single molecules of DNA," Current Opinion in Chemical Biology, vol. 10:628-637 (2006).
Branton, Daniel et al., "The potential and challenges of nanopore sequencing," Nat. Biotechnol., vol. 26 (10):1146-1153 (2008).
Braslavsky, Ido et al., "Sequence information can be obtained from single DNA molecules," PNAS, vol. 100 (7):3960-3964 (2003).
Budanova, Natalia et al., "Heptakis(6-amino-6-deoxy)-beta-cyclodextrin as a chiral selector for the separation of anionic analyte enantiomers by capillary electrophoresis," Electrophoresis, vol. 25:2795-2800 (2004).
Chan, Eugene Y., "Advances in sequencing technology," Mutation Research, vol. 573:13-40 (2005).
Cheley, Stephen et al., "A Genetically Encoded Pore for the Stochastic Detection of a Protein Kinase," ChemBioChem, vol. 7:1923-1927 (2006).
Cheley, Stephen et al., "Stochastic Sensing of Nanomolar Inositol 1,4,5-Triphosphate with an Engineered Pore," Chemistry & Biology, vol. 9:829-838 (2002).
Deamer, David W. et al., "Characterization of Nucleic Acids by Nanopore Analysis," Ac. Chem. Res., vol. 35:817-825 (2002).
Deamer, David W. et al., "Nanopores and nucleic acids: prospects for ultrarapid sequencing," TIBTECH, vol. 18:147-151 (2000).
Dorre, Klaus et al., "Techniques for single molecule sequencing," Bioimaging, vol. 5:139-152 (1997).
Eid, John et al., "Real-Time DNA Sequencing from Single Polymerase Molecules," Science, vol. 323:133-138 (2009).
Erie, Dorothy et al., "A Dumbell-Shaped, Double-Hairpin Structure of DNA: A Thermodynamic Investigation," Biochemistry, vol. 26:7150-7159 (1987).
Flusberg, Benjamin A. et al., "Direct detection of DNA methylation during single-molecule, real-time sequencing," Nature Methods, vol. 7(6):461-465 (2010).
Gu, Li-Qun et al., "Capture of a Single Molecule in a Nanocavity," Science, vol. 291:636-640 (2001).
Gu, Li-Qun et al., "Electroosmotic enhancement of the binding of a neutral molecule to a transmembrane pore," PNAS, vol. 100(26):15498-15503 (2003).
Gu, Li-Qun et al., "Reversal of charge selectivity in transmembrane protein pores by using noncovalent molecular adapters," PNAS, vol. 97(8):3959-3964 (2000).
Hein, Christopher D. et al., "Click Chemistry, a Powerful Tool for Pharmaceutical Sciences," Pharm. Res., vol. 25 (10):2216-2230 (2008).
Holden, Matthew A. et al., "Functional Bionetworks from Nanoliter Water Droplets," J. Am. Chem. Soc., vol. 129:8650-8655 (2007).
Howorka, Stefan et al., "DNA Duplex Formation of Individual DNA Strands within a Single Protein Pore," Biophysical Journal, vol. 82(1, pt. 2):508a, No. 2482-Plat (2002).
Howorka, Stefan et al., "Kinetics of duplex formation for individual DNA strands within a single protein nanopore," PNAS, vol. 98(23):12996-13001 (2001).
Howorka, Stefan et al., "Sequence-specific detection of individual DNA strands using engineered nanopores," Nature Biotechnology, vol. 19:636-639 (2001).
Hwang, William L. et al., "Electrical Behavior of Droplet Interface Bilayer Networks: Experimental Analysis and Modeling," J. Am. Chem. Soc., vol. 129:11854-11864 (2007).
Kalisch, Bernd W. et al., "Covalently linked sequencing primer linkers (splinkers) for sequence analysis of restriction fragments (Recombinant DNA; hairpin ligation; synthetic oligodeoxynucleotides; dideoxynucleotides)," Gene, vol. 44:263-270 (1986).
Kang, Xiao-feng et al., "Single Protein Pores Containing Molecular Adapters at High Temperatures," Angew. Chem. Int. Ed., vol. 44:1495-1499 (2005).

Kasianowicz, John J. et al., "Characterization of individual polynucleotide molecules using a membrane channel," Proc. Natl. Acad. Sci. USA, vol. 93:13770-13773 (1996).
Khulbe, Pramod K. et al., "DNA translocation through a-hemolysin nanopores with potential application to macromolecular data storage," Journal of Applied Physics, vol. 97(104317):1-7 (2005).
Kocalka, Petr et al., "Rapid and Efficient DNA Strand Cross-Linking by Click Chemistry," ChemBioChem, vol. 9:1280-1285 (2008).
Kolb, Hartmuth C. et al., "Click Chemistry: Diverse Chemical Function from a Few Good Reactions," Angew. Chem. Int. Ed., vol. 40:2004-2021 (2001).
Li, Jiali et al., "DNA molecules and configurations in a solid-state nanopore microscope," Nature, vol. 2:611-615 (2003).
Lovrinovic, Marina et al., "Rapid synthesis of DNA-cysteine conjugates for expressed protein ligation," Biochemical and Biophysical Research Communications, vol. 335:943-948 (2005).
Lutz, Jean-Francois et al., "Efficient construction of therapeutics, bioconjugates, biomaterials and bioactive surfaces using azide-alkyne 'click' chemistry," Advanced Drug Delivery Reviews, vol. 60:958-970 (2008).
Martînez, Javier et al., "The mRNA Cap Structure Stimulates Rate of Poly(A) Removal and Amplifies Processivity of Degradation," The Journal of Biological Chemistry, vol. 276(30):27923-27929 (2001).
Marziali, Andre et al., "New DNA Sequencing Methods," Annu. Rev. Biomed. Eng., vol. 3:195-223 (2001).
Mathé, Jérôme et al., "Orientation discrimination of a single-stranded DNA inside the a-hemolysin membrane channel," PNAS, vol. 102(35):12377-12382 (2005).
Matsuura, Shun-ichi et al., "Real-time observation of a single DNA digestion by I exonuclease under a fluorescence microscope field," Nucleic Acids Research, vol. 29(16):1-5 (2001).
Meller, Amit et al., "Rapid nanopore discrimination between single polynucleotide molecules," PNAS, vol. 97 (3):1079-1084 (2000).
Movileanu, Llviu et al., "Detecting protein analytes that modulate transmembrane movement of a polymer chain within a single protein pore," Nature Biotechnology, vol. 18:1091-1095 (2001).
Muller, Joachim et al., "DNA-directed assembly of artificial multienzyme complexes," Biochemical and Biophysical Research Communications, vol. 377:62-67 (2008).
Nakane, Jonathan et al., "A Nanosensor for Transmembrane Capture and Identification of Single Nucleic Acid Molecules," Biophysical Journal, vol. 87:615-621 (2004).
Nakane, Jonathan J. et al., "Nanopore sensors for nucleic acid analysis," J. Phys.: Condens. Matter, vol. 15:R1365-R1393 (2003).
Niemeyer, Christof M. et al., "DNA-Directed Assembly of Bienzymic Complexes from in Vivo Biotinylated NAD(P)H: FMN Oxidoreductase and Luciferase," ChemBioChem., vol. 3:242-245 (2002).
Nwe, Kido et al., "Growing Applications of 'Click Chemistry' for Bioconjugation in Comtemporary Biomedical Research," Cancer Biotherapy and Radiopharmaceuticals, vol. 24(3):289-302 (2009).
Paner, Teodoro M. et al., "Studies of DNA Dumbells. III. Theoretical Analysis of Optical Melting Curves of Dumbells with a 16 Base-Pair Duplex Stem and Tn End Loops (n=2, 3, 4, 5, 6, 8, 10, 14)," Biopolymers, vol. 32(7):881-892 (1992).
Paner, Teodoro M. et al., "Studies of DNA Dumbells. VI. Analysis of Optical Melting Curves of Dumbells with a Sixteen-Base Pair Duplex Stem and End-Loops of Variable Size and Sequence," Biopolymers, vol. 39:779-793 (1996).
Seeman, Nadrian C., "Nucleic Acid Junctions and Lattices," J. theor. Biol., vol. 99:237-247 (1982).
Seo, Tae Seok et al., "Click Chemistry to Construct Fluorescent Oligonucleotides for DNA Sequencing," J. Org. Chem., vol. 68:609-612 (2003).
Sutherland, Todd C. et al., "An analysis of mismatched duplex DNA unzipping through a bacterial nanopore," Biochem. Cell Biol., vol. 82:407-412 (2004).
Clarke, James et al., "Continuous base identification for single-molecule nanopore DNA sequencing," Nature Nanotechnology, vol. 4:265-270 (2009).

(56) References Cited

OTHER PUBLICATIONS

Wolfe, Aaron J. et al., "Catalyzing the Translocation of Polypeptides through Attractive Interactions," J. Am. Chem. Soc., vol. 129:14034-14041 (2007).
U.S. Appl. No. 13/968,778, filed Aug. 16, 2013, Lakmal Jayasinghe.
U.S. Appl. No. 14/455,394, filed Aug. 8, 2014, Lakmal Jayasinghe.
U.S. Appl. No. 13/129,278, filed Aug. 26, 2011, Giovanni Maglia.
U.S. Appl. No. 14/334,285, filed Jul. 17, 2014, Giovanni Maglia.
U.S. Appl. No. 13/260,178, filed Jan. 17, 2012, David Stoddart.
U.S. Appl. No. 13/338,794, filed Dec. 28, 2011, Hagan Bayley, Mar. 13, 2014.
U.S. Appl. No. 13/338,794, filed Dec. 28, 2011, Hagan Bayley, Mar. 5, 2013.
U.S. Appl. No. 12/681,643, filed Jun. 15, 2010, John Hagan Bayley, Apr. 24, 2014.
U.S. Appl. No. 12/681,643, filed Jun. 15, 2010, John Hagan Bayley, Nov. 6, 2013.
U.S. Appl. No. 12/681,643, filed Jun. 15, 2010, John Hagan Bayley, Mar. 8, 2013.
U.S. Appl. No. 13/147,171, filed Nov. 10, 2011, Ruth Moysey, May 6, 2013.
U.S. Appl. No. 13/147,159, filed Nov. 15, 2011, Brian Mckeown, Jul. 17, 2014.
U.S. Appl. No. 13/147,159, filed Nov. 15, 2011, Brian Mckeown, Dec. 18, 2013.
U.S. Appl. No. 13/147,159, Nov. 15, 2011, Brian Mckeown, May 28, 2013.
U.S. Appl. No. 13/002,709, filed May 13, 2011, Lakmal Jayasinghe, Mar. 10, 2014.
U.S. Appl. No. 13/002,709, filed May 13, 2011, Lakmal Jayasinghe, Jun. 27, 2013.
U.S. Appl. No. 13/002,709, filed May 13, 2011, Lakmal Jayasinghe, Dec. 21, 2012.
U.S. Appl. No. 13/968,778, filed Aug. 16, 2013, Lakmal Jayasinghe, Jul. 9, 2014.
U.S. Appl. No. 13/129,278, filed Aug. 26, 2011, Giovanni Maglia, Feb. 18, 2014.
U.S. Appl. No. 13/129,278, filed Aug. 26, 2011, Giovanni Maglia, Jun. 11, 2013.
U.S. Appl. No. 13/129,278, filed Aug. 26, 2011, Giovanni Maglia, Feb. 27, 2013.
U.S. Appl. No. 13/260,178, filed Nov. 18, 2011, Lakmal Jayasinghe, Jan. 14, 2014.
U.S. Appl. No. 13/260,178, filed Nov. 18, 2011, Lakmal Jayasinghe, May 9, 2013.
U.S. Appl. No. 13/260,178, filed Nov. 18, 2011, Lakmal Jayasinghe, Feb. 20, 2013.
Avrameas, S., "Coupling of Enzymes to Proteins with Glutaraldehyde, Use of the Conjugates for the Detection of Antigens and Antibodies," Immunochemistry, vol. 6, pp. 45-52 (1969).
U.S. Appl. No. 14/858,138, filed Sep. 18, 2015, Lakmal Jayasinghe.
U.S. Appl. No. 13/147,176, filed Nov. 18, 2011, Lakmal Jayasinghe.
U.S. Appl. No. 13/968,778, Mar. 20, 2015.
U.S. Appl. No. 14/455,394, Oct. 2, 2015.
U.S. Appl. No. 14/455,394, May 8, 2015.
U.S. Appl. No. 14/334,285, Aug. 21, 2015.
U.S. Appl. No. 14/334,285, Feb. 9, 2015.
U.S. Appl. No. 13/260,178, Aug. 18, 2015.
U.S. Appl. No. 13/260,178, Feb. 26, 2015.
U.S. Appl. No. 13/147,176, Aug. 31, 2015.
U.S. Appl. No. 13/147,176, May 8, 2015.
U.S. Appl. No. 13/147,176, Oct. 20, 2014.
U.S. Appl. No. 13/147,176, Mar. 14, 2014.

\* cited by examiner

Figure 26
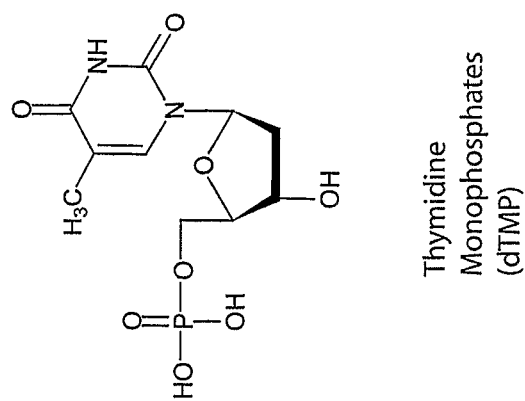
Thymidine Monophosphates (dTMP)
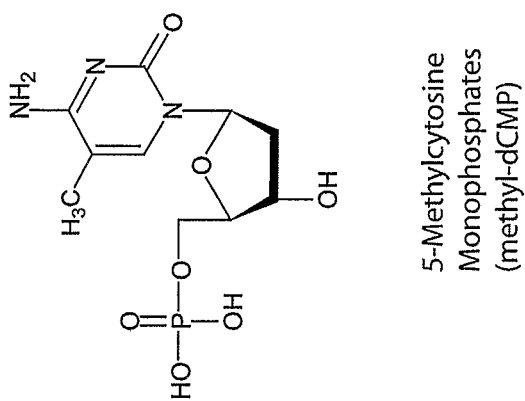
5-Methylcytosine Monophosphates (methyl-dCMP)
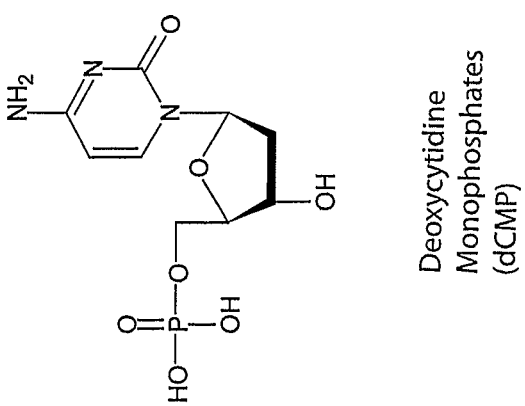
Deoxycytidine Monophosphates (dCMP)

Figure 28
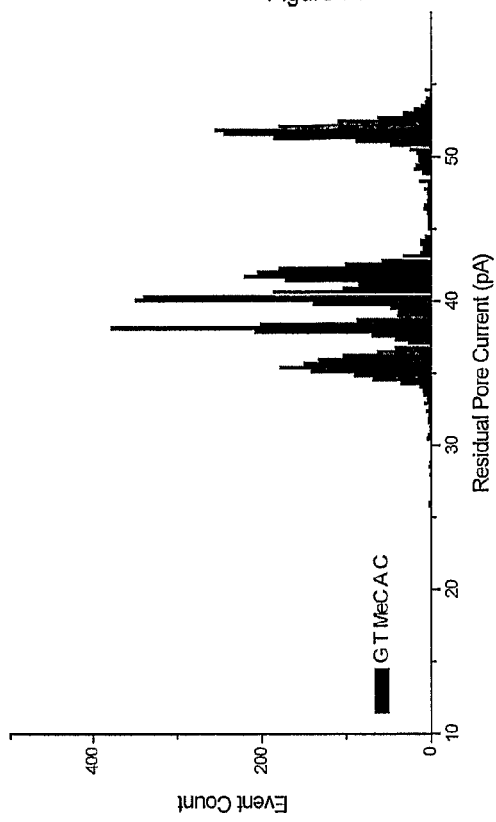
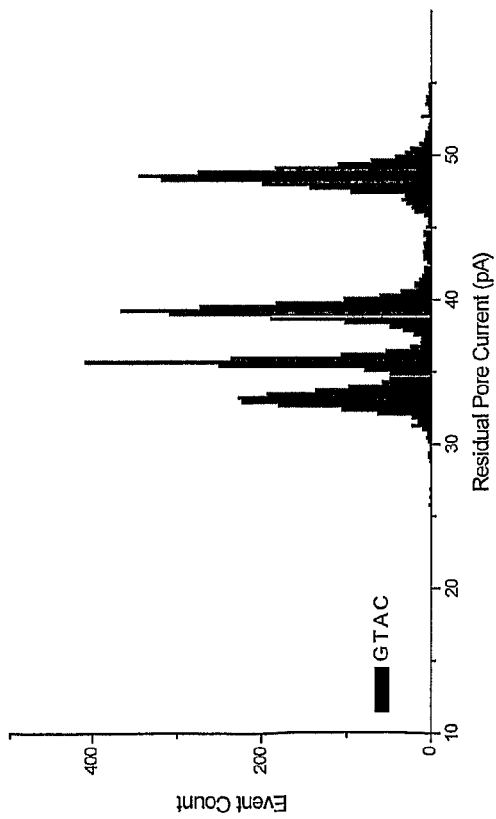

Figure 31
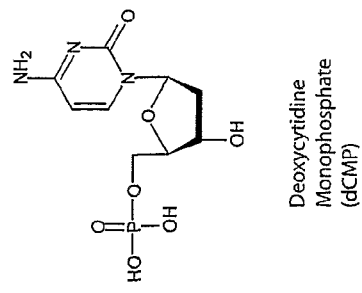
Deoxycytidine Monophosphate (dCMP)
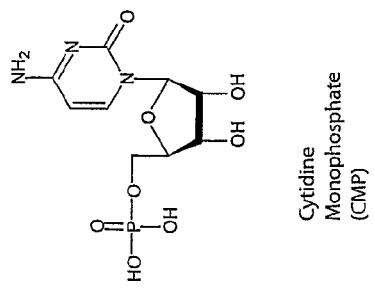
Cytidine Monophosphate (CMP)
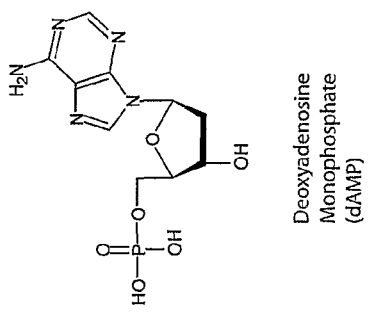
Deoxyadenosine Monophosphate (dAMP)
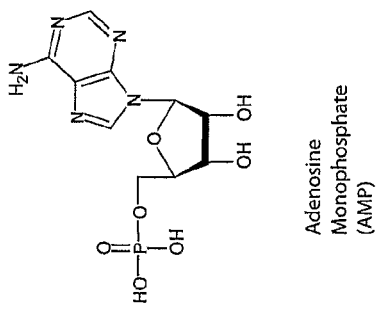
Adenosine Monophosphate (AMP)
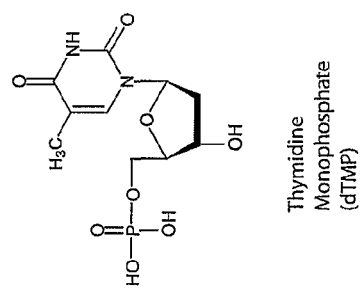
Thymidine Monophosphate (dTMP)
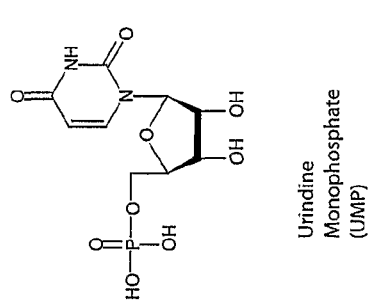
Uridine Monophosphate (UMP)
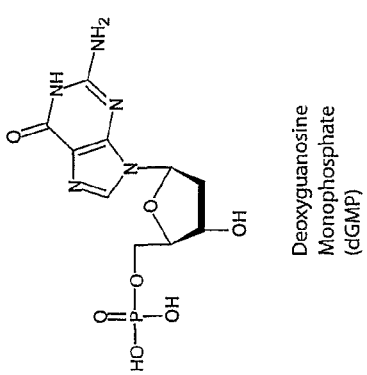
Deoxyguanosine Monophosphate (dGMP)
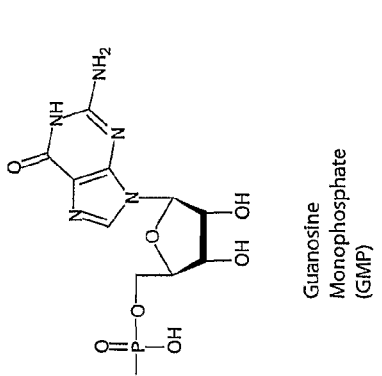
Guanosine Monophosphate (GMP)
DNA Bases | RNA Bases

BASE-DETECTING PORE

RELATED APPLICATIONS

This application is a 35 U.S.C. 371 national stage filing of International Application No. PCT/GB2009/001690 filed Jul. 6, 2009, which claims priority to U.S. Ser. No. 61/078,687 filed Jul. 7, 2008. The contents of the aforementioned applications are hereby incorporated by reference.

FIELD OF THE INVENTION

The invention relates to a mutant α-hemolysin (α-HL) pore which is useful for detecting one or more nucleotides by stochastic sensing. The pore is particularly useful for sequencing DNA or RNA. A molecular adaptor that allows detection of the nucleotide(s) is covalently attached to the pore. The pore is specifically modified to facilitate positioning of the adaptor and may be modified to facilitate covalent attachment.

BACKGROUND OF THE INVENTION

Stochastic detection is an approach to sensing that relies on the observation of individual binding events between nucleotide molecules and a receptor. Stochastic sensors can be created by placing a single pore of nanometer dimensions in an insulating membrane and measuring voltage-driven ionic transport through the pore in the presence of nucleotide molecules. The frequency of occurrence of fluctuations in the current reveals the concentration of an nucleotide that binds within the pore. The identity of an nucleotide is revealed through its distinctive current signature, notably the duration and extent of current block (Braha, O., Walker, B., Cheley, S., Kasianowicz, J. J., Song, L., Gouaux, J. E., and Bayley, H. (1997) *Chem. Biol.* 4, 497-505; and Bayley, H., and Cremer, P. S. (2001) *Nature* 413, 226-230).

Engineered versions of the bacterial pore forming toxin α-hemolysin (α-HL) have been used for stochastic sensing of many classes of molecules (Bayley, H., and Cremer, P. S. (2001) *Nature* 413, 226-230; Shin, S.-H., Luchian, T., Cheley, S., Braha, O., and Bayley, H. (2002) *Angew. Chem. Int. Ed.* 41, 3707-3709; and Guan, X., Gu, L.-Q., Cheley, S., Braha, O., and Bayley, H. (2005) *ChemBioChem* 6, 1875-1881). In the course of these studies, it was found that attempts to engineer α-HL to bind small organic nucleotides directly can prove taxing, with rare examples of success (Guan, X., Gu, L.-Q., Cheley, S., Braha, O., and Bayley, H. (2005) *ChemBioChem* 6, 1875-1881). Fortunately, a different strategy was discovered, which utilized non-covalently attached molecular adaptors, notably cyclodextrins (Gu, L.-Q., Braha, O., Conlan, S., Cheley, S., and Bayley, H. (1999) *Nature* 398, 686-690), but also cyclic peptides (Sanchez-Quesada, J., Ghadiri, M. R., Bayley, H., and Braha, O. (2000) *J. Am. Chem. Soc.* 122, 11758-11766) and cucurbiturils (Braha, O., Webb, J., Gu, L.-Q., Kim, K., and Bayley, H. (2005) *ChemPhysChem* 6, 889-892). Cyclodextrins become transiently lodged in the α-HL pore and produce a substantial but incomplete channel block. Organic nucleotides, which bind within the hydrophobic interiors of cyclodextrins, augment this block allowing nucleotide detection (Gu, L.-Q., Braha, O., Conlan, S., Cheley, S., and Bayley, H. (1999) *Nature* 398, 686-690).

There is currently a need for rapid and cheap DNA or RNA sequencing technologies across a wide range of applications. Existing technologies are slow and expensive mainly because they rely on amplification techniques to produce large volumes of nucleic acid and require a high quantity of specialist fluorescent chemicals for signal detection. Stochastic sensing has the potential to provide rapid and cheap DNA sequencing by reducing the quantity of nucleotide and reagents required.

SUMMARY OF THE INVENTION

The inventors have surprisingly demonstrated that a mutant α-HL pore having a molecular adaptor covalently attached to a lower part of its barrel or channel such that it is positioned at or near residue 139 is capable of detecting and distinguishing between nucleotides. In particular, the inventors have shown that a mutant α-HL pore having a molecular adaptor covalently attached such that it is positioned at or near residue 139 is capable of distinguishing between different nucleotides. This pore is highly sensitive and can therefore be used to sequence nucleic acids, such as DNA or RNA.

The inventors have also surprisingly demonstrated that a mutant α-HL pore having a molecular adaptor covalently attached such that it is positioned at or near residue 139 is capable of distinguishing between different nucleotides under a range of different conditions. In particular, the pore will distinguish between nucleotides under conditions that are favourable to enzymes whose function is needed for the sequencing of nucleic acids.

The inventors have also surprisingly shown that modification of a mutant α-HL pore at and/or near residue 139 is essential for positioning the adaptor and detecting and distinguishing between different nucleotides.

The pores of the invention are useful tools for stochastic sensing, especially for detecting nucleotides or sequencing nucleic acids, such as DNA or RNA.

Accordingly, the invention provides a mutant α-HL pore for use in detecting one or more nucleotides in a sample, which comprises:
  (a) seven subunits each comprising the sequence shown in SEQ ID NO: 2 or a variant thereof; and
  (b) a molecular adaptor that facilitates an interaction between the pore and the nucleotide(s),
wherein one or more of the seven subunits is modified at and/or near residue 139 of SEQ ID NO: 2 to facilitate positioning of the adaptor, and
wherein the molecular adaptor is covalently attached to one or more of the subunits such that it is positioned at or near residue 139 of SEQ ID NO: 2.

The invention also provides:
  a polynucleotide sequence which encodes a subunit of α-HL having the sequence shown in SEQ ID NO: 2 or a variant thereof, wherein the subunit has a cysteine at position 119, 121 or 135 of SEQ ID NO: 2;
  a kit for producing a mutant α-HL pore, comprising seven polynucleotides each of which encode a subunit of α-HL having the sequence shown in SEQ ID NO: 2 or a variant thereof, wherein at least one of the subunits has cysteine at residue 119, 121 or 135 of SEQ ID NO: 2;
  a method of producing a pore of the invention, comprising:
    (a) providing a pore as defined above; and
    (b) covalently attaching to the pore a molecular adaptor that facilitates an interaction between the pore and one or more nucleotide(s);
  a method of identifying an individual nucleotide, comprising:

(a) contacting the nucleotide with a pore of the invention so that the nucleotide interacts with the pore; and (b) measuring the current passing through the pore during the interaction and thereby determining the identity of the nucleotide;

a method of sequencing a target nucleic acid sequence, comprising:

(a) digesting an individual nucleotide from one end of the target sequence using an exonuclease;

(b) contacting the nucleotide with a pore of the invention so that the nucleotide interacts with the adaptor;

(c) measuring the current passing through the pore during the interaction and thereby determining the identity of the nucleotide; and (d) repeating steps (a) to (c) at the same end of the nucleic acid sequence and thereby determining the sequence of the nucleic acid; and a kit for sequencing a nucleic acid, comprising:

(a) a pore of the invention or the seven polynucleotides as contained in the kits described above; and (b) an exonuclease.

DESCRIPTION OF THE FIGURES

FIG. 26 shows the chemical structures of the dCMP and methyl-dCMP (dTMP included for comparison).

FIG. 28 shows a histogram for the HL-(M113R/N139Q)$_6$(M113R/N139Q/L135C-D8)$_1$ mutant. Detection of all four standard nucleotide monophosphates (left) and all four standard nucleotide monophosphates with methyl-dCMP added (right) can be seen (800 mM KCl, 170 mV, pH 7.5).

FIG. 31 shows the chemical structures of the bases commonly found in DNA and the corresponding RNA bases.

DESCRIPTION OF THE SEQUENCE LISTING

Figure 1:
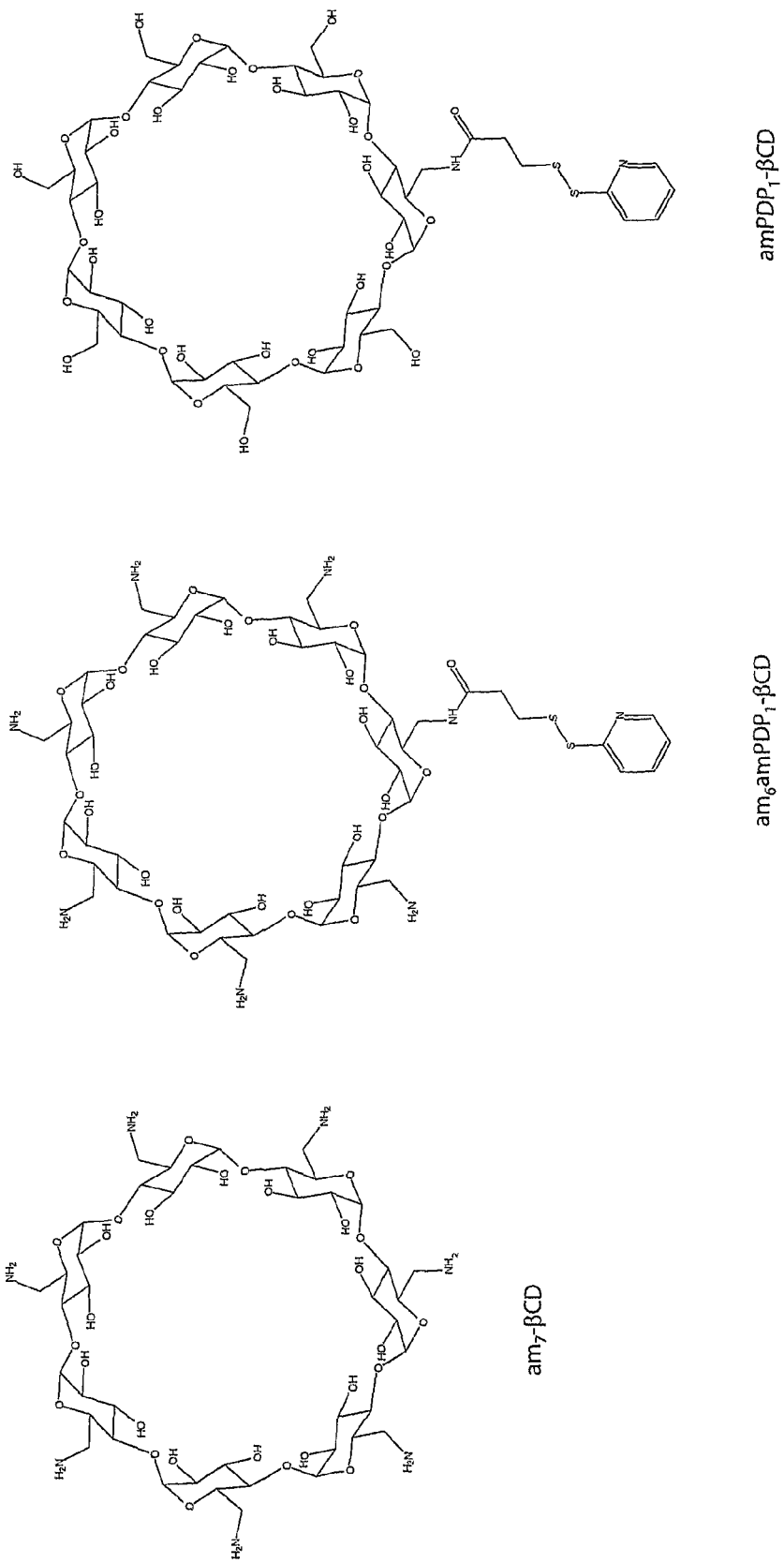
FIG. 1 shows the structure of the adaptor used in the Example. This Figures shows the structure of the unreacted adaptor, heptakis(6-deoxy-6-amino)-β-cyclodextrin (am$_7$-βCD), as well as the structure of the adaptor once it has been reacted with the bifunctional crosslinker succinimidyl 3-(2-pyridyldithio)propionate (SPDP) to form am$_6$amPDP$_1$-βCD. The Figure also shows the structure of the control adaptor used in the Examples to investigate the effect of the amine groups on the adaptor (amPDP$_1$-βCD).

SEQ ID NO: 1 shows the polynucleotide sequence that encodes one subunit of wild-type α-hemolysin (α-HL).

SEQ ID NO: 2 shows the amino acid sequence of one subunit of wild-type α-HL.

SEQ ID NO: 3 shows the polynucleotide sequence that encodes one subunit of α-HL M113R-RL2.

SEQ ID NO: 4 shows the amino acid sequence of one subunit of α-HL M113R-RL2.

SEQ ID NO: 5 shows the polynucleotide sequence that encodes one subunit of α-HL M113R with a wild-type background.

SEQ ID NO: 6 shows the amino acid sequence of one subunit of α-HL M113R with a wild-type background.

SEQ ID NO: 7 shows the polynucleotide sequence that encodes one subunit of α-HL M113R/N139Q.

SEQ ID NO: 8 shows the amino acid sequence of one subunit of α-HL M113R/N139Q.

SEQ ID NO: 9 shows the polynucleotide sequence that encodes one subunit of α-HL M113R/N139Q/G119C-D8.

SEQ ID NO: 10 shows the amino acid sequence of one subunit of α-HL M113R/N139Q/G119C-D8.

SEQ ID NO: 11 shows the polynucleotide sequence that encodes one subunit of α-HL M113R/N139Q/N121C-D8.

SEQ ID NO: 12 shows the amino acid sequence of one subunit of α-HL M113R/N139Q/N121C-D8.

SEQ ID NO: 13 shows the polynucleotide sequence that encodes one subunit of α-HL M113R/N139Q/L135C-D8.

SEQ ID NO: 14 shows the amino acid sequence of one subunit of α-HL M113R/N139Q/L135C-D8.

All of SEQ ID NOs 2, 4, 6, 8, 10, 12 and 14 are mature forms that lack the amino terminal methionine.

SEQ ID NO: 15 shows the polynucleotide sequence encoding the exonuclease III enzyme from *E. coli*.

SEQ ID NO: 16 shows the amino acid sequence of the exonuclease III enzyme from *E. coli*.

SEQ ID NO: 17 shows the polynucleotide sequence encoding the exonuclease I enzyme from *E. coli*.

SEQ ID NO: 18 shows the amino acid sequence of the exonuclease I enzyme from *E. coli*.

SEQ ID NO: 19 shows the polynucleotide sequence encoding the bacteriophage lambda exonuclease.

SEQ ID NO: 20 shows the amino acid sequence of the bacteriophage lambda exonuclease. The sequence is one of three identical subunits that assemble into a trimer.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a nucleotide" includes "nucleotides", reference to "a pore" includes two or more such pores, reference to "a molecular adaptor" includes two or more such adaptors, and the like.

All publications, patents and patent applications cited herein, whether supra or infra, are hereby incorporated by reference in their entirety.

Mutant α-HL Pores

The present invention provides mutant α-HL pores for use in detecting one or more nucleotide(s). The pores may also be used for distinguishing between or discriminating between different nucleotides. The pores comprise a molecular adaptor that facilitates an interaction with the nucleotide(s). The adaptor is covalently attached to the pore in a specific position. The adaptor is positioned such that, during the interaction between a nucleotide and the pore, the nucleotide affects the current flowing through the pore in a manner specific for that nucleotide. The adaptor is therefore covalently attached to the pore in a position that allows the pore to be used to detect the nucleotide or discriminate nucleotides via stochastic sensing.

The pores of the invention are useful tools for stochastic sensing. The pores of the invention are particularly useful for discriminating between nucleotides. The pores are therefore ideal for sequencing nucleic acids.

The pores of the invention can discriminate between different nucleotides with a high degree of sensitivity. The pores can easily distinguish between the four nucleotides in DNA and RNA. The pores of the invention can even distinguish between methylated and unmethylated nucleotides. The base resolution of a mutant α-HL pore having the adaptor covalently attached to residue 135 is surprisingly high. The pore shows almost complete separation of all four DNA nucleotides making it an excellent candidate for the sequencing of nucleic acids. The pore also allows deoxythymidine monophosphate (dTMP) to be clearly distinguished from the other three DNA nucleotides based on its longer dwell time in the pore. The pore further discriminates between deoxycytidine monophosphate (dCMP) and methyl-dCMP based on the dwell time in the pore and the current flowing through the pore.

The pores of the invention can also discriminate between different nucleotides under a range of conditions. In particular, the pores will discriminate between nucleotides under conditions that are favourable to the sequencing of nucleic acids. There are a number of ways that pores can be used to sequence DNA and RNA molecules. One way involves the use of an exonuclease enzyme. In this approach, the exonuclease enzyme is used to sequentially detach the nucleotides from the DNA or RNA strand. Such enzymes do not normally function under high salt concentrations. The pores of the invention are able to discriminate between nucleotides even at low salt concentrations. For instance, the pores can function with good nucleotide discrimination at a KCl concentration as low as 300 mM at room temperature. The pores will function with good nucleotide discrimination at lower salt concentrations if the temperature is increased or if asymmetric salt solutions are used. This is discussed in more detail below.

The extent to which the pores of the invention can discriminate between different nucleotides can be controlled by altering the applied potential. This allows the function of the pores to be fine-tuned, particularly when sequencing.

The fixed nature of the molecular adaptor also means that the signal obtained from the pore is entirely dependent on the presence of a nucleotide in the barrel or channel of the pore and is not affected by dissociation of the adaptor from the pore. In other words, the fixed nature of the adaptor means that a distinctive current will flow through the pore whenever a nucleotide interacts with the pore. This is particularly important for sequencing nucleic acids because every nucleotide in the sequence needs to be detected and identified.

The pores of the invention can be designed such that they do not undergo blocking. In electrophysiology, pores can become blocked by large multivalent ions. The ions become trapped in the barrel or channel of the pore and prevent the flow of ionic current. Blocking is normally avoided by carrying out experiments in ultra-high grade purity salt solution. The introduction of positively charged residues, such as arginine, near the constriction of the barrel or channel of α-HL generally results in pores that are prone to blocking. As will become apparent from the discussion below, it is not essential that the mutant α-HL pores of the invention have one or more positively charge residues near the constriction of their barrel or channel. Pores of the invention lacking such residues can be used in the presence of large multivalent ions without undergoing blocking.

Finally, the fixed nature of the molecular adaptor means that the pore and adaptor can be stored together, thereby allowing the production of a ready-to-use biosensor.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it present in a form that comprises less than 10%, less than 5%, less than 2% or less than 1% of other components, such as lipids or other pores. Alternatively, a pore of the invention may be present in a lipid bilayer.

A pore of the invention may be present as an individual or single pore. Alternatively, a pore of the invention may be present in a homologus or heterologous population of two or more pores.

The wild-type α-HL pore is formed of seven identical monomers or subunits (i.e. it is heptameric). The sequence of one wild-type monomer or subunit of α-hemolysin is shown in SEQ ID NO: 2. A mutant α-HL pore is a heptameric pore in which one or more of the seven subunits has an amino acid sequence which varies from that of SEQ ID NO: 2 and which retains pore activity. The pore includes modifications that facilitate positioning of the adaptor as discussed below. The pore preferably also contains modifications that facilitate covalent attachment of the adaptor.

1, 2, 3, 4, 5, 6 of the subunits in the pore may have an amino acid sequence that varies from that of SEQ ID NO: 2. In preferred embodiments, all of the subunits in the pore have an amino acid sequence that varies from that of SEQ ID NO: 2. All seven subunits within the pore may be identical but are typically different, particularly since different subunits are modified in different ways to facilitate positioning of the adaptor as discussed below and optionally to facilitate covalent attachment of the adaptor.

A mutant α-HL pore of the invention is formed from seven subunits each comprising the sequence shown in SEQ ID NO: 2 or a variant thereof. A variant is a subunit that has an amino acid sequence which varies from that of SEQ ID NO: 2 and which retains its ability to form a pore. All of the sequences shown in SEQ ID NOs: 4, 6, 8, 10, 12 and 14 are variants of SEQ ID NO: 2. Any of the specific modifications to SEQ ID NO: 2 discussed below also result in variants of SEQ ID NO: 2.

Variants include the constructs, which comprise the sequence shown in SEQ ID NO: 2 or a variant thereof and are described in a co-pending International application claiming priority from U.S. Application No. 61/078,695 and being filed simultaneously with this application [J A Kemp & Co Ref: N.104404A; Oxford Nanolabs Ref: ONL IP 005]. Such constructs also comprise a nucleic acid handling enzyme, such as an exonuclease. All the teachings of that application may be applied equally to the present invention.

The pore is modified to facilitate positioning of the adaptor so that the one or more nucleotides can be detected. One or amino acids are introduced into the pore to hold the adaptor in the correct position via non-covalent interactions, such as hydrophobic interactions, hydrogen bonding, Van der Waal's forces, π-cation interactions and/or electrostatic forces.

One or more of the seven subunits are modified at and/or near residue 139 of SEQ ID NO: 2. For instance, 2, 3, 4, 5, 6 or all of the seven subunits are modified at and/or near residue 139 of SEQ ID NO: 2. One or more of the seven subunits include at least one, such as 2, 3, 4 or 5, modifications at and/or near residue 139 of SEQ ID NO: 2.

One or more of the seven subunits are modified at residue 139 and/or near residue 139 of SEQ ID NO: 2. If one or more of the seven subunits are modified near residue 139, the modifications are sufficiently close to residue 139 that they can facilitate positioning of the adaptor. The modifications are typically made at positions that are less than 20 ångströms, such as less than 15, less than 10 or less than 5 ångströms, from residue 139 in SEQ ID NO: 2. Residues that are 2 or 3 amino acids from residue 139 in the sequence of SEQ ID NO: 2 are preferably modified in one or more of the seven subunits. Residue 139 and/or one or both of the residues adjacent to residue 139 in the sequence of SEQ ID NO: 2 are more preferably modified in one or more of the seven subunits. One or more of the seven subunits preferably comprise a modification at residue 136, 137, 138, 139, 140, 141 or 142 of SEQ ID NO: 2 or any combination thereof. One or more of the seven subunits most preferably comprise a modification at only residue 139 of SEQ ID NO: 2.

One or more of the seven subunits may comprise modifications at residues in SEQ ID NO: 2 that are near to residue 139 once the sequence is folded to form a three-dimensional subunit. One or more of the seven subunits preferably comprise a modification at residue 117, 119, 121, 123, 135, 137, 141 or 143 of SEQ ID NO: 2 or any combination thereof.

The subunits are preferably modified at and/or near to residue 139 by the introduction of polar, uncharged amino acids. Such amino acids may influence the positioning of the adaptor via hydrogen bonding. Their lack of charge also prevents electrostatic interactions from interfering with the function of the adaptor. Table 1 below lists polar, uncharged amino acids. Glutamine is a preferred polar, uncharged amino acid. The polar, uncharged amino acids can be inserted at and/or near residue 139. Alternatively, amino acids at and/or near residue 139 can be substituted with polar, uncharged amino acids.

One or more of the seven subunits are preferably modified to comprise glutamine, which is a polar, uncharged amino acid, at and/or near residue 139 of SEQ ID NO: 2. Glutamine can be inserted at and/or near residue 139 or amino acids at and/or near residue 139 can be substituted with glutamine. The amino acid at residue 139 is preferably substituted with glutamine (N139Q). For instance, 2, 3, 4, 5 or 6 of the seven subunits have glutamine at residue 139 of SEQ ID NO: 2. In preferred embodiments, all of the seven subunits have a glutamine at residue 139 of SEQ ID NO: 2. Uncharged glutamine at residue 139 is capable of interacting with chemical groups, such as hydroxyl groups, in the adaptor by hydrogen bonding and thereby facilitating the positioning of the adaptor within the barrel or channel of the mutant α-HL pore. Preferred subunits having residue 139 of SEQ ID NO: 2 substituted with glutamine (N139Q) are shown in SEQ ID NOs: 8, 10, 12 and 14. Suitable subunits may contain or lack the octa-asparate tail shown in SEQ ID NOs: 8, 10, 12 and 14.

The pore may also have other uncharged amino acids or even aromatic amino acids located near the constriction of the barrel or channel to further facilitate positioning of the adaptor. Table 1 below lists uncharged and aromatic amino acids. For instance, one or more of the seven subunits may have one or more uncharged amino acids, such as asparagine, or one or more aromatic amino acids, such as phenylalanine, located near the constriction of the barrel or channel. The pore preferably has a ring of 4, 5, 6 or preferably 7 uncharged or aromatic amino acids located near the constriction of the barrel or channel. Each amino acid in the ring is typically provided by each of the subunits. Residues of SEQ ID NO: 2 located near the constriction of the barrel or channel include, but are not limited to, 111, 113 and 147. Suitable subunits include an uncharged or aromatic amino acid at residue 111, 113 or 147 of SEQ ID NO: 2. The uncharged or aromatic amino acids can be inserted at residue 111, 113 or 147 of SEQ ID NO: 2. Alternatively, the amino acids at residue 111, 113 or 147 of SEQ ID NO: 2 can be substituted with uncharged or aromatic amino acids.

The pore is preferably modified to facilitate covalent attachment of the adaptor. One or more amino acids that are capable of forming a covalent bond, such as cysteine, can be introduced into one or more subunits. The amino acid may be naturally occurring or non-naturally occurring. An amino acid may be introduced by addition. An amino acid is preferably introduced by substitution. Amino acids can be introduced at any positions as long as the adaptor is positioned at or near residue 139 of SEQ ID NO: 2. If the amino acids are introduced at residues distant from residue 139, a bifunctional crosslinker of appropriate length may be used to ensure that the adaptor is positioned at or near residue 139.

In preferred embodiments, residue 119, 121 or 135 of SEQ ID NO: 2 is modified in one or more of the seven subunits to facilitate covalent attachment of the adaptor. In more preferred embodiments, residue 119, 121 or 135 of SEQ ID NO: 2 is modified in only one of the seven subunits to facilitate covalent attachment of the adaptor. The amino acid introduced at residue 119, 121 or 135 of SEQ ID NO: 2 is preferably cysteine. The amino acid at residue 119, 121 or 135 is preferably substituted with cysteine (G119C, N121C or L135C). A preferred subunit having position 119 of SEQ ID NO: 2 substituted with cysteine (G119C) is shown in SEQ ID NO: 10. A preferred subunit having residue 121 of SEQ ID NO: 2 substituted with cysteine (N121C) is shown in SEQ ID NO: 12. A preferred subunit having residue 135 of SEQ ID NO: 2 substituted with cysteine (L135C) is shown in SEQ ID NO: 14.

The pore preferably has positively charged amino acids located near the constriction of the barrel or channel to facilitate covalent attachment of the adaptor. For instance, one or more of the seven subunits may have positively charged amino acids, such as arginine, lysine or histidine, located near the constriction of the barrel or channel. The positively charged amino acids facilitate covalent attachment of the adaptor by electrostatic interactions with positively charged groups, such as amines, in the adaptor. More specifically, the positively charged amino acids repel the positively charged groups in the adaptor, push the adaptor down the barrel or channel of the pore and position it at or near residue 139 of SEQ ID NO: 2. This facilitates the covalent reaction between the adaptor and the pore. However, as discussed above, pores having positively charged amino acids located near the constriction of the barrel or channel may be prone to blocking.

The pore preferably has a ring of 4, 5, 6 or preferably 7 positively charged amino acids, such as arginine, lysine or histidine, located near the constriction of the barrel or channel. Each amino acid in the ring is typically provided by each of the subunits. In preferred embodiments, one or more of the seven subunits has a positively charged amino acid, such as arginine, lysine or histidine, at residue 113 of SEQ ID NO: 2. In more preferred embodiments, one or more of the seven subunits has an arginine residue at residue 113 of SEQ ID NO: 2. In even more preferred embodiments, all of the seven subunits have an arginine residue at residue 113 of SEQ ID NO: 2. Arginine can be introduced at residue 113 or residue 113 can be substituted with arginine (M113R). Preferred subunits having residue 113 of SEQ ID NO: 2 substituted with arginine (M113R) are shown in SEQ ID NOs: 4, 6, 8, 10, 12 and 14.

The subunits may be a naturally occurring variants which are expressed by an organism, for instance by a *Staphylococcus* bacterium. Variants also include non-naturally occurring variants produced by recombinant technology. Over the entire length of the amino acid sequence of SEQ ID NO: 2, a variant will preferably be at least 50% homologous to that sequence based on amino acid identity. More preferably, the subunit polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 200 or more, for example 230, 250, 270 or 280 or more, contiguous amino acids ("hard homology").

Amino acid substitutions may be made to the amino acid sequence of SEQ ID NO: 2 in addition to those discussed above, for example up to 1, 2, 3, 4, 5, 10, 20 or 30 substitutions. Conservative substitutions may be made, for example, according to Table 1 below.

TABLE 1

Conservative substitutions

| NON-AROMATIC | Non-polar | G A P |
| | | I L V |
| | Polar-uncharged | C S T M |
| | | N Q |
| | Polar-charged | D E |
| | | H K R |
| AROMATIC | | H F W Y |

Amino acids in the same block in the second column and preferably in the same line in the third column may be substituted for each other.

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include subunits made of fragments of SEQ ID NO: 2. Such fragments retain pore forming activity. Fragments may be at least 50, 100, 200 or 250 amino acids in length. Such fragments may be used to produce chimeric pores. A fragment preferably comprises the pore forming domain of SEQ ID NO: 2. Fragments must include residues 139 and 119, 121 or 135 of SEQ ID NO: 2.

Variants include chimeric proteins comprising fragments or portions of SEQ ID NO: 2. Chimeric protein pores may be formed from one or more subunits each comprising fragments or portions of SEQ ID NO: 2. The pore or channel part of a chimeric protein pore is typically formed by the fragments or portions of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention.

As discussed above, a variant is a subunit that has an amino acid sequence which varies from that of SEQ ID NO: 2 and which retains its ability to form a pore. A variant typically contains the regions of SEQ ID NO: 2 that are responsible for pore formation. The pore forming ability of α-HL, which contains a β-barrel, is provided by β-sheets in each subunit. A variant of SEQ ID NO: 2 typically comprises the regions in SEQ ID NO: 2 that form β-sheets. Amino acids 22 to 30, 35 to 44, 52 to 62, 67 to 71, 76 to 91, 98 to 103, 112 to 123, 137 to 148, 154 to 159, 165 to 172, 229 to 235, 243 to 261, 266 to 271, 285 to 286 and 291 to 293 of SEQ ID NO: 2 form β-sheets. One or more modifications can be made to the regions of SEQ ID NO: 2 that form β-sheets as long as the resulting variant retains its ability to form a pore. Specific modifications that can be made to the β-sheet regions of SEQ ID NO: 2 are discussed above.

A variant of SEQ ID NO: 2 preferably includes one or more modifications, such as substitutions, additions or deletions, within its α-helices and/or loop regions. Amino acids 2 to 6, 73 to 75, 207 to 209, 214 to 216 and 219 to 222 of SEQ ID NO: 2 form α-helices. Amino acids 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274 and 287 to 290 of SEQ ID NO: 2 form loops. Amino acids 1 and 294 are terminal amino acids.

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

One or more of the subunits may be modified for example by the addition of histidine or aspartic acid residues to assist their identification or purification or by the addition of a signal sequence to promote their secretion from a cell where the polypeptide does not naturally contain such a sequence.

The pore may be labelled with a revealing label. The revealing label may be any suitable label which allows the pore to be detected. Suitable labels include, but are not limited to fluorescent molecules, radioisotopes, e.g. $^{125}$I, $^{35}$S, enzymes, antibodies, antigens, polynucleotides and ligands such as biotin.

The pore may be derived from a pore producing organism, such as *Staphylococcus aureus*, or made synthetically or by recombinant means. For example, the pore may be synthesized by in vitro translation and transcription. The amino acid sequence of the pore may be modified to include non-naturally occurring amino acids or to increase the stability of the compound. When the pores are produced by synthetic means, such amino acids may be introduced during production. The pores may also be altered following either synthetic or recombinant production.

The pore may also be produced using D-amino acids. For instance, the pores may comprise a mixture of L-amino acids and D-amino acids. This is conventional in the art for producing such proteins or peptides.

The pore contains one or more specific modifications to facilitate positioning of the adaptor and optionally to facilitate covalent attachment. The pore may also contain other non-specific modifications as long as they do not interfere with the attachment and positioning of the adaptor. A number of non-specific side chain modifications are known in the art and may be made to the side chains of the pores. Such modifications include, for example, reductive alkylation of amino acids by reaction with an aldehyde followed by reduction with $NaBH_4$, amidination with methylacetimidate or acylation with acetic anhydride.

The pore can be produced using standard methods known in the art. Polynucleotide sequences encoding a pore or a pore subunit may be derived and replicated using standard methods in the art. Such sequences are discussed in more detail below. Polynucleotide sequences encoding a pore or a pore subunit may be expressed in a bacterial host cell using standard techniques in the art. The pore or pore subunit may be produced in a cell by in situ expression of the polypeptide from a recombinant expression vector. The expression vector optionally carries an inducible promoter to control the expression of the polypeptide.

A pore subunit may be produced in large scale following purification by any protein liquid chromatography system from pore producing organisms or after recombinant expression as described below. Typical protein liquid chromatography systems include FPLC, AKTA systems, the Bio-Cad system, the Bio-Rad BioLogic system and the Gilson HPLC system. The naturally occurring or recombinantly-produced pore or or pore subunit may then be inserted into a naturally occurring or artificial membrane for use in accordance with the invention. Methods for inserting pore into membranes are discussed below.

Any combination of seven of the subunits (i.e. variants of SEQ ID NO: 2) shown in SEQ ID NOs: 4, 6, 8, 10, 12 and 14 may be used to form a pore of the invention. Preferred pores comprise:

(a) six subunits of α-HL M113R/N139Q shown in SEQ ID NO: 8 and one subunit of α-HL M113R/N139Q/G119C-D8 shown in SEQ ID NO: 10; or (b) six subunits of α-HL M113R/N139Q shown in SEQ ID NO: 8 and one subunit of α-HL M113R/N139Q/N121C-D8 shown in SEQ ID NO: 12;

In pores (a) and (b), the subunits shown in SEQ ID NOs: 10, 12, 18, 22, 26, 30 and 34 may lack the octa-aspartate tail.

The most preferred pore of the invention comprises six subunits of α-HL M113R/N139Q shown in SEQ ID NO: 8 and one subunit of α-HL M113R/N139Q/L135C-D8 shown in SEQ ID NO: 14. In such a pore, the subunit shown in SEQ ID NO: 14 may lack the octa-aspartate tail.

Molecular Adaptor

The pores of the invention comprise a molecular adaptor that facilitates the interaction between the pore and the nucleotides or target nucleic acid sequence. The presence of the adaptor improves the host-guest chemistry of the pore and nucleotides. The principles of host-guest chemistry are well-known in the art. The adaptor has an effect on the physical or chemical properties of the pore that improves its interaction with nucleotides. The adaptor typically alters the charge of the barrel or channel of the pore or specifically interacts with or binds to nucleotides thereby facilitating their interaction with the pore.

The adaptor mediates the interaction between each individual nucleotide or each nucleotide is a target nucleic acid sequence and the pore. The nucleotides preferably reversibly bind to the pore via or in conjunction with the adaptor. The nucleotides most preferably reversibly bind to the pore via or in conjunction with the adaptor as they pass through the pore across the membrane. The nucleotides can also reversibly bind to the barrel or channel of the pore via or in conjunction with the adaptor as they pass through the pore across the membrane. The adaptor preferably constricts the barrel or channel so that it may interact with the nucleotides.

The adaptor is typically cyclic. The adaptor preferably has the same symmetry as the pore. The adaptor preferably has seven-fold symmetry since α-HL has seven subunits around a central axis that contribute 14 strands to a transmembrane β barrel.

The adaptor typically interacts with the nucleotide via host-guest chemistry. The adaptor is typically capable of interacting with the nucleotide. The adaptor comprises one or more chemical groups that are capable of interacting with the nucleotide. The one or more chemical groups preferably interact with the nucleotide by non-covalent interactions, such as hydrophobic interactions, hydrogen bonding, Van der Waal's forces, π-cation interactions and/or electrostatic forces. The one or more chemical groups that are capable of interacting with the nucleotide are preferably positively charged. The one or more chemical groups that are capable of interacting with the nucleotide are more preferably preferably comprise amino groups. The amino groups can be attached to primary, secondary or tertiary carbon atoms. The adaptor even more preferably comprises a ring of amino groups, such as a ring of 6, 7 or 8 amino groups. The adaptor most preferably comprises a ring of seven amino groups. A ring of protonated amino groups may interact with negatively charged phosphate groups in the nucleotide.

As discussed in more detail below, the correct positioning of the adaptor within the barrel or channel of the pore can be facilitated by host-guest chemistry between the adaptor and the pore. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, π-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore, particularly those introduced at and/or near residue 139 of SEQ ID NO: 2. This interaction of one or more chemical groups in the adaptor with one or more amino acids in the pore can be used to hold the adaptor in the correct positioning at or near residue 139 of SEQ ID NO: 2.

The amine groups that are capable of interacting with one or more amino acids in the pore may be the same or different as the amine groups that are capable of interacting with the nucleotide. As discussed above, the positively charged amine groups in the adaptor may interact electrostatically with positively charged amino acids in the barrel or channel of the pore, such as arginines at residue 113 of SEQ ID NO: 2 (M113R) if present. This interaction pushes the adaptor down the barrel or channel of the pore and thereby facilitates covalent attachment.

Any adaptor that that facilitates the interaction between the pore and the nucleotide can be used. Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, H-J. (1994) *J. Am. Chem. Soc.* 116, 6081-6088. The adaptor is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD). The guanidine group in $gu_7$-βCD has a much higher pKa than the primary amines in $am_7$-βCD and so it more positively charged. This $gu_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono(2-pyridyl)dithiopropanoyl-β-cyclodextrin ($am_6amPDP_1$-βCD).

Covalent Attachment

The adaptor is covalently attached to the pore. The adaptor can be covalently attached to the pore using any method known in the art. The adaptor may be attached directly to the pore. The adaptor is preferably attached to the pore using a bifunctional crosslinker. Suitable crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the adaptor is covalently attached to the bifunctional crosslinker before the adaptor/crosslinker complex is covalently attached to the pore but it is also possible to covalently attach the bifunctional crosslinker to the pore before the bifunctional crosslinker/pore complex is attached to the adaptor. Production of the pores of the invention is discussed in more detail below.

The site of covalent attachment is selected such that the adaptor is positioned at or near residue 139 of SEQ ID NO: 2. This facilitates interaction of the nucleotide with the pore and thereby allows detection of the nucleotide. It also ensures that the nucleotide affects the current flowing through the pore in a manner specific for that nucleotide.

The adaptor is positioned at residue 139 of SEQ ID NO: 2 if it is positioned in the barrel or channel of the pore in the same horizontal plane as residue 139 of SEQ ID NO: 2. The adaptor is positioned at residue 139 of SEQ ID NO: 2 if it is positioned at the same vertical position within the barrel or channel of the pore as residue 139 of SEQ ID NO: 2. The adaptor is positioned near residue 139 of SEQ. ID NO: 2 if it is positioned in the barrel or channel of the pore in the same horizontal plane as a residue that is near to residue 139 of SEQ ID NO: 2. The adaptor is positioned near residue 139 of SEQ ID NO: 2 if it is positioned at the same vertical position within the barrel or channel of the pore as a residue that is near to residue 139 of SEQ ID NO: 2. The adaptor is preferably positioned in a horizontal plane that is less than 5 ångströms, such as less than 3 or less than 2 ångströms, from the horizontal plane of residue 139 in SEQ ID NO: 2. The adaptor is more preferably positioned in the same horizontal plane as residue 117, 118, 119, 120, 121, 122, 123, 136, 137, 138, 139, 140, 141 or 142 of SEQ ID NO: 2.

The adaptor is typically covalently attached to the barrel or channel of the pore. The adaptor can be covalently attached at any site in the barrel or channel as long as the adaptor is positioned at or near residue 139 of SEQ ID NO: 2, facilitates interaction of the nucleotide with the pore and thereby allows detection of the nucleotide. The adaptor is typically covalently attached to an amino acid in the barrel or channel that is close to residue 139 of SEQ ID NO: 2. The adaptor is preferably attached to an amino acid in the pore that is near to the ring of residues formed by residue 139 of SEQ ID NO: 2 in each subunit. If the adaptor is covalently attached to an amino acid in the barrel or channel that is far from the ring of residues formed by residue 139 of SEQ ID NO: 2 in each subunit, a bifunctional crosslinker of suitable length may be used so that the adaptor is positioned at or near residue 139.

The adaptor is preferably attached to residue 119 or 121 of SEQ ID NO: 2 in one or more of the seven subunits. The adaptor is more preferably attached to residue 135 of SEQ ID NO: 2, in one or more of the seven subunits. Attaching the adaptor to residue 119, 121 or 135 positions the adaptor near to the ring of residues formed by residue 139 of SEQ ID NO: 2 in each subunit.

The pore is preferably modified by the introduction of one or more amino acids to facilitate the covalent attachment of the molecular adaptor with the bifunctional crosslinker. The barrel or channel of the pore is more preferably modified to facilitate the covalent attachment of the molecular adaptor with the bifunctional crosslinker. The pore may be modified using any method known in the art. One or more amino acids may be introduced into the same or different subunits of the pore. Any amino acid that is capable of forming a covalent bond, such as cysteine, can be introduced. The amino acid may be naturally occurring or non-naturally occurring. The one or more amino acids are preferably introduced by substitutions.

In preferred embodiments, residue 119, 121 or 135 of SEQ ID NO: 2 is modified in one or more of the seven subunits to facilitate covalent attachment. In more preferred embodiment, residue 119, 121 or 135 of SEQ ID NO: 2 modified in one of the seven subunits. Any of the subunit discussed above may be used to facilitate the covalent attachment of the molecular adaptor or the bifunctional crosslinker.

Positioning of the Adaptor

The adaptor is covalently attached to the pore in a position that allows the nucleotide to be detected using the pore. The adaptor is positioned such the nucleotide affects the current flowing through the pore in a manner specific for that nucleotide. The adaptor is positioned so this it improves the host-guest chemistry of the pore and nucleotide. The adaptor is positioned so that it affects the physical or chemical properties of the pore and improves its interaction with the nucleotide. The adaptor is typically positioned so that it forms a steric block to the flow of ions through the pore. If the adaptor is capable of specifically interacting with or binding to the nucleotide, the adaptor is positioned so that it specifically interacts with or binds to the nucleotide. The one or more chemical groups in the adaptor that interact with the nucleotide are preferably oriented away from the end of the pore through which the nucleotide enters. Such an orientation helps to draw the nucleotide through the barrel or channel of the pore. The groups are preferably amino groups. The end of the pore through which the nucleotide enters may be the cis end or the trans end. The end is preferably the cis end.

The covalent attachment may be designed so that the adaptor is correctly positioned. For instance, the site (e.g. amino acid) at which the adaptor is covalently attached to the pore may be designed so that the adaptor is correctly positioned and/or a bifunctional crosslinker may be used so that the adaptor is correctly positioned.

The pores of the invention are modified to facilitate positioning of the adaptor. As discussed above, one or more of the seven subunits preferably has glutamine at and/or near residue 139 of SEQ ID NO: 2. Glutamine at and/or near residue 139 is capable of interacting with chemical groups, such as hydroxyl groups, on the adaptor by hydrogen bonding and thereby facilitates the positioning of the adaptor within the barrel or channel of the pore. The pore may also include modifications at other positions, such as residue 113 of SEQ ID NO: 2, to facilitate positioning of the adaptor (see above).

Most preferably, the pore is modified to facilitate the covalent attachment and to facilitate the positioning of the adaptor. In such an embodiment, the spatial relationship between the site of covalent attachment and site(s) at which the pore is modified to facilitate the positioning of the adaptor is designed to ensure that the adaptor is held in the correct position. For instance, the adaptor is preferably attached to residue 135 of SEQ ID NO: 2 in one subunit to place it near to the ring of one or more glutamines formed by residue 139 of SEQ ID NO: 2 in each subunit. The one or more glutamines facilitate the positioning of the adaptor by hydrogen bonding.

Polynucleotides

The present invention also provides polynucleotide sequences which encode a subunit of α-HL having the sequence shown in SEQ ID NO: 2 or a variant thereof, wherein the subunit has a cysteine at residue 119, 121 or 135. The variant of SEQ ID NO: 2 may be any of those discussed above. The polynucleotide sequence preferably comprises the sequence shown in SEQ ID NO: 9, 11 or 13 or a sequence at least 50%, 60%, 70%, 80%, 90% or 95% homologous based on nucleotide identity to sequence of SEQ ID NO: 9, 11 or 13 over the entire sequence. There may be at least 80%, for example at least 85%, 90% or 95% nucleotide identity over a stretch of 600 or more, for example 700, 750, 850 or 900 or more, contiguous nucleotides ("hard homogly"). Homology may be calculated as described above. The polynucleotide sequence may comprise a sequence that differs from SEQ ID NO: 9, 11 or 13 on the basis of the degeneracy of the genetic code.

Polynucleotide sequences may be derived and replicated using standard methods in the art. Chromosomal DNA may be extracted from a pore producing organism, such as *Staphylococcus aureus*. The gene encoding the pore subunit may be amplified using PCR involving specific primers. The amplified sequence may then be incorporated into a recombinant replicable vector such as a cloning vector. The vector may be used to replicate the polynucleotide in a compatible host cell. Thus polynucleotide sequences encoding a pore subunit may be made by introducing a polynucleotide encoding a pore subunit into a replicable vector, introducing the vector into a compatible host cell, and growing the host cell under conditions which bring about replication of the vector. The vector may be recovered from the host cell. Suitable host cells for cloning of polynucleotides encoding a pore subunit are known in the art and described in more detail below.

The polynucleotide sequence encoding a pore subunit may be cloned into suitable expression vector. In an expression vector, the polynucleotide sequence encoding a pore subunit is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different pore subunit sequences may be introduced into the vector.

The expression vector may then be introduced into a suitable host cell. Thus, a pore subunit can be produced by inserting a polynucleotide sequence encoding a pore subunit into an expression vector, introducing the vector into a compatible bacterial host cell, and growing the host cell under conditions which bring about expression of the polynucleotide sequence encoding the pore subunit. The recombinantly-expressed pore subunit may self-assemble into a pore in the host cell membrane. Alternatively, the recombinant pore produced in this manner may be removed from the host cell and inserted into another membrane. When producing a heptameric pore comprising at least two different subunits, the different subunits may be expressed separately in different host cells as described above, removed from the host cells and assembled into a pore in a separate membrane, such as a rabbit cell membrane.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or λ$_L$ promoter is typically used.

The host cell typically expresses the pore subunit at a high level. Host cells transformed with a polynucleotide sequence encoding a pore subunit will be chosen to be compatible with the expression vector used to transform the cell. The host cell is typically bacterial and preferably *Escherichia coli*. Any cell with a λ DE3 lysogen, for example C41 (DE3), BL21 (DE3), JM109 (DE3), B834 (DE3), TUNER, Origami and Origami B, can express a vector comprising the T7 promoter.

Methods of Producing the Pores of the Invention

The invention also provides methods of producing the pores of the invention. The methods comprise covalently attaching to a pore a molecular adaptor that facilitates an interaction between the pore and a nucleotide. The adaptor can be covalently attached to the pore using any method known in the art.

Any of the pores, adaptors and bifunctional crosslinkers discussed above can be used in the method. The site of covalent attachment is selected as discussed above.

The adaptor is typically attached to the pore by adding an adaptor containing a bifunctional crosslinker, such as am$_6$amPDP$_1$-βCD, to a mutant α-HL pore containing at least one reactive amino acid, such as a cysteine. However, this method has a couple of drawbacks. The first is the reactivity of the amino acid, such as cysteine, which deteriorates over time via oxidation or reaction with other species in solution. The second is the time taken for the reaction between the crosslinker and the pore to occur. These drawbacks can lead to difficulties, particularly if a single pore is being used. For instance, if a single α-HL pore containing a single cysteine mutation is inserted into a lipid membrane and an adaptor containing a crosslinker is added to the electrophysiology chamber, the adaptor molecules enter and exit the pore until one reacts with the cysteine. If the cysteine becomes inactivated, then a reaction will not be observed no matter how many adaptor molecules enter the pore. Inactivation of the reactive amino acid(s) in the pore can reduced by improving the storage conditions, for instance by removing oxygen, by the addition of stabilisers, such as reducing agents (e.g. dithiothreitol, DTT), by chemical protection of the cysteine followed by activation prior to use or by chemical attachment of the adaptor prior to storage.

In a preferred embodiment, the pore to which the adaptor is to be attached comprises a protective leaving group and the method comprises displacing the leaving group from the pore. The protective leaving group is used to protect the one or more reactive amino acids in the pore. The protective leaving group is preferably used to protect one or more cysteine residues in the pore. The protective leaving group is displaced by reaction with a reactive group on the adaptor, which may contain a crosslinker.

In a more preferred embodiment, the pore comprises a protective leaving group on one or more reactive cysteines, such as the cysteine at residue 119, 121 or 135 of SEQ ID NO: 2 in the variants discussed above, and is reacted with an adaptor which contains a crosslinker having a reactive —SH group. The —SH group on the crosslinker displaces the protective leaving group attached to the pore and a pore having an adaptor covalently attached thereto is produced.

Attaching a protective leaving group to the one or more reactive amino acids in the pore and having the reactive group on the adaptors greatly improves the method of the invention, particularly when using a single pore. For instance, when attaching a reactive adaptor molecule to a single pore having a protective group, the adaptor molecules vastly outnumber the single pore. As a result, even if some of the reactive adaptor molecules are inactivated, at least one is likely to remain reactive and displace the protective leaving group from the pore.

As electrophysiology experiments can be quite difficult, it is preferable to limit the setup time of the experiment and thereby optimise the time for data acquisition. It is therefore preferred that the adapter is attached to the pore prior to bilayer insertion. This not only increases the ease of the electrophysiology experiment, but also improves the shelf-life of the pore.

Suitable protective leaving groups are known in the art. Examples include, but are not limited to, 5,5'-dithiobis(2-nitrobenzoic acid) (DTNB) and 2,2'-dithiodipyridine.

The adaptor may be attached to one or more subunits of the pore before they oligomerise to form the pore. Large adaptor molecules may reduce the efficiency of oligomerisation or may prevent the formation of a pore entirely. However, a benefit of this approach is that the monomer-adapter species is easy to separate from the unmodified monomer due to the relatively large change in either charge or mass. Additionally, as the two species can be separated prior to oligomerisation, there is a high probability that the final nanopore will contain the covalently attached adapter.

The adaptor may be attached to one or more subunits of the pore as they oligomerise. This can be done using lipid vesicles loaded with the adaptor. This approach benefits from localising the adaptor away from the subunits. Additionally, when the oligomerisation takes place, the pore is protected from the adaptor by the vesicle bilayer. The loaded vesicles can then be run through an SDS page gel procedure to extract the pore from the membranes and remove any unreacted adaptor.

The adaptor may be attached to an oligomerised pore. The pore is produced using the standard techniques discussed above. The adaptor is added after the heptamer is formed. This can be done prior to, or immediately after, the final purification, such as using an SDS page gel. This embodiment requires the fewest changes to the standard pore production protocol and results in a high proportion of pores of the invention. However, tests have shown that the yield of pores produced using this embodiment is much lower than expected. This may be due to the adaptor being present in sufficient quantities to disrupt the surfactant in the protein sample, resulting in protein aggregation or it may be due to the hydrophobic crosslinker, if present, associating with β-barrel of the pore and preventing efficient pore insertion.

The methods also comprise determining whether or not the adaptor is attached to the pore in a position that allows the nucleotide to be detected using the pore. This involves determining whether or not the pore can be used to determine the presence or absence of the nucleotide. This can be done as described in more detail below. If the presence or absence of the nucleotide can be determined, the adaptor is in the correct position and a pore of the invention has been produced. If the presence or absence of the nucleotide cannot be determined, the adaptor is likely to be in an incorrect position and a pore of the invention has not been produced.

Methods of Identifying an Individual Nucleotide

The present invention also provides methods of identifying an individual nucleotide. The methods comprise contacting the nucleotide with a pore of the invention so that the nucleotide interacts with the pore and measuring the current passing through the pore during the interaction and thereby determining the identity of the nucleotide. The invention therefore involves stochastic sensing of an individual nucleotide. Any of the pores of the invention can be used.

The nucleotide is present if the current flows through the pore in a manner specific for the nucleotide (i.e. if a distinctive current associated with the nucleotide is detected flowing through the pore). The nucleotide is absent if the current does not flow through the pore in a manner specific for the nucleotide.

The invention can be used to differentiate nucleotides of similar structure on the basis of the different effects they have on the current passing through a pore. Individual nucleotides can be identified at the single molecule level from their current amplitude when they interact with the pore. The invention can also be used to determine whether or not a particular nucleotide is present in a sample. The invention can also be used to measure the concentration of a particular nucleotide in a sample.

The methods may be carried out using any suitable membrane/pore system in which a pore of the invention is inserted into a membrane. The methods are typically carried out using (i) an artificial membrane comprising a pore of the invention, (ii) an isolated, naturally occurring membrane comprising a pore of the invention, or (iii) a cell expressing a pore that has been modified in accordance with the invention. The methods are preferably carried out using an artificial membrane. The membrane may comprise other transmembrane and/or intramembrane proteins as well as other molecules in addition to the pore of the invention.

The membrane forms a barrier to the flow of ions, nucleotides and nucleic acids. The membrane is preferably a lipid bilayer. Lipid bilayers suitable for use in accordance with the invention can be made using methods known in the art. For example, lipid bilayer membranes can be formed using the method of Montal and Mueller (1972). Lipid bilayers can also be formed using the method described in International Application No. PCT/GB08/000563.

The method of the invention may be carried out using lipid bilayers formed from any membrane lipid including, but not limited to, phospholipids, glycolipids, cholesterol and mixtures thereof. Any of the lipids described in International Application No. PCT/GB08/000563 may be used.

Methods are known in the art for inserting pores into membranes, such as lipid bilayers. For example, the pore may be suspended in a purified form in a solution containing a lipid bilayer such that it diffuses to the lipid bilayer and is inserted by binding to the lipid bilayer and assembling into a functional state. Alternatively, the pore may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

The methods of the invention are typically carried out in vitro.

Individual Nucleotide

An individual nucleotide is a single nucleotide. An individual nucleotide is one which is not bound to another nucleotide or nucleic acid by a nucleotide bond. A nucleotide bond involves one of the phosphate groups of a nucleotide being bound to the sugar group of another nucleotide. An individual nucleotide is typically one which is not bound by a nucleotide bond to another nucleic acid sequence of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand.

The methods of the invention may be used to identify any nucleotide. The nucleotide can be naturally occurring or artificial. A nucleotide typically contains a nucleobase, a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

Suitable nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotide is preferably AMP, TMP, GMP, UMP, dAMP, dTMP, dGMP or dCMP.

The nucleotide may be derived from the digestion of a nucleic acid sequence such as ribonucleic acid (RNA) or deoxyribonucleic acid. Nucleic acid sequences can be digested using any method known in the art. Suitable methods include, but are not limited to, those using enzymes or catalysts. Catalytic digestion of nucleic acids is disclosed in Deck et al., Inorg. Chem., 2002; 41: 669-677.

Individual nucleotides from a single nucleic acid sequence may be contacted with the pore in a sequential manner in order to sequence the whole or part of the nucleic acid. Sequencing nucleic acids in accordance with the second embodiment of the invention is discussed in more detail below.

The nucleotide is typically unmodified, such as when the nucleotide is derived from the digestion of a nucleic acid sequence. Alternatively, the nucleotide may be modified or damaged. The nucleotide is typically methylated or oxidised. The nucleotide may be labelled with a revealing label. The revealing label may be any suitable label which allows the nucleotide to be detected. Suitable labels include fluorescent molecules, radioisotopes, e.g. $^{125}$I, $^{35}$S, and linkers such as biotin.

The nucleotide is typically present in any suitable biological sample. Suitable biological samples are discussed above.

Interaction Between the Pore and Nucleotide

The nucleotide may be contacted with the pore on either side of the membrane. The nucleotide may be introduced to the pore on either side of the membrane. The nucleotide may be contacted with the side of the membrane that allows the nucleotide to pass through the pore to the other side of the membrane. For example, the nucleotide is contacted with an end of the pore, which in its native environment allows the entry of ions or small molecules, such as nucleotides, into the barrel or channel of the pore such that the nucleotide may pass through the pore. In such cases, the nucleotide interacts with the pore and/or adaptor as it passes across the membrane through the barrel or channel of the pore. Alternatively, the nucleotide may be contacted with the side of the membrane that allows the nucleotide to interact with the pore via or in conjunction with the adaptor, dissociate from the pore and remain on the same side of the membrane. The present invention provides pores in which the position of the adaptor is fixed. As a result, the nucleotide is preferably contacted with the end of the pore which allows the adaptor to interact with the nucleotide.

The nucleotide may interact with the pore in any manner and at any site. As discussed above, the nucleotide preferably reversibly binds to the pore via or in conjunction with the adaptor. The nucleotide most preferably reversibly binds to the pore via or in conjunction with the adaptor as it passes through the pore across the membrane. The nucleotide can also reversibly bind to the barrel or channel of the pore via or in conjunction with the adaptor as it passes through the pore across the membrane.

During the interaction between the nucleotide and the pore, the nucleotide affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to identify a particular nucleotide in the sample or determine whether a particular nucleotide is present in the sample. The frequency at which the current flowing through the pore is affected in a manner indicative of a particular nucleotide can be used to determine the concentration of that nucleotide in the sample. The ratio of different nucleotides within a sample can also be calculated. For instance, the ratio of dCMP to methyl-dCMP can be calculated.

Apparatus

The methods may be carried out using any apparatus that is suitable for investigating a membrane/pore system in which a pore of the invention is inserted into a membrane. The method may be carried out using any apparatus that is suitable for stochastic sensing. For example, the apparatus comprises a chamber comprising an aqueous solution and a barrier that separates the chamber into two sections. The barrier has an aperture in which the membrane containing the pore is formed. The nucleotide may be contacted with the pore by introducing the nucleotide into the chamber. The nucleotide may be introduced into either of the two sections of the chamber.

The methods may be carried out using the apparatus described in International Application No. PCT/GB08/000562.

The methods of the invention involve measuring the current passing through the pore during interaction with the nucleotide. Therefore the apparatus also comprises an electrical circuit capable of applying a potential and measuring an electrical signal across the membrane and pore. The methods may be carried out using a patch clamp or a voltage clamp. The methods preferably involve the use of a voltage clamp.

Sample

The nucleotide is present in any suitable sample. The invention is typically carried out on a sample that is known to contain or suspected to contain the nucleotide. The invention may be carried out on a sample that contains one or more nucleotides whose identity is unknown. Alternatively, the invention may be carried out on a sample to confirm the identity of one or more nucleotides whose presence in the sample is known or expected.

The sample may be a biological sample. The invention may be carried out in vitro on a sample obtained from or extracted from any organism or microorganism. The organism or microorganism is typically prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Conditions

The methods of the invention involve the measuring of a current passing through the pore during interaction with the nucleotide. Suitable conditions for measuring ionic currents through transmembrane protein pores are known in the art and disclosed in the Example. The method is carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 120 mV to 170 mV. It is possible to increase discrimination between different nucleotides by a pore of the invention by using an increased applied potential.

The methods are typically carried out in the presence of any alkali metal chloride salt. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration is typically from 0.1 to 2.5M, from 0.3 to 1.9M, from 0.5 to 1.8M, from 0.7 to 1.7M, from 0.9 to 1.6M or from 1M to 1.4M. The salt concentration is preferably from 150 to 500 mM. High salt concentrations provide a high signal to noise ratio and allow for currents indicative of the presence of a nucleotide to be identified against the background of normal current fluctuations. Lower salt concentrations must be used if nucleotide detection is carried out in the presence of an enzyme, such as when sequencing nucleic acids. This is discussed in more detail below.

The methods are typically carried out in the presence of a buffer. In the exemplary apparatus discussed above, the buffer is present in the aqueous solution in the chamber. Any buffer may be used in the method of the invention. One suitable buffer is Tris-HCl buffer. The methods are typically carried out at a pH of from 4.0 to 10.0, from 4.5 to 9.5, from 5.0 to 9.0, from 5.5 to 8.8, from 6.0 to 8.7 or from 7.0 to 8.8 or 7.5 to 8.5. The pH used is preferably about 7.5.

The methods are typically carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods may be carried out at room temperature. The methods are preferably carried out at a temperature that supports enzyme function, such as about 37° C. Good nucleotide discrimination can be achieved at low salt concentrations if the temperature is increased.

Methods of Sequencing Nucleic Acids

The present invention also provides methods of sequencing a target nucleic acid sequence. In one embodiment, the method comprises (a) digesting an individual nucleotide from one end of the target sequence using an exonuclease; (b) contacting the nucleotide with a pore of the invention so that the nucleotide interacts with the pore; (c) measuring the current passing through the pore during the interaction and thereby determining the identity of the nucleotide; and (d) repeating steps (a) to (c) at the same end of the target sequence and thereby determining the sequence of the target sequence. Hence, the method involves stochastic sensing of each single nucleotide of a nucleic acid sequence in a successive manner in order to sequence the nucleic acid. Steps (b) and (c) of this method are generally identical to the steps carried out in the method of identifying nucleotides discussed above.

The pores of the invention are particularly suited to these methods. In order to effectively sequence the nucleic acid, it is important to ensure that every nucleotide in the nucleic acid is identified in a successive manner. The fixed nature of the adaptor in a pore of the invention means that a distinctive current will flow through the pore whenever each successive nucleotide interacts with the pore.

The whole or only part of the target nucleic acid sequence may be sequenced using this method. The nucleic acid sequence can be any length. For example, the nucleic acid sequence can be at least 10, at least 50, at least 100, at least 150, at least 200, at least 250, at least 300, at least 400 or at least 500 nucleotides in length. The nucleic acid can be naturally occurring or artificial. For instance, the method may be used to verify the sequence of a manufactured oligonucleotide. The methods are typically carried out in vitro.

All of the discussion above concerning detecting nucleotides, and in particular concerning the pores, membranes, apparatus and conditions that may be used, equally applies to these methods. The nucleic acid is typically present in any biological sample as discussed above.

Exonuclease

In one embodiment, the method of sequencing a target nucleic acid sequence involves contacting the target sequence with an exonuclease, such as deoxyribonuclease, to release individual nucleotides from one end of the nucleic acid. Exonucleases are enzymes that typically latch onto one end of a nucleic acid and digest the sequence one nucleotide at a time from that end. The exonuclease can digest the nucleic acid in the 5' to 3' direction or 3' to 5' direction. The end of the nucleic acid to which the exonuclease binds is typically determined through the choice of enzyme used and/or using methods known in the art. Hydroxyl groups or cap structures at either end of the nucleic acid sequence may typically be used to prevent or facilitate the binding of the exonuclease to a particular end of the nucleic acid sequence.

Any exonuclease enzyme may be used in the method. Preferred enzymes for use in the method include exonuclease III enzyme from E. coli (SEQ ID NO: 16), exonuclease I from E. coli (SEQ ID NO: 18), bacteriophage lambda exonuclease (SEQ ID NO: 20) and variants thereof. Three identical subunits of SEQ ID NO: 20 interact to form a trimer exonuclease. Variants are polypeptides which have an amino acid sequence which vary from that of SEQ ID NO: 16, 18 or 20 and which retain exonuclease activity. The variants may vary from SEQ ID NO: 16, 18 or 20 in the same manner and to the same extent as discussed for variants of SEQ ID NO: 2 above. A variant preferably comprises the domains responsible for binding to the nucleic acid and for digesting the nucleic acid (catalytic domain). A variant preferably has an increased or reduced rate of enzyme activity as required and/or higher salt tolerance compared to the wild-type enzyme. The exonuclease may be produced using any of the methods discussed above for the production of pores.

The method involves contacting the nucleic acid sequence with the exonuclease so that the nucleotides are digested from the end of the nucleic acid at a rate that allows identification of each individual nucleotide as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The exonuclease is preferably covalently attached to the pore. Methods for covalently attaching the exonuclease to the pore are well known in the art. The method preferably involves the use of a pore containing one or more of the constructs, which comprise the sequence shown in SEQ ID NO: 2 or a variant thereof and an exonuclease, described in a co-pending International application claiming priority from U.S. Application No. 61/078,695 and being filed simultaneously with this application [J A Kemp & Co Ref: N.104404A; Oxford Nanolabs Ref: ONL IP 005]. If the method involves the use of a pore comprising a construct disclosed in the co-pending application, the target nucleic acid sequence is typically contacted with the side of the membrane on which the enzyme is attached to the pore.

The rate at which the exonuclease functions is typically slower than the optimal rate of a wild-type exonuclease. A suitable rate of activity of the exonuclease in the method of sequencing involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used in accordance with the invention.

The activity of exonucleases is typically pH dependent such that their activity falls as pH is reduced. Hence, the method of the second embodiment is typically carried out at a pH of from 7.5 to 8.0 or from 7.7 to 8.0. The pH used is preferably about 7.5.

The activity of exonucleases is typically dependent on the presence of certain metal ions, such as magnesium. Hence, a suitable rate of activity of an exonuclease enzyme can be achieved by reducing the concentration of magnesium ions or replacing the magnesium ions with different metal ions, such as manganese ions.

The rate of activity of exonucleases typically falls as salt concentration rises. The exonucleases will not work at high salt concentrations. The pores of the invention are capable of discriminating nucleotides at low salt concentrations. The sequencing method is typically carried out using a salt concentration of from 0.15 to 0.8M (150 mM to 800 mM). Good nucleotide discrimination at these low salt concentrations can be achieved by carrying out the method at temperatures above room temperature, such as from 30° C. to 40° C. and preferably at about 37° C.

In addition to increasing the solution temperature, there are a number of other strategies that can be employed to increase the conductance of the solution, while maintaining conditions that are suitable for enzyme activity. One such strategy is to use the lipid bilayer to divide two different concentrations of salt solution, a low salt concentration of salt on the enzyme side and a higher concentration on the opposite side. One example of this approach is to use 200 mM of KCl on the cis side of the membrane and 500 mM KCl in the trans chamber. At these conditions, the conductance through the pore is expected to be roughly equivalent to 400 mM KCl under normal conditions, and the enzyme only experiences 200 mM if placed on the cis side. Another possible benefit of using asymmetric salt conditions is the osmotic gradient induced across the pore. This net flow of water could be used to pull nucleotides into the pore for detection. A similar effect can be achieved using a neutral osmolyte, such as sucrose, glycerol or PEG. Another possibility is to use a solution with relatively low levels of KCl and rely on an additional charge carrying species that is less disruptive to enzyme activity.

Kits

The present invention also provides kits for producing a pore of the invention. The kits comprise seven polynucleotides each of which encode a subunit of α-HL having the sequence shown in SEQ ID NO: 2 or a variant thereof. One or more of the seven subunits has glutamine at residue 139 of SEQ ID NO: 2. At least one, or preferably only one, of the subunits has cysteine at residue 119, 121 or 135. Preferred polynucleotides encoding a subunit having glutamine at residue 139 of SEQ ID NO: 2 are shown in SEQ ID NOs: 7, 9, 11 and 13. The polynucleotides encoding the subunit having a cysteine at residue 119, 121 or 135 may be any of the polynucleotides of the invention, particularly those shown in SEQ ID NOs: 9, 11 and 13.

The kit preferably comprises six polynucleotides comprising the sequence shown in SEQ ID NO: 7 and one polynucleotide comprising the sequence shown in SEQ ID NO: 9, 11 or 13. The kit most preferably comprises six polynucleotides comprising the sequence shown in SEQ ID NO: 7 and one polynucleotide comprising the sequence shown in SEQ ID NO: 13.

The present invention also provides kits that may be used to carry out the method of sequencing a target nucleic acid sequence. The kits are therefore suitable for sequencing nucleic acids. The kits comprise a pore of the invention and an exonuclease.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotide sequences, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Example illustrates the invention:

EXAMPLE

1. Materials and Methods 1.1 Chemicals

Reagents were obtained as follows: 1,2-diphytanoyl-sn-glycero-3-phosphocholine (Avanti Polar Lipids); pentane (Sigma-Aldrich); hexadecane (99+%, Sigma-Aldrich); heptakis(6-deoxy-6-amino)-β-cyclodextrin.7HCl (am$_7$-βCD, >99%, CYCLOLAB, Budapest, Hungary); 2'-deoxyguanosine 5'-monophosphate sodium salt (99%, Acros); 2'-deoxycytosine 5'-monophosphate disodium salt (>95%, Fluka); 2'-deoxythymidine 5'-monophosphate disodium salt (>97%, Fluka); 2'-deoxyadenosine 5'-monophosphate disodium salt (>95%, Fluka); uridine 5'-monophosphate disodium salt (99%, Fluka); cytosine 5'-monophosphate (free acid>98%, Fluka); adenosine 5'-monophosphate (free acid 99%, Acros); guanosine 5'-monophosphate disodium salt (97%, Acros); 5-methylcytosine (USB Europe), Trizma base (99.9%, Sigma-Aldrich); concentrated HCl (analytical reagent grade, Fisher Scientific); and potassium chloride (99%, Sigma-Aldrich).

1.2 Synthesis of Reactive Cyclodextrin

The structures of the heptakis(6-deoxy-6-amino)-β-cyclodextrin (am$_7$-βCD), am$_6$amPDP$_1$-βCD and amPDP$_1$-βCD used in this work are shown in FIG. 1. The am$_6$-amPDP$_1$-βCD was synthesised as follows: heptakis(6-deoxy-6-amino)-β-cyclodextrin. 7HCl (am$_7$βCD, 60 mg, 0.053 mmol) was dissolved in de-ionised water (2.5 mL). This was then added to a solution of 3-(2-pyridyldithio)propionic acid N-hydroxysuccinimide (SPDP, 3.13 mg, 0.01 mmol) dissolved in ethanol (2.5 mL). The resultant solution was stirred at room temperature for 24 hours. The solvent was then removed to yield a mixture of products; the unmodified cyclodextrin (am$_7$βCD), the desired mono-substituted derivative (am$_6$-amPDP$_1$-βCD), and a small quantity of poly-substituted cyclodextrins (e.g. am$_5$-amPDP$_2$-βCD). The product mixture can be used directly in the electrophysiology experiments, or the mono-substituted product purified via reverse phase preparative HPLC.

1.3 Design of Adapter for Covalent Attachment

The high affinity adapter used in this work, am$_7$-βCD, contains seven primary amines on the primary hydroxyl face, one on each of the sugar rings. The presence of these charged groups is known to be crucial for base detection (see below). The desired compound for base detection should have a single reactive site for attachment to the pore and also contain the primary amines necessary for base detection.

In this work, the bifunctional crosslinker, succinimidyl 3-(2-pyridyldithio)propionate (SPDP), was used to link am$_7$-βCD to a cysteine residue genetically engineered into the α-HL protein pore. This linker was reacted with a cyclodextrin molecule containing seven primary amines (am$_7$-βCD). The concentrations of each species were chosen to promote the formation for the final species where only one linker molecule was attached to a single amino-cyclodextrin, resulting in the synthesis of the am$_6$amPDP$_1$-βCD adapter.

1.4 Construction of α-HL Mutants

HL-M113R/N139Q (SEQ ID NO: 5) and HL-M113R/N139Q/L135C-D8 (SEQ ID NO: 7) constructs were assembled in the pT7-SC1 expression vector (Cheley, S., Malghani, M. S., Song, L., Hobaugh, M., Gouaux, J. E., Yang, J., and Bayley, H., Protein Eng., (1997), 10 (12), 1433-1443) and verified by DNA sequencing of the entire α-HL inserts. Genes encoding the mutants were generated by PCR mutagenesis and ligation-free in vivo recombination as described elsewhere (Jones, D. H. (1995) PCR mutagenesis and recombination in vivo. In PCR primer: a laboratory manual. In: Dveksler, C. W. D. a. G. S. (ed). Cold Spring Harbor Laboratory Press, Cold Spring Harbor, N.Y.; and Howorka, S., and Bayley, H., Biotechniques, (1998), 25 (5), 764-766, 768, 770 passim).

1.5 Coupled in Vitro Transcription and Translation (IVTT)

Proteins were generated by coupled in vitro transcription and translation (IVTT) by using an E. coli T7-S30 extract system for circular DNA (Promega, no. L1130). The complete amino acid mixture (1 mM) minus cysteine and the complete amino acid mixture (1 mM) minus methionine, supplied in the kit, were mixed in equal volumes to obtain the working amino acid solution required to generate high concentrations of the proteins. The amino acids (5.0 µl) were mixed with premix solution (20 µl), [$^{35}$S]L-methionine (1 µl, MP Biomedicals, no. 51001H, 1175 Ci/mmol, 10 mCi/ml), rifampicin (1 µl, 0.8 mg/ml), plasmid DNA (8 µl, 400 ng/µl) and T7 S30 extract (15 µl) (Cheley, S., Malghani, M. S., Song, L., Hobaugh, M., Gouaux, J. E., Yang, J., and Bayley, H., Protein Eng, (1997), 10 (12), 1433-1443). Synthesis was carried out for 1.5 hours at 37° C. to produce 500 of radiolabeled IVTT protein.

1.6 Generation of Heterooligomers for Electrophysiology Analysis

Proteins of HL-M113R/N139Q (100 µl; SEQ ID NO: 6) and HL-M113R/N139Q/L135C-D8 (25 µl; SEQ ID NO: 6) were generated by IVTT as described above. The negative charge of the "D8 tail" of the HL-M113R/N139Q/L135C-D8 protein (SEQ ID NO: 8) was expected to change the electrophoretic mobility of the assembled pore allowing the separation of hetero-heptamers.

Protein samples were centrifuged at 25,000 g for 10 minutes to separate insoluble debris of IVTT reactions. The two supernatants were mixed together with rabbit red blood cell membranes (10 µl, 2.5 mg proteins/ml), added DTT to a final concentration of 2 mM and incubated for 1 hour at 37° C. After the incubation, reaction mixture was centrifuged at 25,000 g for 10 minutes and discarded the supernatant. Membrane pellet was washed by resuspending in 200 µl MBSA (10 mM MOPS, 150 mM NaCl, pH 7.4 containing 1 mg/mL bovine serum albumin) and centrifuging again at 25,000 g for 10 minutes. After discarding the supernatant, membrane pellet was dissolved in 75 µl of 1× Laemmli sample buffer.

Entire sample was loaded into a single well of a 5% SDS-polyacrylamide gel and electrophoresed for approximately 18 hours at 50 V. Gel was then vacuum-dried onto a Whatman 3 mm filter paper at 50° C. for about three hours and exposed to an X-ray film for two hrs. The negative charge of the "D8 tail" of the HL-M113R/N139Q/L135C-D8 protein (SEQ ID NO: 8) changes the electrophoretic mobility of the assembled pore allowing the separation of hetero-heptamers (Howorka, S., and Bayley, H., Biotechniques, (1998), 25 (5), 764-766, 768, 770 passim). The oligomer band containing HL-(M113R/N139Q)$_6$(M113R/N139Q/L135C-D8)$_1$ was excised from the gel using the autoradiogram as a template. Gel slice was then rehydrated in 300 µl TE buffer (10 mM Tris, 1 mM EDTA, pH 8.0) containing 2 mM DTT. After removing the Whatman filter paper slice, gel piece was crushed using a sterile pestle. Oligomer protein was separated from gel debris by centrifuging through 0.2 µm cellulose acetate spin filters (catalogue no. 7016-024, microfilterfuge tube, Rainin) at 25,000 g for 30 min. Filtrate was stored in aliquots at −80° C.

1.7 Single Channel Recordings

Single channel recordings were obtained using standard methods previously published in the scientific literature. In short, a bilayer of 1,2-diphytanoyl-sn-glycero-3-phosphocholine (Avanti Polar Lipids) was formed on an aperture 60-150 µm in diameter in a Teflon film (25 µm thickness from Goodfellow, Malvern, Pa.) that divided a planar bilayer chamber into two compartments, cis and trans. Both compartments contained 1 mL of buffer. Unless otherwise stated, both hemolysin mutants and dNMP (or rNMP) were added to the cis compartment, which was connected to ground. The am$_7$-βCD or am$_6$amPDP$_1$-βCD was added to the trans compartment, which was connected to the head-stage of the amplifier. Unless stated otherwise, experiments with dNMP were carried out in 25 mM Tris.HCl, 800 mM KCl pH 7.5, at 22° C. Fresh aliquots of nucleotide stock solutions were used each day.

1.8 Data Analysis and Acquisition

Single channel recordings were collected with a patch clamp amplifier (Axopatch 200B; Axon instruments, Foster City, Calif.), low pass filtered with a built-in 4-pole Bessel filter at 10 kHz, and sampled at 20 kHz by a PC equipped with a Digidata 1440A A/D converter (Axon instruments) running ClampEx 10 software (Molecular Devices).

Event histograms were constructed using the following procedure:
1) Two adjacent WT point windows were passed through the raw data (20 kHz sample rate, 10 kHz Bessel filtered).
2) The T-statistic (a measure of the statistical difference between two populations) between windows was calculated at each point.
3) Steps were identified by detecting peaks of width PT in the T-statistic exceeding a given threshold TT.
4) The data between steps was averaged to determine the mean current and duration of the event.
5) Histograms of the mean event current were plotted. An event was defined as "in limits" if the mean of the previous event was between set values LCD and UCD and if the duration was greater than N data points.

Typical values for event detection, producing a 4-nucleoside monophosphate histogram were WT=8, PT=3, TT=20, N=8, with LCD and UCD corresponding to the limits of the cyclodextrin level.

Multiple Gaussian fitting was performed on the event histograms by iterating mean, standard deviation and amplitude fits for the appropriate number of peaks starting with suitable initial parameters.

Gaussian overlaps were calculated by normalizing the product of two adjacent fit peaks to the sum of the peak areas. Overlaps ranged between 0 (no overlap) and 0.5 (identical distributions). Normalised overlaps were calculated by first dividing each Gaussian distribution by its area.

2. Results

2.1 Importance of the N139Q Position

Two different mutants were compared. The first was a HL-(M113R)$_7$ mutant in the RL2 background. In other words, the first mutant was generated starting from an RL2 construct. It contained seven of the subunits shown in SEQ ID NO: 4.

RL2 is the product of a semisynthetic gene that was devised to permit cassette mutagenesis of the sequence encoding the transmembrane β-barrel (Cheley, S., Braha, O., Lu, X., Conlan, S., and Bayley, H. (1999) *Protein Sci.* 8, 1257-1267). It contains six silent restriction sites and five altered amino acids in the encoded polypeptide sequence (K8A, V124L, G130S, N139Q and I142L). D8RL2 is RL2 with an octa-aspartate tail. With the exception of the K8A mutation, all of the changes were made to have minimal effects on the behaviour of the protein, examples of this are; the valine to leucine and the asparagine to glutamine mutations (introducing an addition methylene group), and the isoleucine to leucine mutation (changing the position of the methyl group).

The second was a HL-(M113R)$_7$ mutant based on wild-type HL. In other words, the second mutant was generated from a wild-type α-HL construct and did not contain the five altered amino acids of RL2. It contained seven of the subunits shown in SEQ ID NO: 6.

2.2 Proposed Position of the am$_7$-βCD

Figure 6:
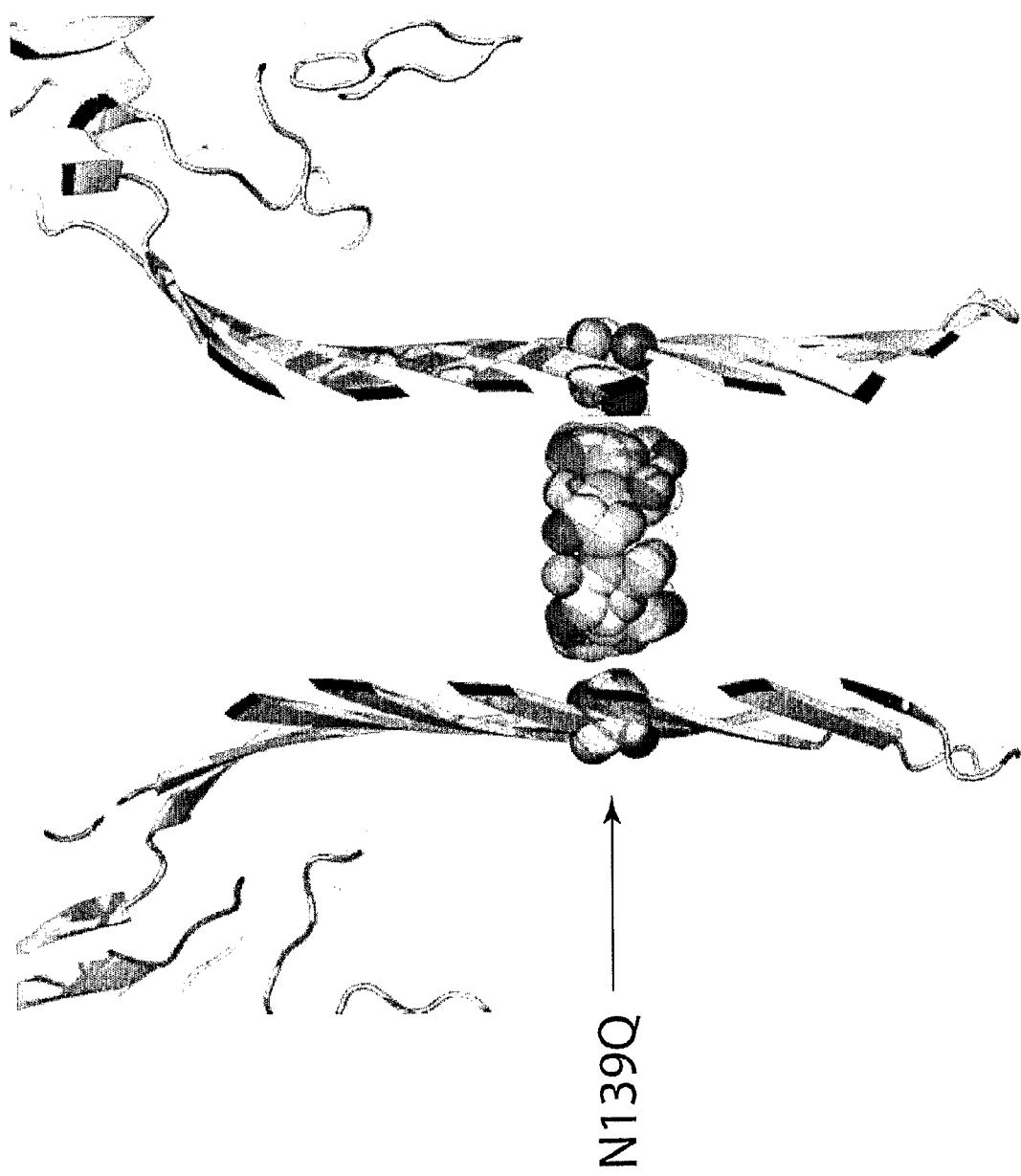
FIG. 6 shows the proposed cyclodextrin position at residue 139 of αHL.

We postulated that the cyclodextrin resides at a low position within the β-barrel, near to the 139 position, stabilised by the glutamine groups (FIG. 6). Realising the importance of the N139Q mutation is key to understanding the mechanism for base discrimination and designing the improved construct for improved and continuous base detection.

To test this hypothesis, a series of mutants were designed and produced to attach the reactive am$_7$-βCD at a range of positions within the β-barrel. A hetero-heptamer was formed by creating two different monomer units, one with a reactive cysteine and one lacking the cysteine group. The monomers were mixed and oligomerised to the heptameric protein pore. These were then separated by stoichiometry to ensure that only one cysteine modified monomer unit was present in any heptameric protein pore, allowing precise control of the attachment position.

Figure 7:
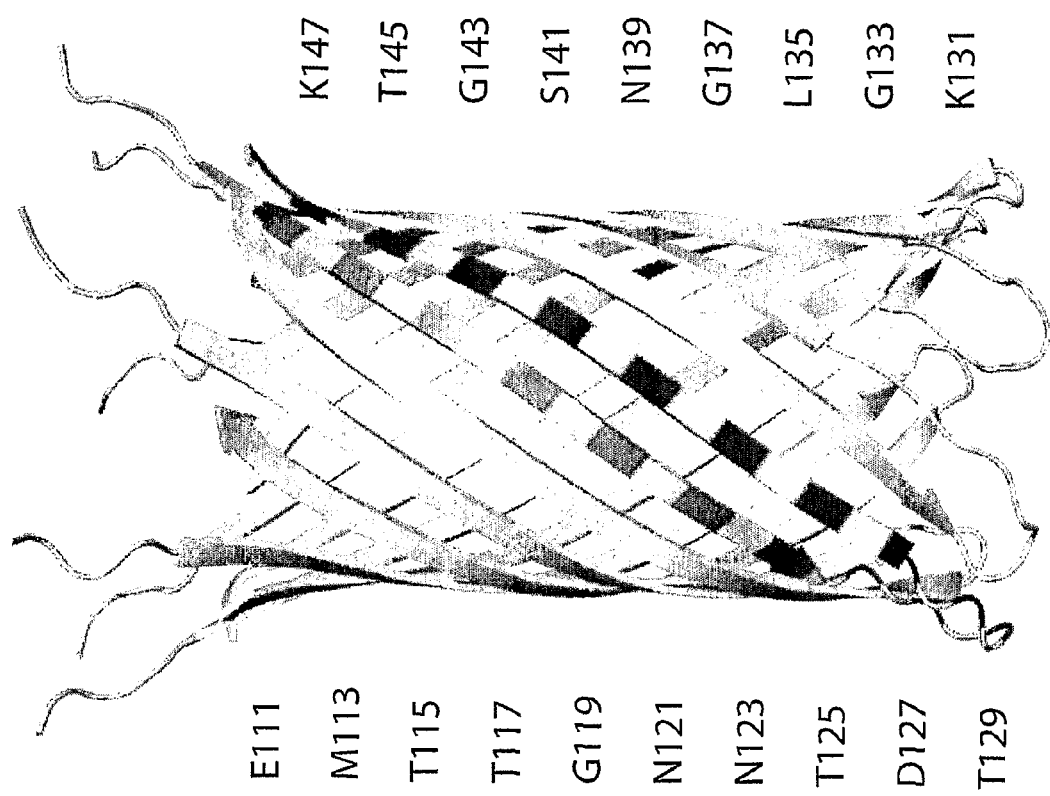
FIG. 7 shows a diagram indicating the location of key mutations in the β-barrel of αHL.

Two sets of mutants were designed; one set to position the attached adapter near the top of the β-barrel, while the second set were designed to position the adaptor near to the N139Q position (Table 2 below and FIG. 7).

TABLE 2

Mutants produced for optimising the position of the cyclodextrin for base detection and discrimination.

| Set 1 - Attachment Near Residue 113 | Set 2 - Attachment Near Residue 139 |
|---|---|
| HL-(M113R/N139Q)$_6$(M113R/T115C-D8)$_1$ | HL-(M113R/N139Q)$_6$(M113R/N139Q/N123C-D8)$_1$ |
| HL-(M113R/N139Q)$_6$(M113R/T117C-D8)$_1$ | HL-(M113R/N139Q)$_6$(M113R/N139Q/G125C-D8)$_1$ |
| HL-(M113R/N139Q)$_6$(G119C-D8)$_1$ | HL-(M113R/N139Q)$_6$(M113R/N139Q/T133C-D8)$_1$ |
| HL-(M113R/N139Q)$_6$(M113R/N139Q/N121C-D8)$_1$ | HL-(M113R/N139Q)$_6$(M113R/N139Q/L135C-D8)$_1$ |
|  | HL-(M113R/N139Q)$_6$(M113R/N139Q/G137C-D8)$_1$ |

Figure 2:
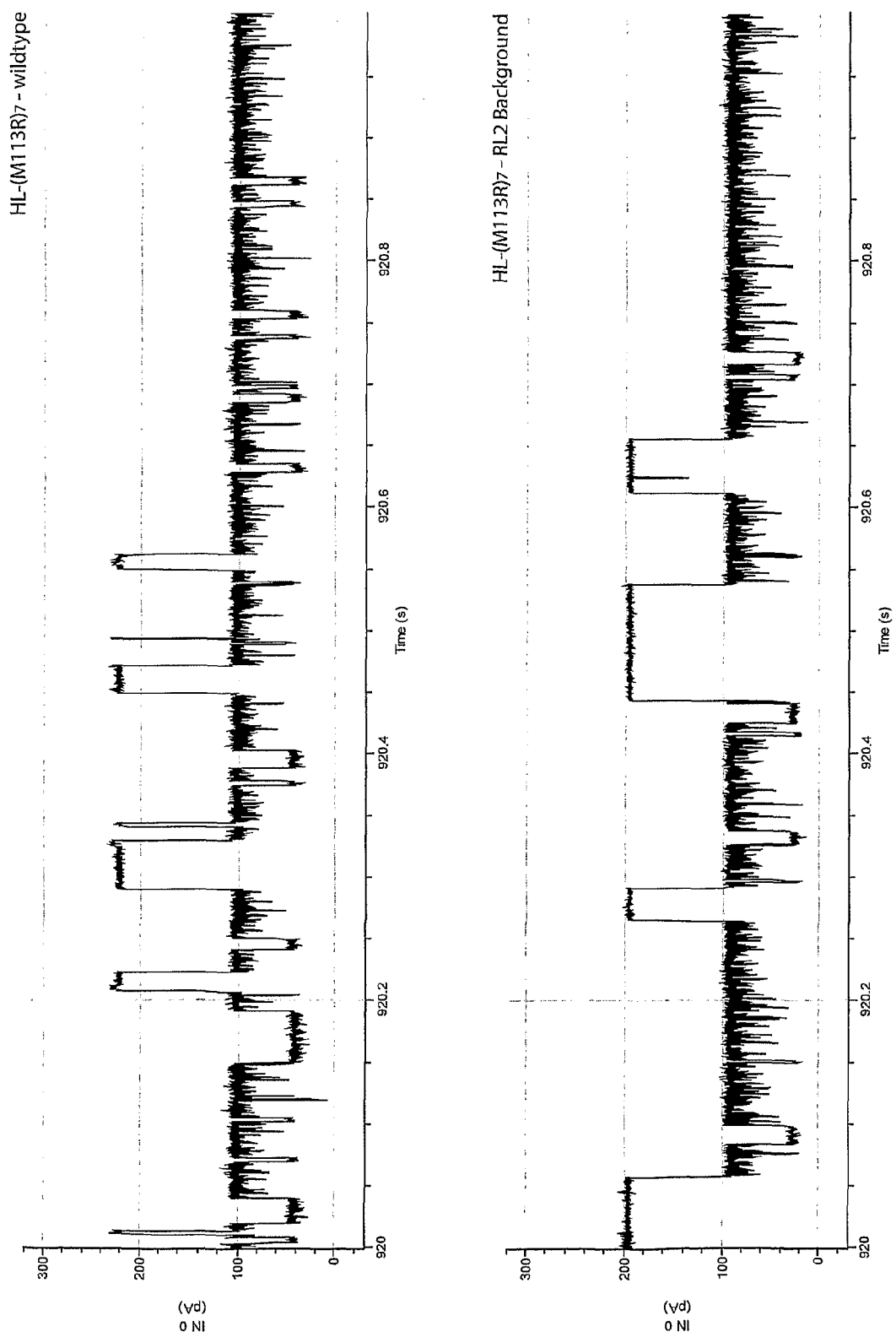
FIG. 2 shows single channel recordings of the HL-(M113R)$_7$ in a wild-type background (top) and HL-(M113R)$_7$ in a RL2 background (bottom). am$_7$-βCD binding and dNMP detection can be seen.
Figure 3:
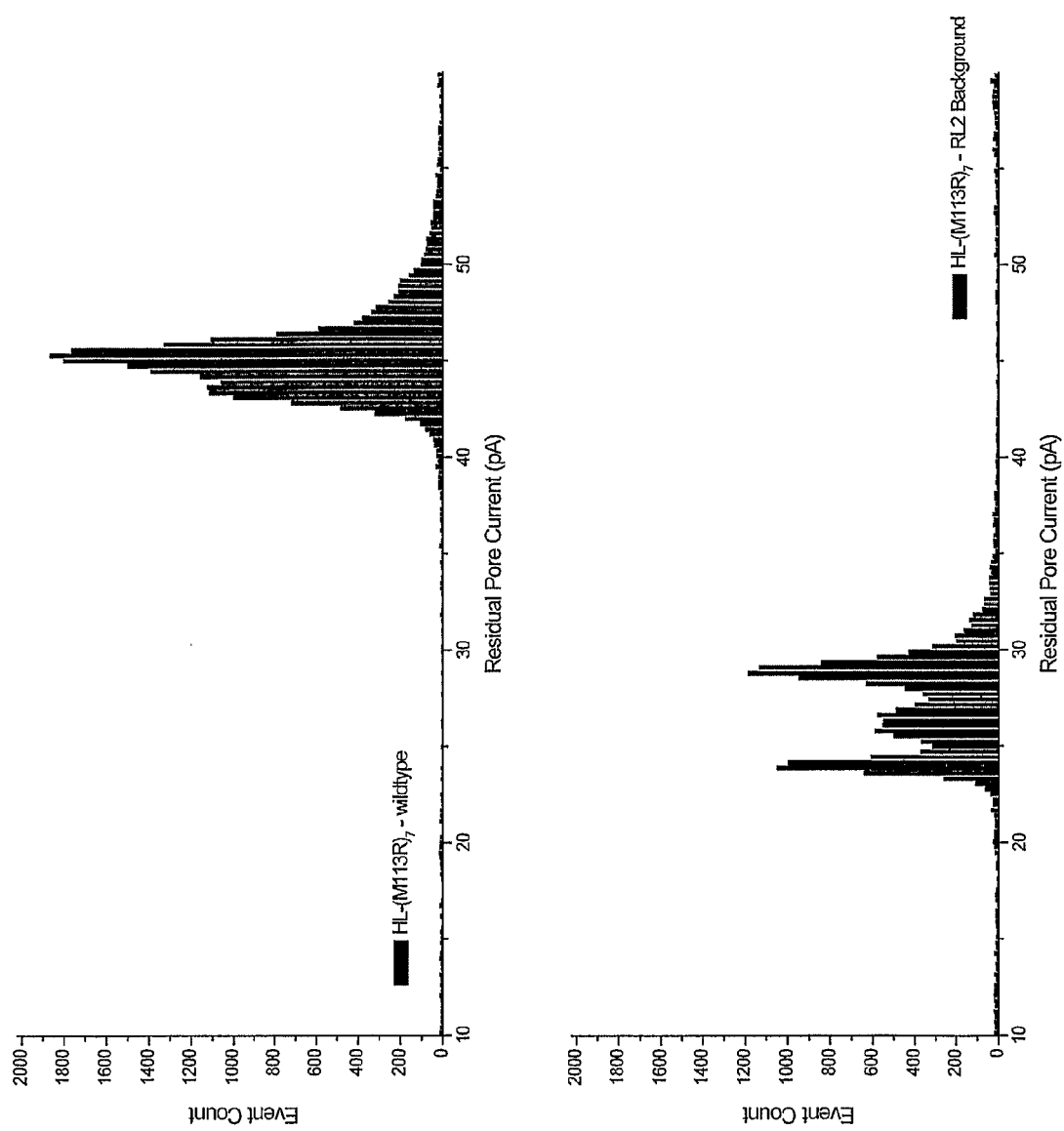
FIG. 3 shows the corresponding histograms of dNMP events from FIG. 1. Ledt is wild-type and right is RL2 (1200 mM KCl, 150 mV, pH 7.5).

The two mutants yielded very different results. Adapter binding events were seen using the am$_7$-βCD in a both mutants, and dNMP events were regularly seen, but the binding of the dNMPs was very different (FIGS. 2 and 3).

One clear difference between the two mutants is the amplitude of the current block; using the RL2-based mutant, the residual current when dNMP binding occurred was 23-33 pA and the distribution of the bases was sufficient to distinguish all four bases. However, in the wild-type-based mutant, the amplitude of the residual current was 45-50 pA and although the features could be seen in the histogram, dNMP discrimination was poor.

Figure 4:
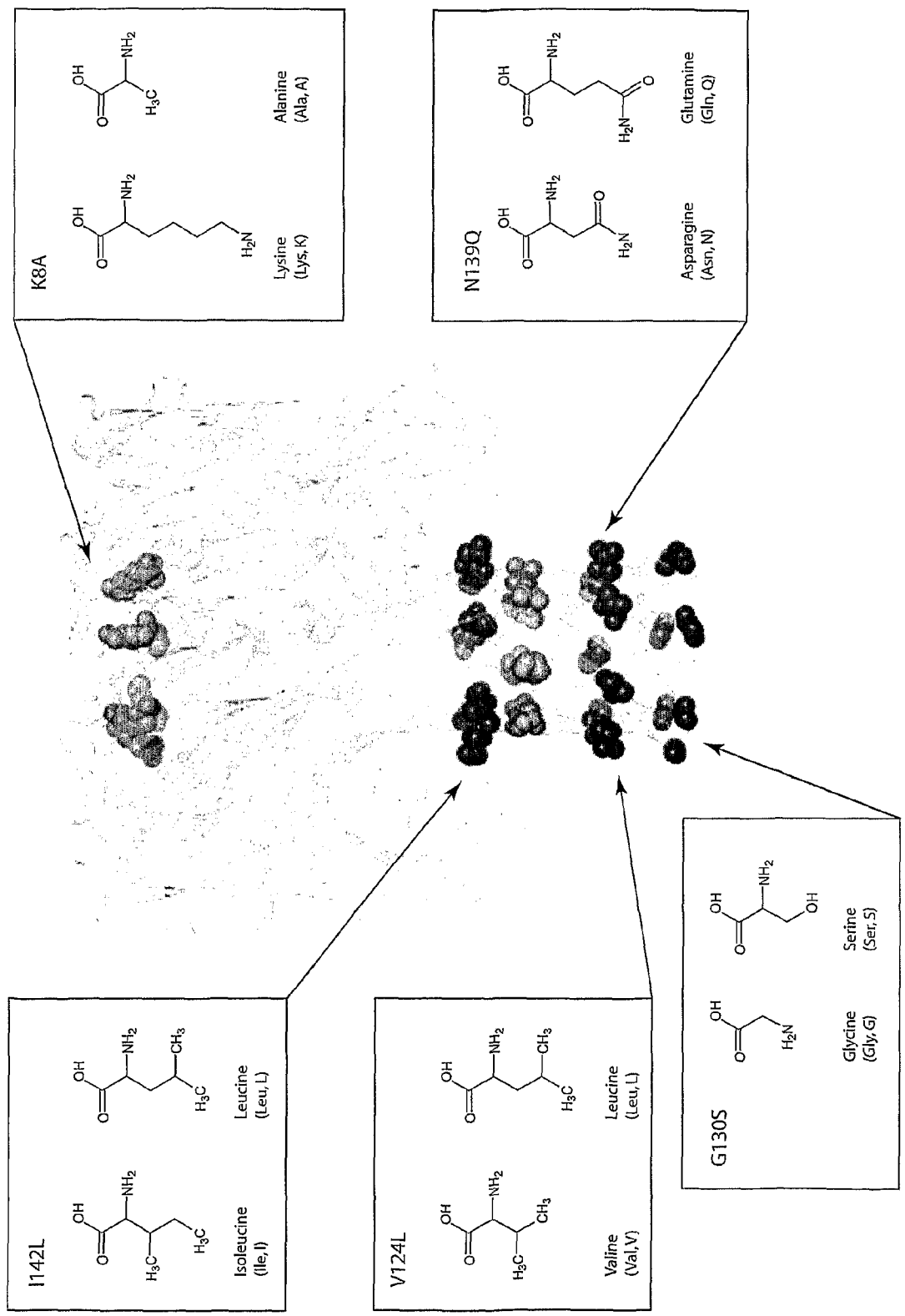
FIG. 4 shows a diagram indicating the key mutations of the RL2 compared to the wild-type.

The differences in background between the wild-type-based HL-(M113R)$_7$ mutant and the RL2-based HL-(M113R)$_7$ were believed to be due to the additional mutations present in the RL2 background. Out of these mutations, the N139Q was considered to be the most likely to cause the differences between the two mutants. The K8A residue is located in the cap region of the protein and is unlikely to interfere with the dNMP recognition, while the V127L, I142L and G130S mutations are on the exterior face of the β-barrel and are believed to have little impact (FIG. 4).

Figure 5:
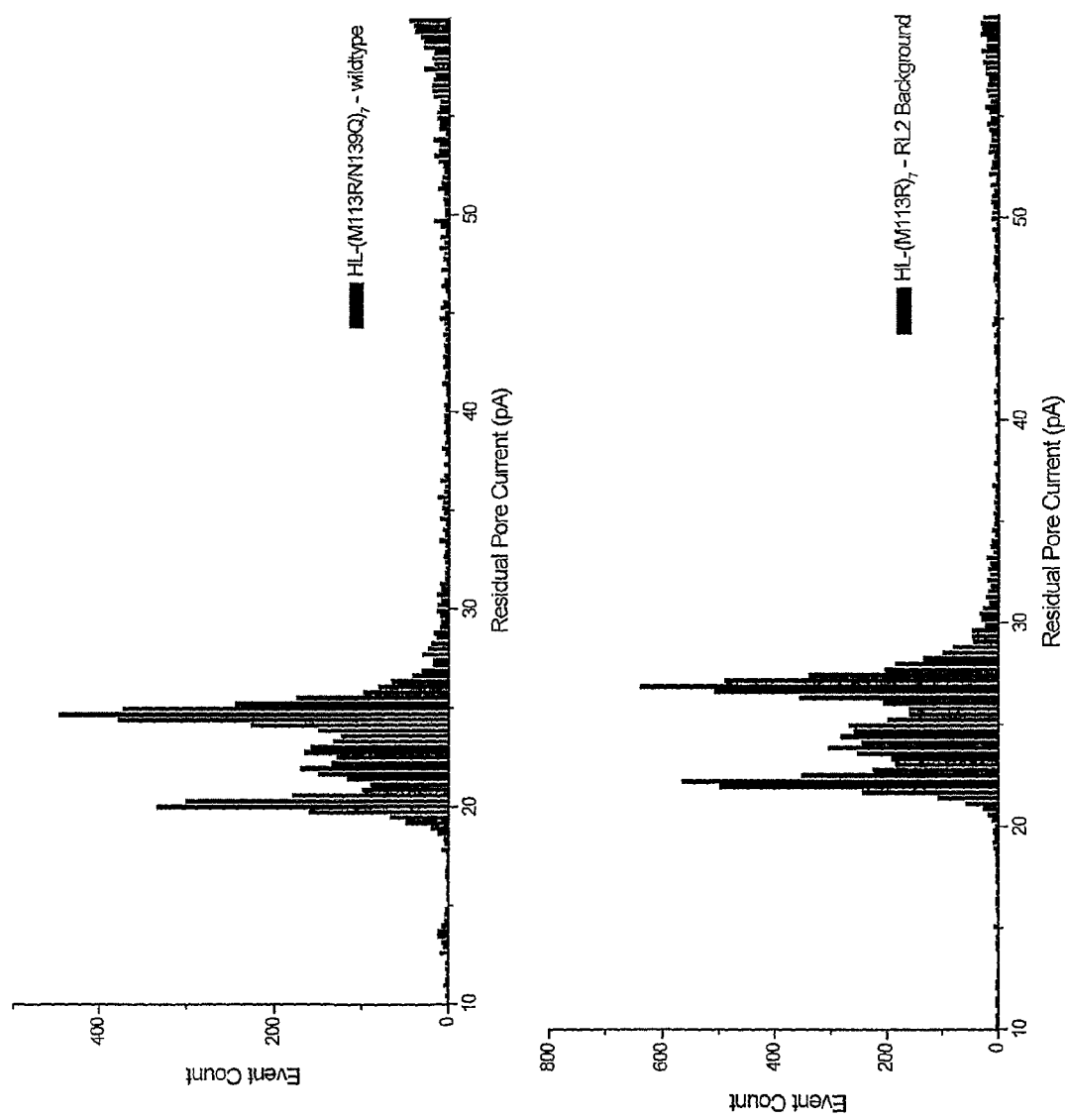
FIG. 5 shows a histogram of residual current binding when dNMPs are bound to the HL-(M113R)$_7$RL2 background and the HL-(M113R/N139Q)$_7$ wt background. This Figure shows the importance of the N139Q mutation in the RL2 background (compare with FIG. 3) (800 mM KCl, 160 mV, pH 7.5).

To investigate the impact of the N139Q mutation on the base binding, the mutation was incorporated into the wild-type background, along with the arginine needed for dNMP detection to give the HL-(M113R/N139Q)$_7$ protein. This protein contained seven of the subunits shown in SEQ ID NO: 8. It was compared to the RL2-based construct discussed above under similar conditions (FIG. 5).

From this data, it is clear that the N139Q mutation is necessary for base detection, an effect not previously realised.

It should be noted that some of the mutants only contain six monomers with the M113R or N139Q mutation, but the behavioural differences are expected to be minimal.

2.3 Covalent Attachment of am$_7$-βCD

Figure 8:
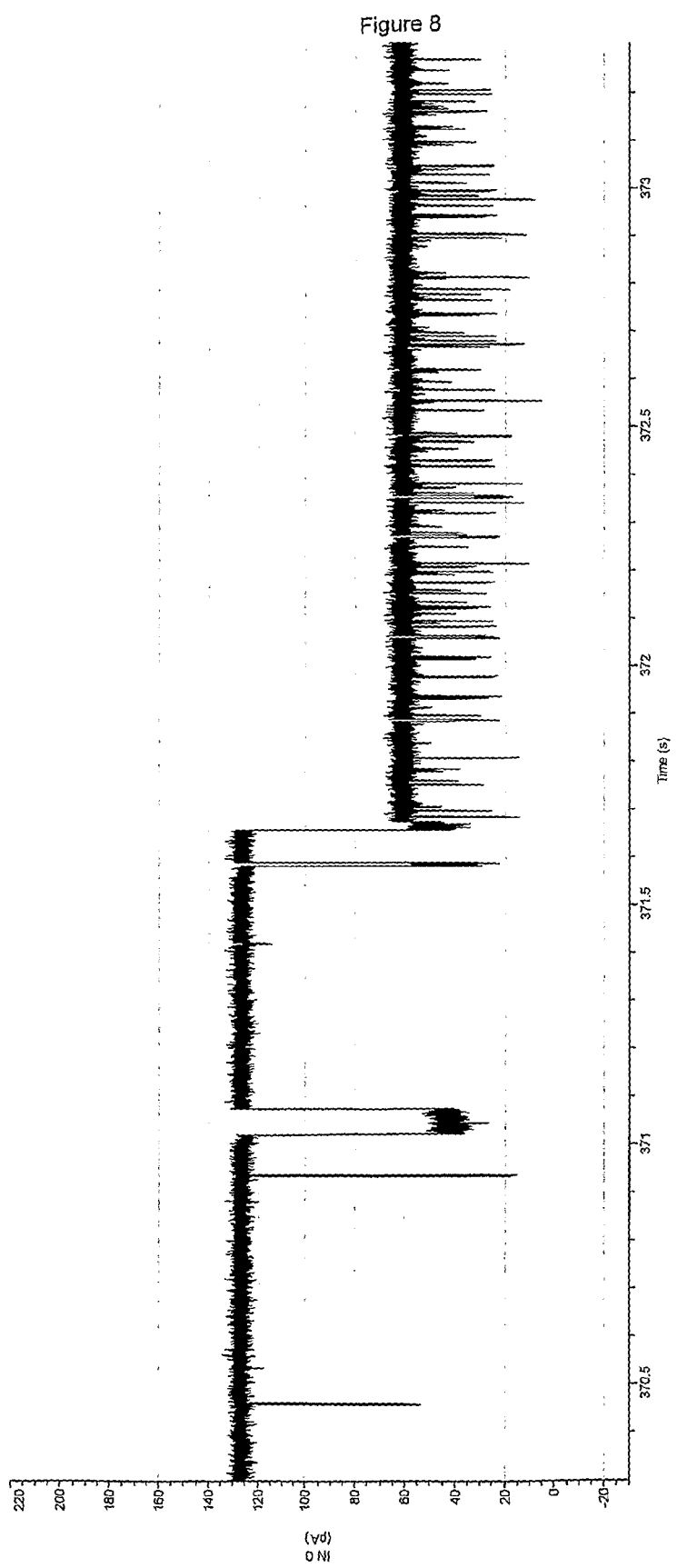
FIG. 8 shows single channel recording of the HL-(M113R/N139Q)$_6$(M113R/T115C-D8)$_1$ mutant. Reaction with the am$_6$amPDP$_1$-βCD can be seen resulting in a fluctuating, noisy baseline (no bases present).

The reactive am$_6$amPDP$_1$-βCD was successfully attached to a large number of the mutants under a range of experimental conditions. The reaction is characterised by a permanent drop in the residual pore current, which can not be removed by changing the polarity or magnitude of the applied potential (FIG. 8). A further test of this reaction is to reduce the disulphide bond connecting the adapter to the protein pore via the addition of dithiothreitol (DTT).

It should be noted that it is common to see a number of different cyclodextrin states prior to reaction, but once reacted, the current level remains relatively constant. Furthermore, the covalent attached cyclodextrin level often shows a different magnitude to the un-reacted cyclodextrin levels.

2.4 High Positions of Attachment—Residues 115 to 121

The high positions of attachment for the cyclodextrin were chosen to promote the position of the cyclodextrin near the top of the β-barrel. All the positions chosen were closer to the amino terminal, with the side chains directed inside the β-barrel (odd numbered residues). The design of the linker on the modified cyclodextrin means that the position of the top of the cyclodextrin will be roughly four amino-acids away from the site of attachment. Hence, the 117 attachment will correspond to the top of the cyclodextrin being at the 113 position.

Position 115

Using this guide, the 115 position is expected to be too high up the β-barrel for the reacted cyclodextrin to be stably positioned near the 113, especially given the presence of the arginine groups in the M113R mutant, which would be expected to repel the primary amines of the cyclodextrin. However, this protein did react with the am$_6$amPDP$_1$-βCD.

Although a reaction was achieved at the 115 position of α-HL, the baseline was noisy and showed large fluctuations in the current, even before nucleotide bases were added. This could be due to movement of the cyclodextrin within the β-barrel, or the binding of other species present in the solution, however, the addition of nucleotides did not affect the signal from this construct.

Position 117

Figure 9:
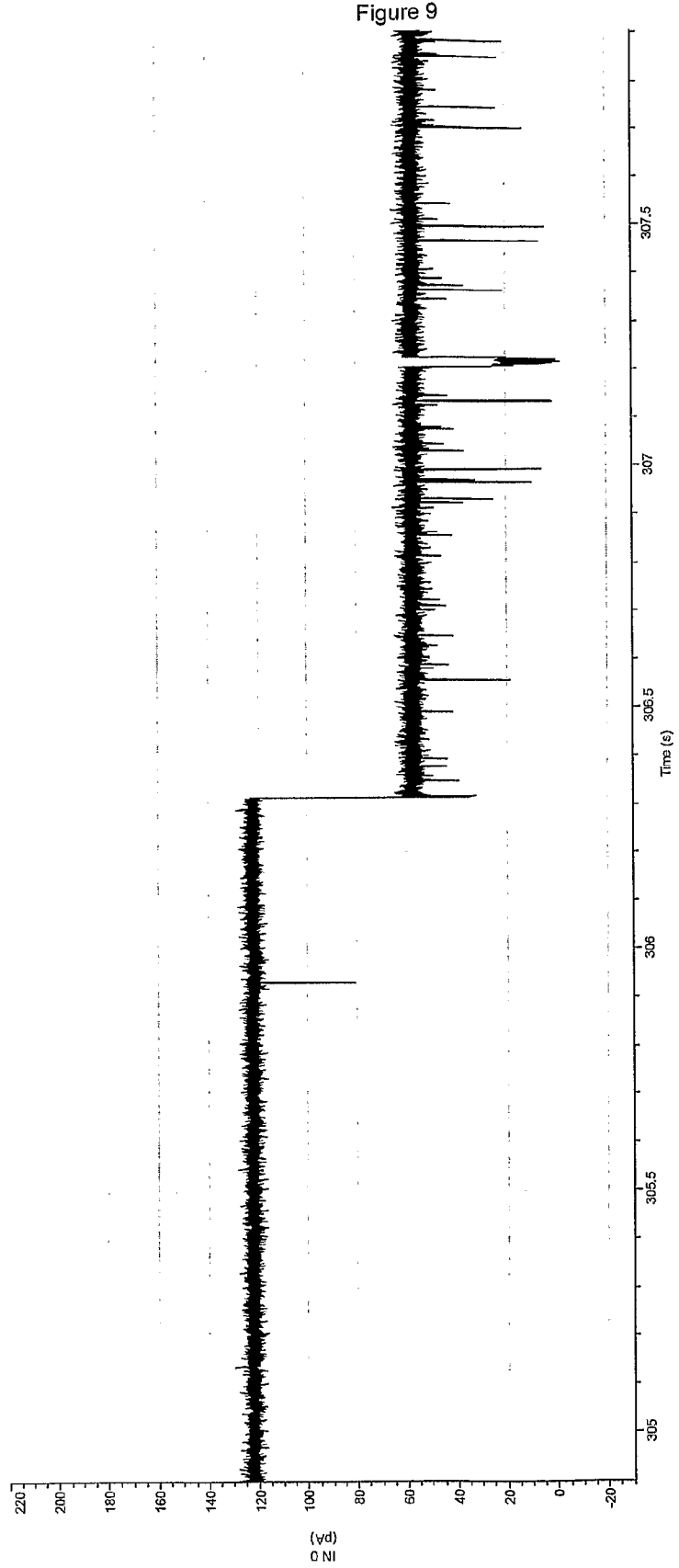
FIG. 9 shows single channel recording of the HL-(M113R/N139Q)$_6$(M113R/T117C-D8)$_1$ mutant, which gives a fluctuating, noisy baseline (no bases present).

Attaching the cyclodextrin at the 117 position should position the cyclodextrin near reside 113. An example trace from this construct can be seen below (FIG. 9). The HL-(M113R/N139Q)$_6$(M113R/T117C-D8)$_1$ mutant reacted with the am$_6$amPDP$_1$-βCD, but the baseline was very similar to the HL-(M113R/N139Q)$_6$(M113R/T115C-D8)$_1$ mutant. The addition of the nucleotides did not produce any noticeable change in the pore signal. The poor behaviour arising from attachment at the 117 position may be a result of the cyclodextrin interacting with the positively charged arginines, which will repel the charged adapter. The arginines required for base sensing may be too close to the cyclodextrin and could prevent the cyclodextrin from achieving a stable position.

Position 119

When the cysteine position was shifted further down the β-barrel to the 119 position, the reaction with the am$_6$amPDP$_1$-βCD gave a cleaner baseline than either the 115 or the 117 position. However, there were still some fluctuations in the current, manifesting as spikes in the baseline (FIG. 10).

Figure 10:
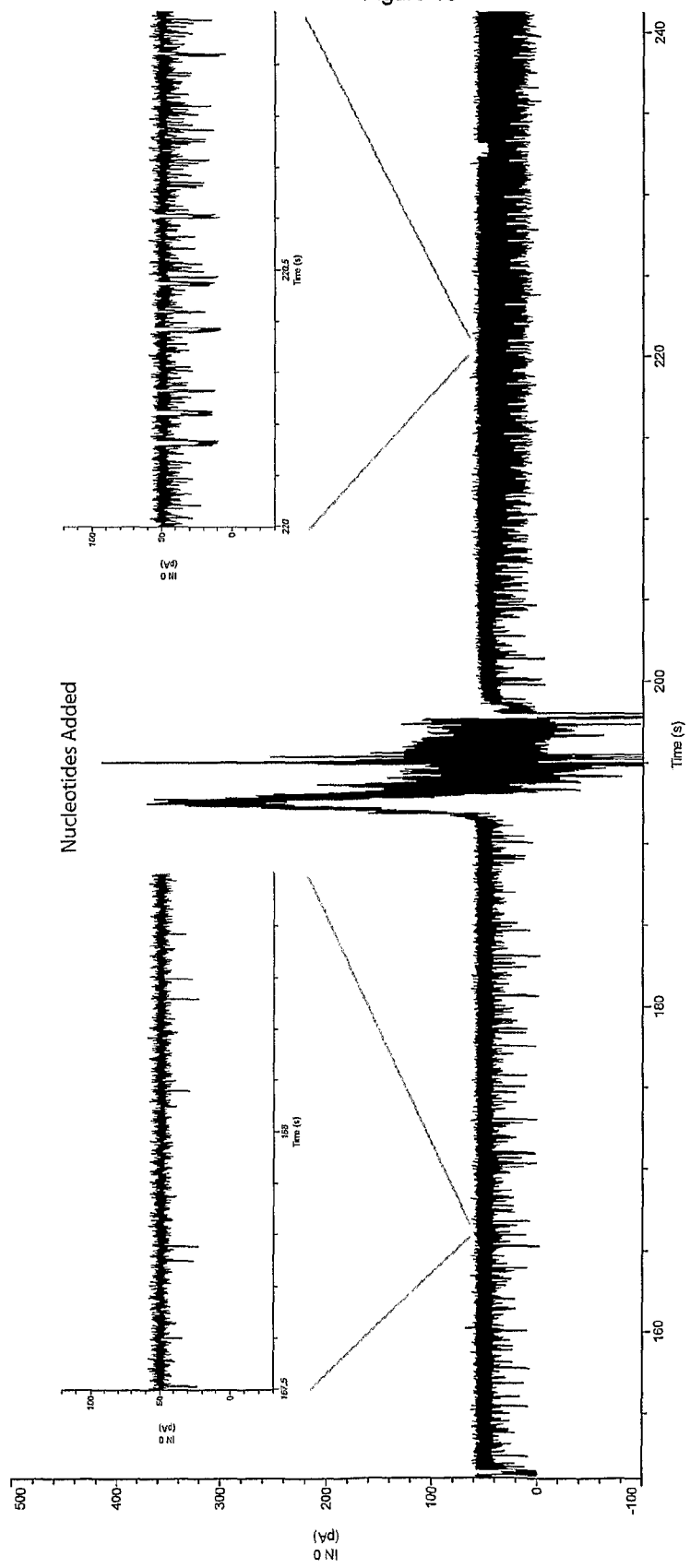
FIG. 10 shows single channel recording of the HL-(M113R/N139Q)$_6$(M113R/G119C-D8)$_1$ mutant reacted with the am$_6$amPDP$_1$-βCD before and after the nucleotides are added. It also shows a close up of the baseline after nucleotides are added.

The addition of nucleotides to the HL-(M113R/N139Q)$_6$(M113R/G119C-D8)$_1$.am$_6$amPDP1-βCD construct resulted in modulations in the Nanopore current, clearly showing continuous nucleotide binding events (FIG. 10). The HL-(M113R/N139Q)$_6$(M113R/G119C-D8)$_1$ contained six of the subunits shown in SEQ ID NO: 8 and one of the subunits shown in SEQ ID NO: 10.

Figure 12:
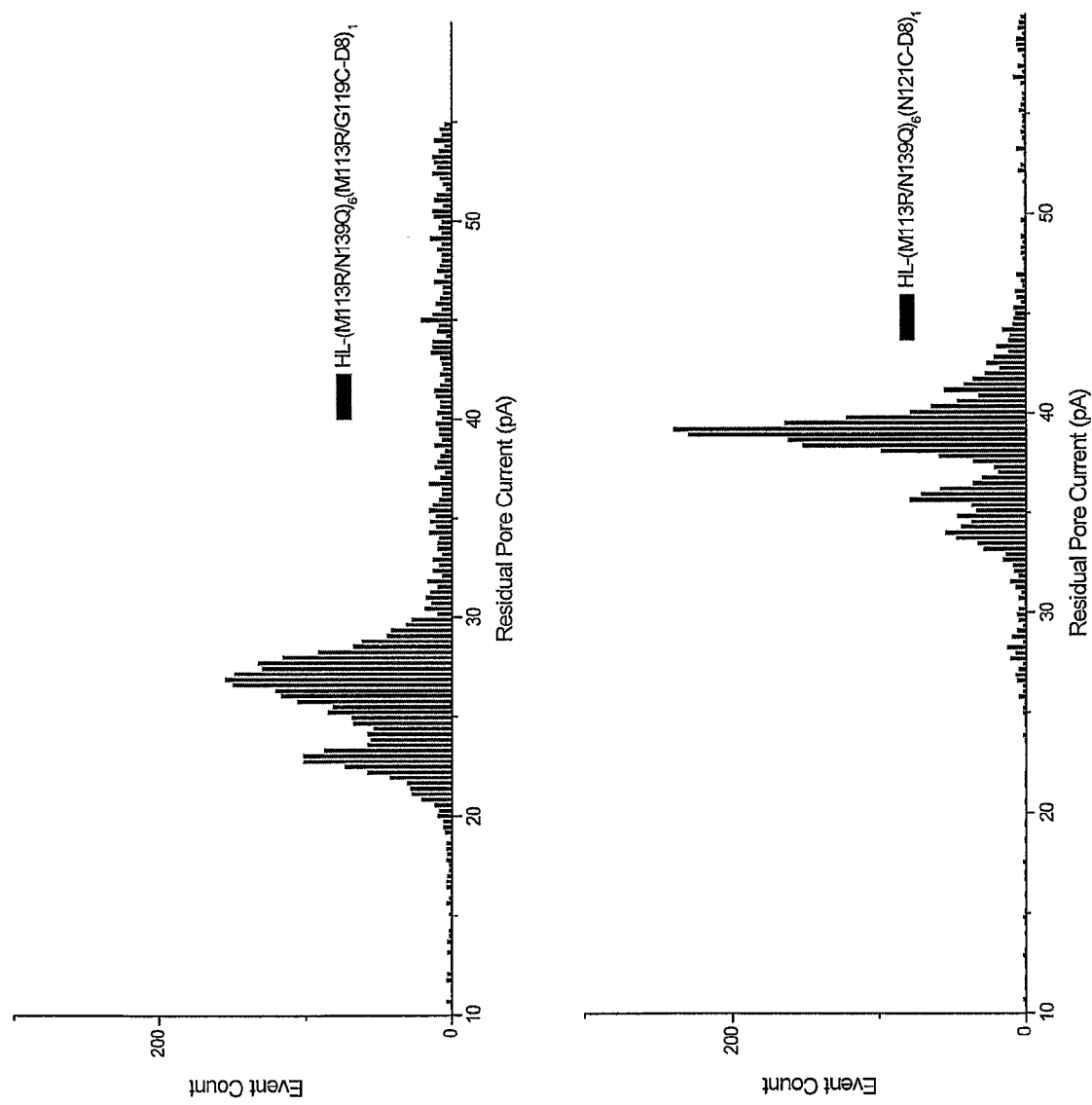
FIG. 12 shows histograms for the HL-(M113R/N139Q)$_6$(M113R/G119C-D8)$_1$ (left) and the HL-(M113R/N139Q)$_6$(M113R/N139Q/N121C-D8)$_1$ mutant (right). Limited base discrimination can be seen at 800 mM KCl, 160 mV, pH 7.5.

The additional events in the baseline were still present and complicated the signal (FIG. 10), but the nucleotide events could easily be distinguished with the detected nucleotides giving rise to a variation in the residual pore current. These events can then be plotted as a histogram to show the base discrimination (FIG. 12).

Position 121

Figure 11:
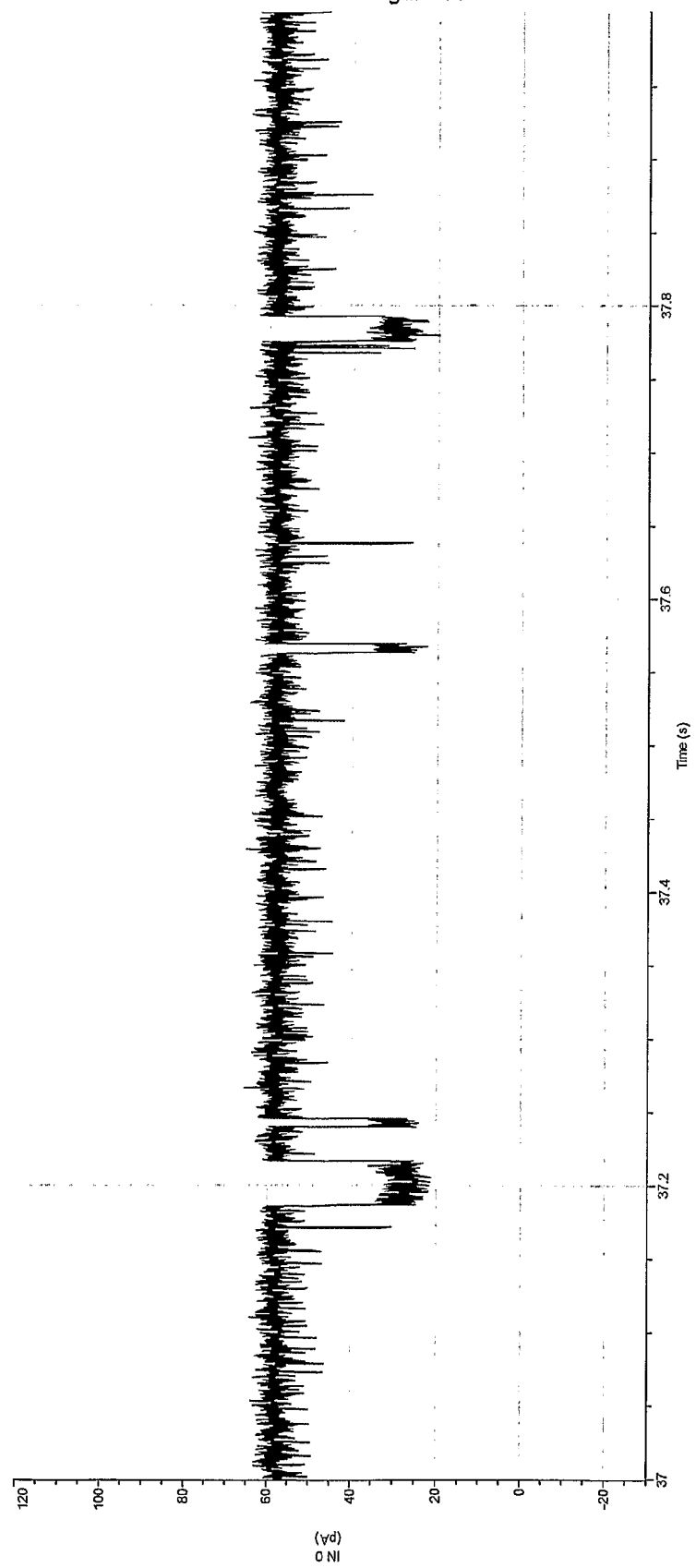
FIG. 11 shows single channel recording of the HL-(M113R/N139Q)$_6$(M113R/N139Q/N121C-D8)$_1$ mutant reacted with the am$_6$amPDP$_1$-βCD after nucleotides were added.

The most promising cysteine position from this group of mutants was at residue 121. In particular, the HL-(M113R/N139Q)$_6$(M113R/N139Q/N121C-D8)$_1$.am$_6$amPDP1-βCD construct. This construct contained six of the subunits shown in SEQ ID NO: 8 and one of the subunits shown in SEQ ID NO: 12. The baseline of the reacted pore showed fewer fluctuations than the previously tested mutants and showed clear base binding (FIG. 11).

The construct with the cysteine at the 121 position showed base discrimination, with better resolution than the corresponding mutant with a cysteine at the 119 position. This can be easily seen in the histograms of the residual pore current for each mutant (FIG. 12).

Although the HL-(M113R/N139Q)$_6$(M113R/N139Q/N121C-D8)$_1$ mutant is capable of reacting with the modified cyclodextrin to show continuous base detection and some discrimination between the bases, the overlap between the residual current would make sequencing through this approach difficult.

2.5 Low Positions of Attachment—Residues

The base resolution was increased as the cysteine position was moved down the β-barrel, therefore the lower cysteine positions were investigated to see if the base discrimination could be further improved.

The cysteine position was moved to the 123, 125, 133, 135 and 137 residues; these mutants were chosen to position the adapter as close as possible to the N139Q mutation. Examination of the cyclodextrin linker length shows that the distance between the top of the cyclodextrin (secondary hydroxyl face) and the thiol group is 9.2 Å. The distances between the amino-acid linker at various positions in the β-barrel and the glutamine rings at the 139 positions are shown in Table 3.

TABLE 3

Position of various amino-acid residues in the β-barrel, distance from the N139Q mutation and estimates of the distance between the cyclodextrin secondary hydroxyls and the glutamines when reacted.

| Position of Residue | Distance from N139Q | CD Hydroxyl to N139Q Distance |
|---|---|---|
| N123C | 10.3 Å | 1.1 Å |
| T125C | 13.5 Å | 4.3 Å |
| G133C | 17.0 Å | 7.8 Å |
| L135C | 9.1 Å | 0.1 Å |
| G137C | 7.0 Å | 2.2 Å |

It is clear from these measurements that the most suitable cysteine position for attachment of the modified cyclodextrin is the L135C residue, where the distance from the N139Q position is 9.1 Å. This value closely matches the distance between the hydrogen bonding and the thiol attachment site of the cyclodextrin (9.2 Å), which should maximise the hydrogen bonding between the pore and the adapter and hence, stabilise the construct.

The mutants created to test this hypothesis are shown in Table 4.

TABLE 4

Mutants produced for optimising the position of the cyclodextrin near the N139Q for base discrimination

| Attachment Position | Mutant Name |
|---|---|
| 123 | HL-(M113R/N139Q)$_6$(M113R/N139Q/N123C-D8)$_1$ |
| 125 | HL-(M113R/N139Q)$_6$(M113R/N139Q/G125C-D8)$_1$ |
| 133 | HL-(M113R/N139Q)$_6$(M113R/N139Q/T133C-D8)$_1$ |
| 135 | HL-(M113R/N139Q)$_6$(M113R/N139Q/L135C-D8)$_1$ |
| 137 | HL-(M113R/N139Q)$_6$(M113R/N139Q/G137C-D8)$_1$ |

Positions 125 and 133

For the mutants with cysteines at the base of the β-barrel, positions 125 and 133, a reaction with the modified cyclodextrin (am$_6$amPDP$_1$-βCD) could not be observed. This may be due to the cysteine groups being in the wrong orientation to allow a reaction, alternatively, the cyclodextrin may react, but the cyclodextrin does not enter the β-barrel and hence is not observed by measurements of conductance through the pore.

Positions 135 and 137

Figure 13:
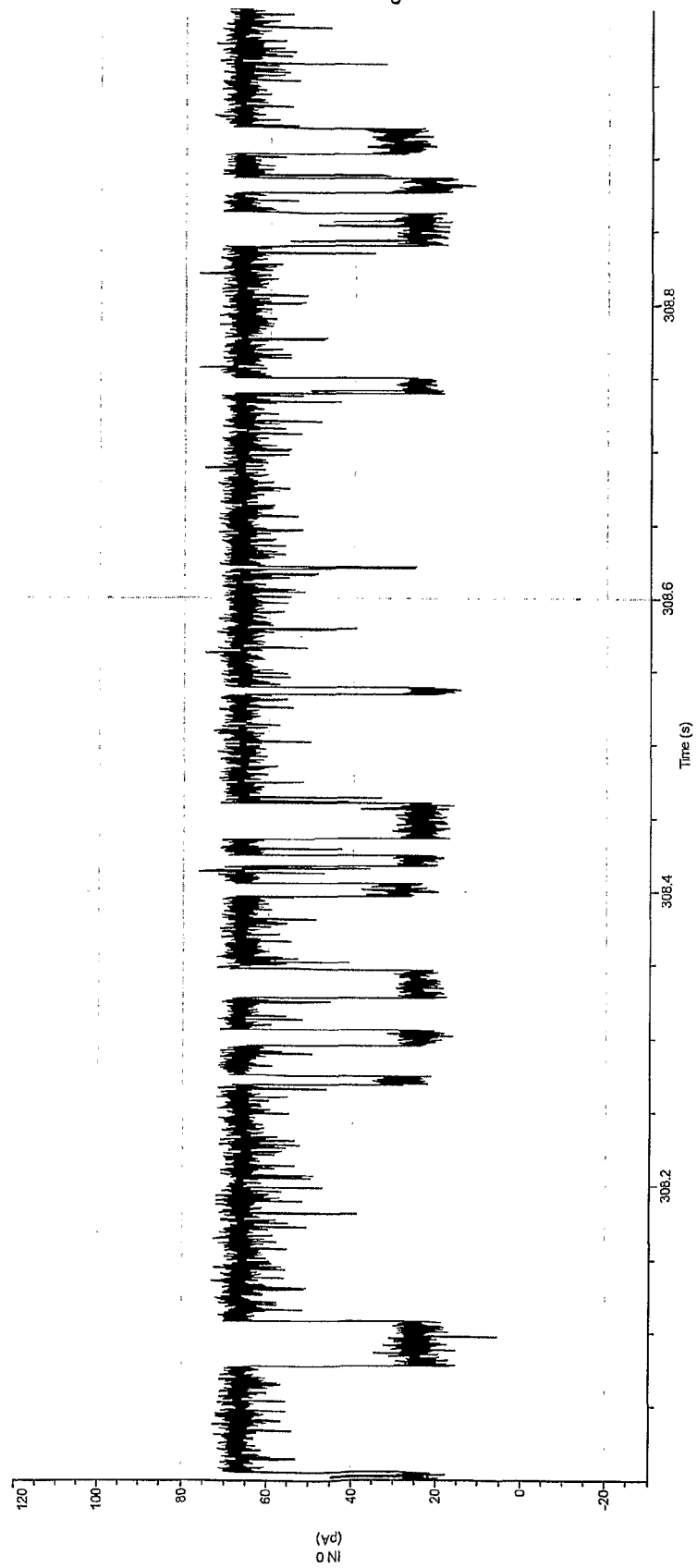
FIG. 13 shows single channel recording of the HL-(M113R/N139Q)$_6$(M113R/N139Q/N123C-D8)$_1$ mutant (5 kHz software filtered) reacted with the am$_6$amPDP$_1$-βCD after dGMP, dTMP, dAMP, dCMP were added (1 second shown).
Figure 14:
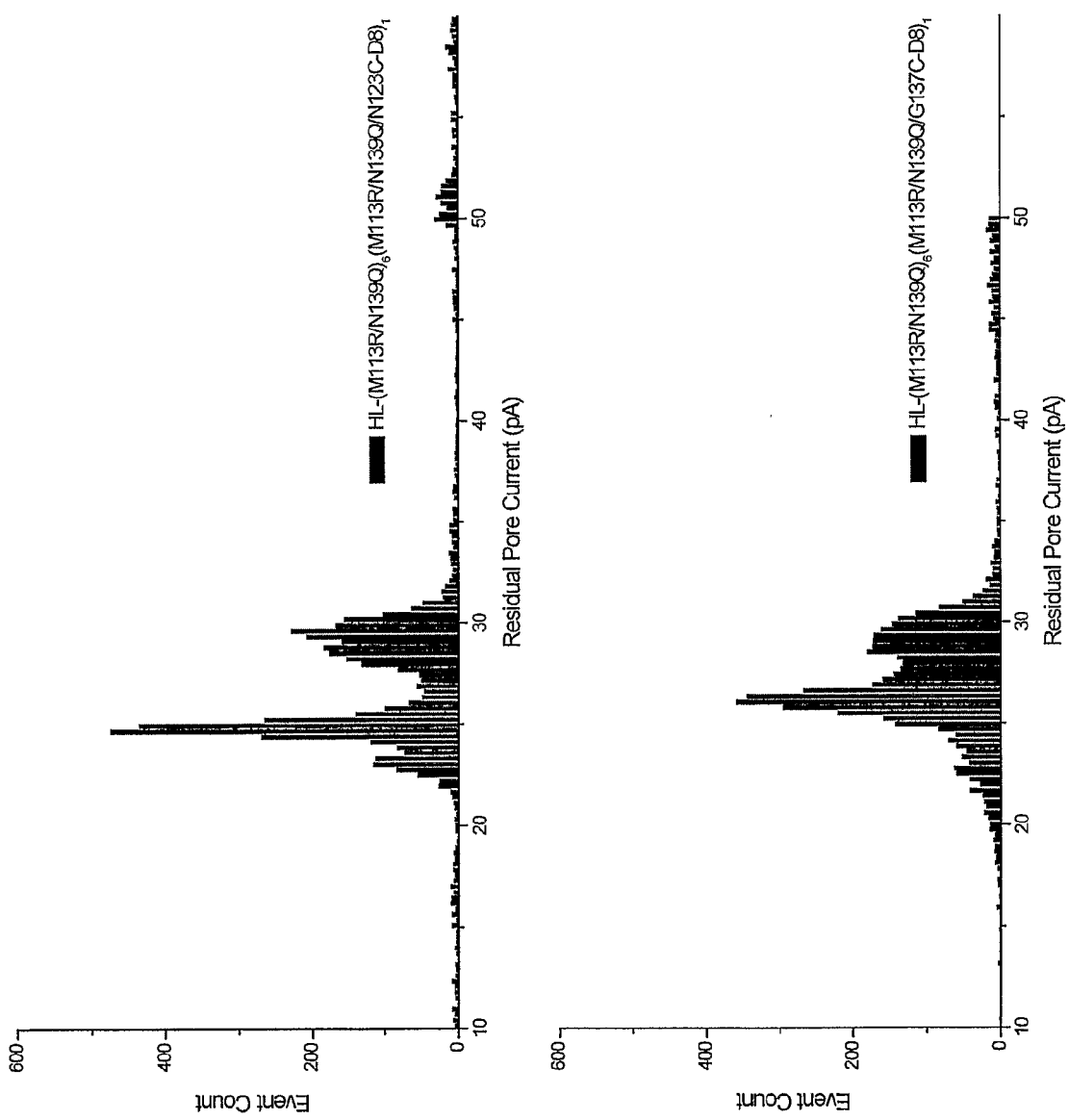
FIG. 14 shows histograms for the HL-(M113R/N139Q)$_6$(M113R/N139Q/N123C-D8)$_1$ (left) and the HL-(M113R/N139Q)$_6$(M113R/N139Q/G137C-D8)$_1$ mutant (right). Limited base discrimination can be seen (800 mM KCl, 160 mV, pH 7.5).

The 123 and 137 positions were tested for attachment of cyclodextrin and detection of dNMPs. These positions are close to the N139Q mutation and were expected to behave in a similar manner to attachment at the 121 position. Both of the positions reacted well with am$_6$amPDP$_1$-βCD, giving a stable baseline and showed base binding upon the addition of dNMPs. The base detection was good, but discrimination between all four bases was not possible under a range of conditions for both of these cysteine positions. An example trace from the HL-(M113R/N139Q)$_6$(M113R/N139Q/N123C-D8)$_1$ mutant can be seen below (FIG. 13) along with the histograms of the residual current when a dNMP is bound (FIG. 14).

Position 135

The distances calculated using molecular modeling showed that the best attachment position for base discrimination should be the L135C. This position was tested in the HL-(M113R/N139Q)$_6$(M113R/N139Q/L135C-D8)$_1$ mutant using the same conditions as the previous mutants. This mutant contained six of the subunits shown in SEQ ID NO: 8 and one of the subunits shown in SEQ ID NO: 14.

Figure 15:
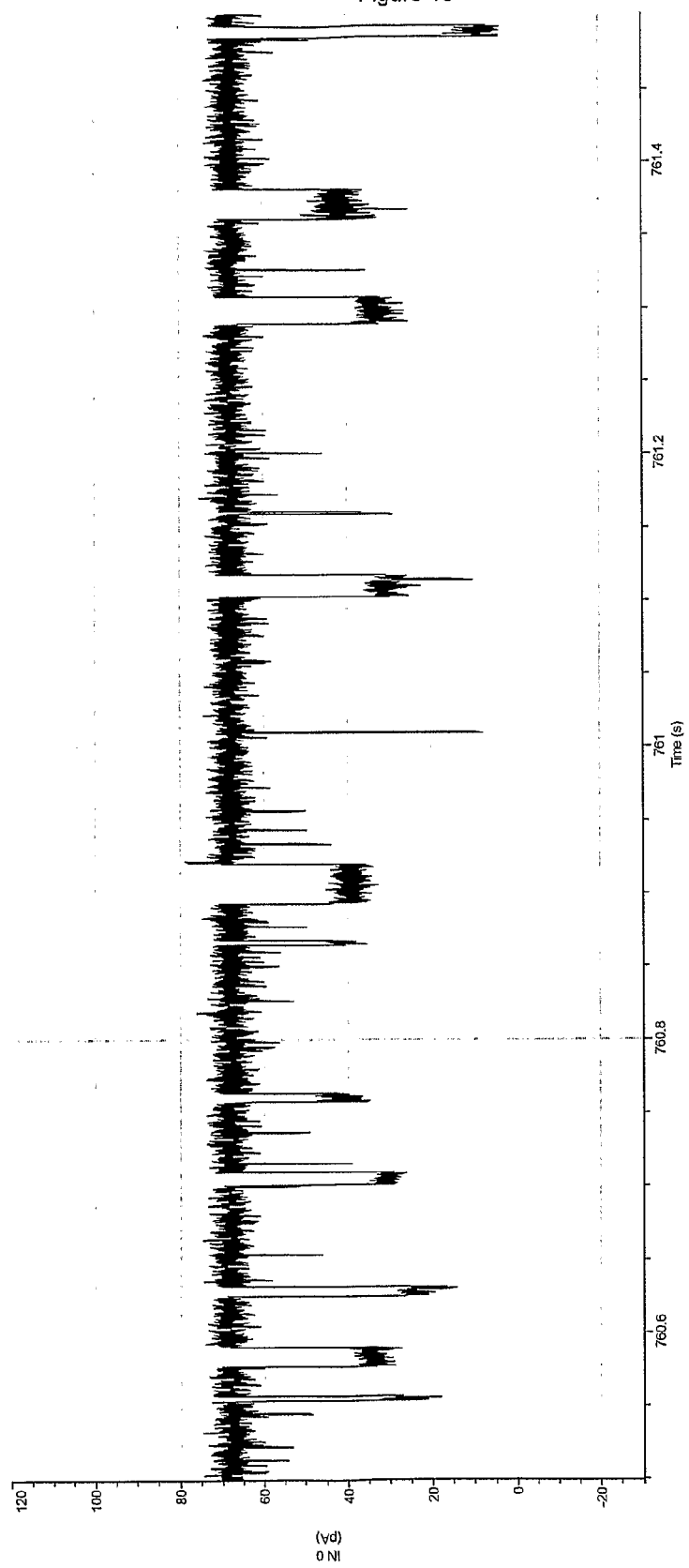
FIG. 15 shows single channel recording of the HL-(M113R/N139Q)$_6$(M113R/N139Q/L135C-D8)$_1$ mutant (5 kHz software filtered) reacted with the am$_6$amPDP$_1$-βCD after dGMP, dTMP, dAMP and dCMP were added (1 second shown).
Figure 16:
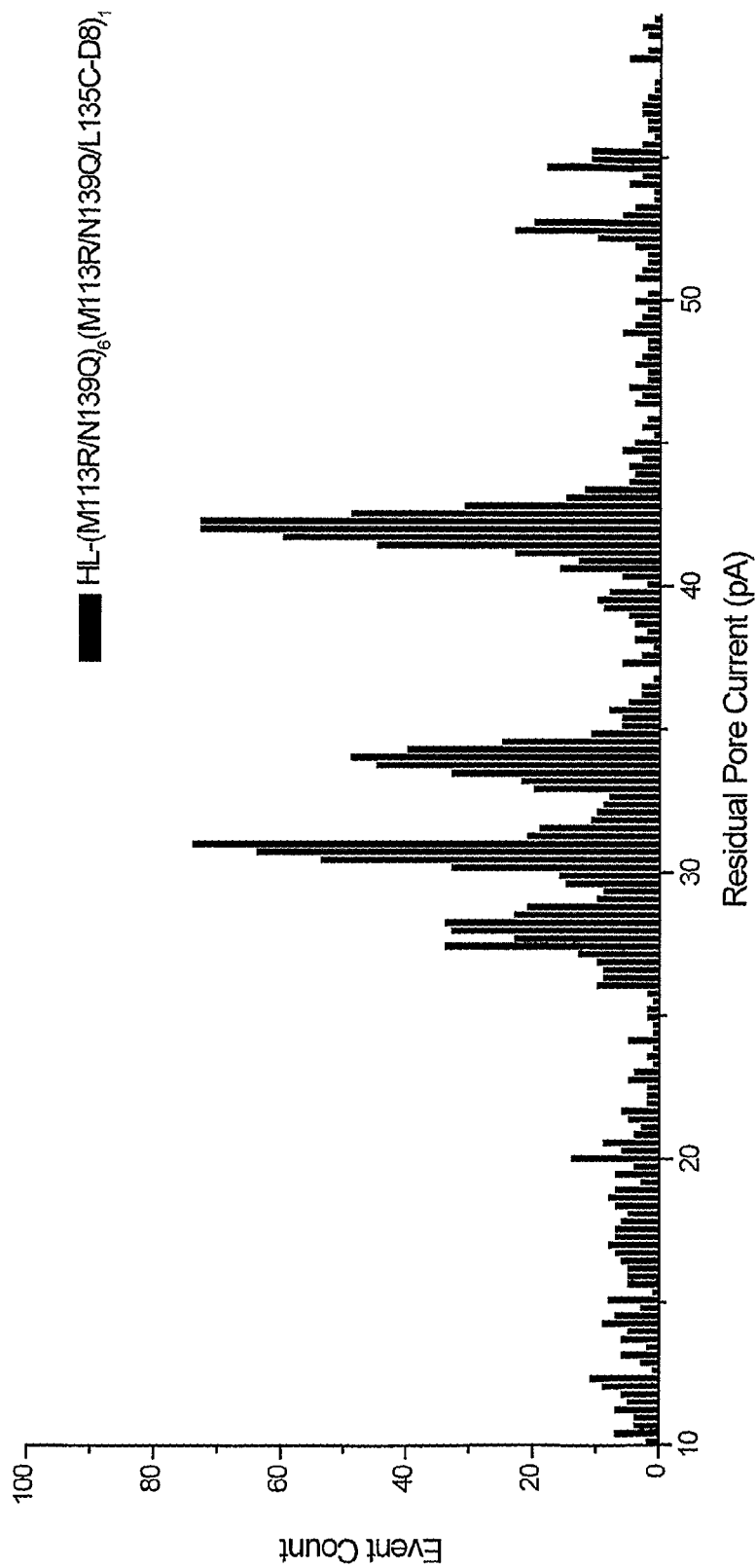
FIG. 16 shows a histogram for the HL-(M113R/N139Q)$_6$(M113R/N139Q/L135C-D8)$_1$ mutant. Good base discrimination can be seen (800 mM KCl, 160 mV, pH 7.5).

The cysteine reacted well with the modified cyclodextrin (am$_6$amPDP$_1$-βCD) to give a stable baseline. Upon addition of the nucleotides (dGMP, dTMP, dAMP, dCMP), additional binding events were observed. The amplitude of these peaks showed different populations (FIG. 15) which became clear when a histogram of residual pore current was plotted (FIG. 16).

The base resolution when the modified cyclodextrin is attached to the L135C position is clearly better than any of the other positions in the β-barrel and shows almost complete separation of all four nucleotides making it an excellent candidate for DNA or RNA sequencing.

This construct was therefore chosen as the baseline mutant for further study. The next few sections will deal with the effect of physical parameters on the base discrimination, the limitations of salt and temperature, the ability of the construct to identify different species, and a mechanistic evaluation of the baseline construct.

2.6 Base Binding at the L135C Position

With the HL-(M113R/N139Q)$_6$(M113R/N139Q/L135C-D8)$_1$ mutant defined as the baseline, experiments to identify each of the four peaks were undertaken. This was accomplished by running experiments with either a single nucleoside monophosphate species, or pairs of nucleoside monophosphates in solution (data not shown). These runs identified the peaks. They also showed that the nucleotide showing the largest block (and hence smallest residual current) is the dGMP, followed by dTMP, dAMP, with dCMP causing the smallest current block (and hence largest residual current). At 160 mV in 800 mM KCl, the residual current when a dNMP is bound is approximately: 30 pA (dGMP), 33 pA (dTMP), 36 pA (dAMP) and 44 pA (dCMP).

Figure 17:
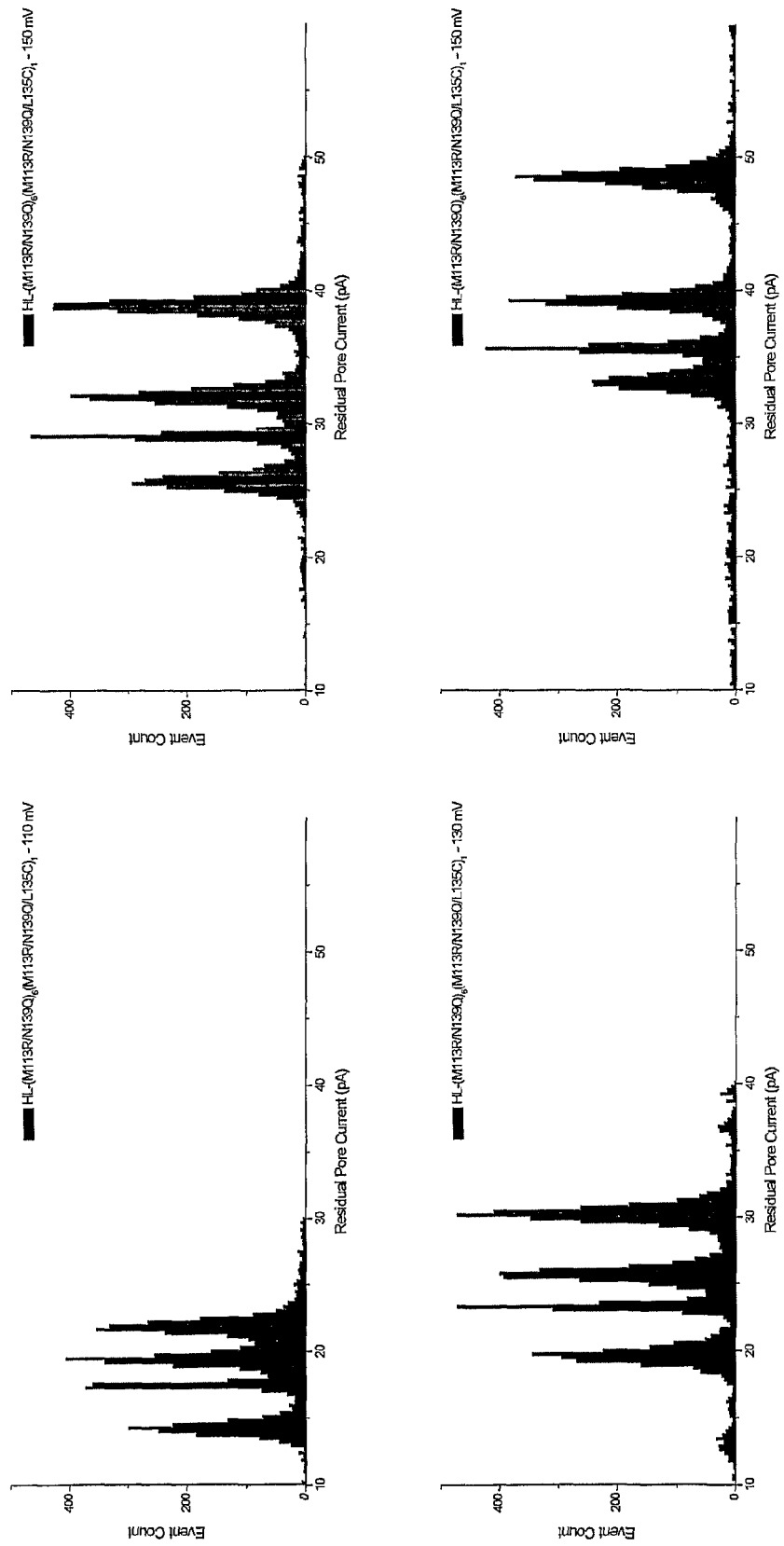
FIG. 17 shows residual current histograms of dNMP binding for the HL-(M113R/N139Q)$_6$(M113R/N139Q/L135C-D8)$_1$ mutant at a range of applied potentials (110-170 mV). The changes in the relative positions of the four nucleotides can be seen. The sharp black peak corresponds to the cyclodextrin level.

Although the magnitude of the observed current scales in an approximately linear fashion with the applied potential, the position of the four bases with respect to each other does not. This can be observed by examining the residual current histograms at a range of applied potentials (FIG. 17).

Figure 18:
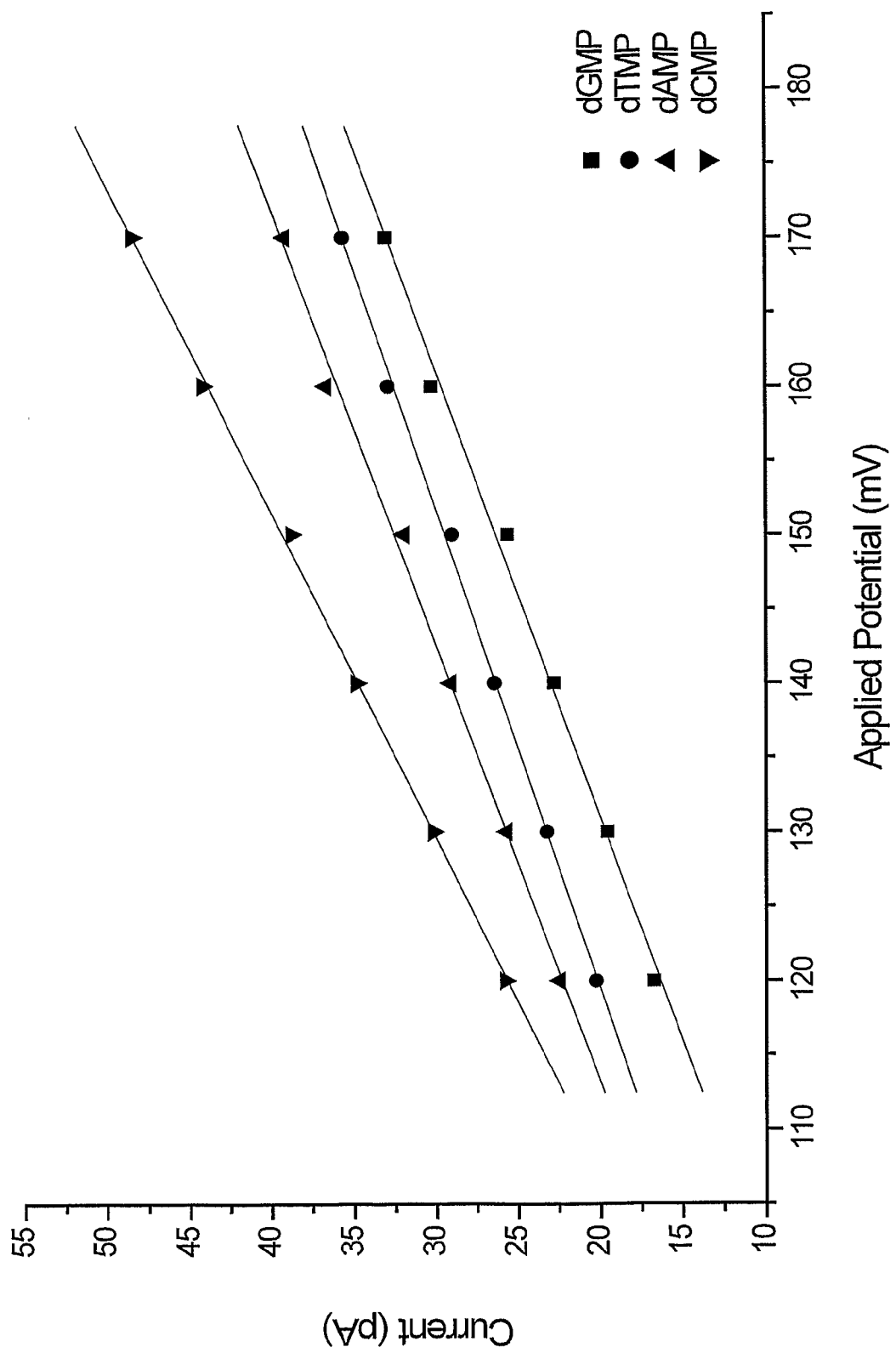
FIG. 18 shows a plot of the variation of peak position (residual pore current) with applied potential when a single nucleotide is bound to the pore.

This data shows that at lower potentials (110 mV), although the dGMP and the dTMP show good separation, the dAMP and the dCMP peaks overlap, while at higher potentials (170 mV), the dGMP and dTMP peaks now overlap while the dAMP and dCMP peaks show excellent resolution. The applied potential therefore provides an excellent control of peak overlap which can be utilised to enhance separation. This data is also summarised in FIG. 18.

Figure 19:
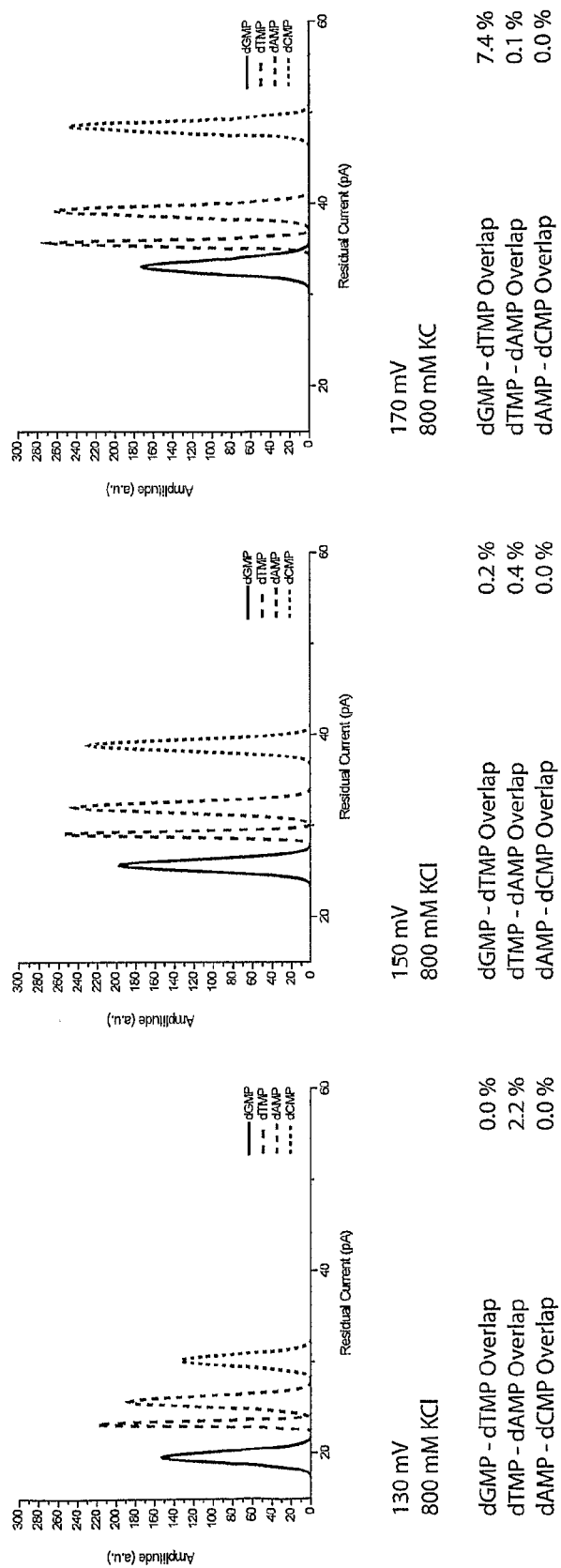
FIG. 19 shows a plot of the residual current histograms, Gaussian fits of each base and calculated areas of overlap for neighbouring bases for runs at applied potentials of 130, 150 and 170 mV.

In order to calculate the overlap of the residual current distribution, each individual dNMP peak seen in the residual current histograms was fitted to a single Gaussian. The Gaussians were then normalised so that the probability of detecting a single base was equal and the percentage overlap between each of the neighbouring bases was calculated from the area of overlap of the normalised Gaussians (FIG. 19).

Although there is variation between the peak overlap at different potentials, the variations are small, therefore this construct could be used for base discrimination at a wide range of operating conditions.

Figure 20:
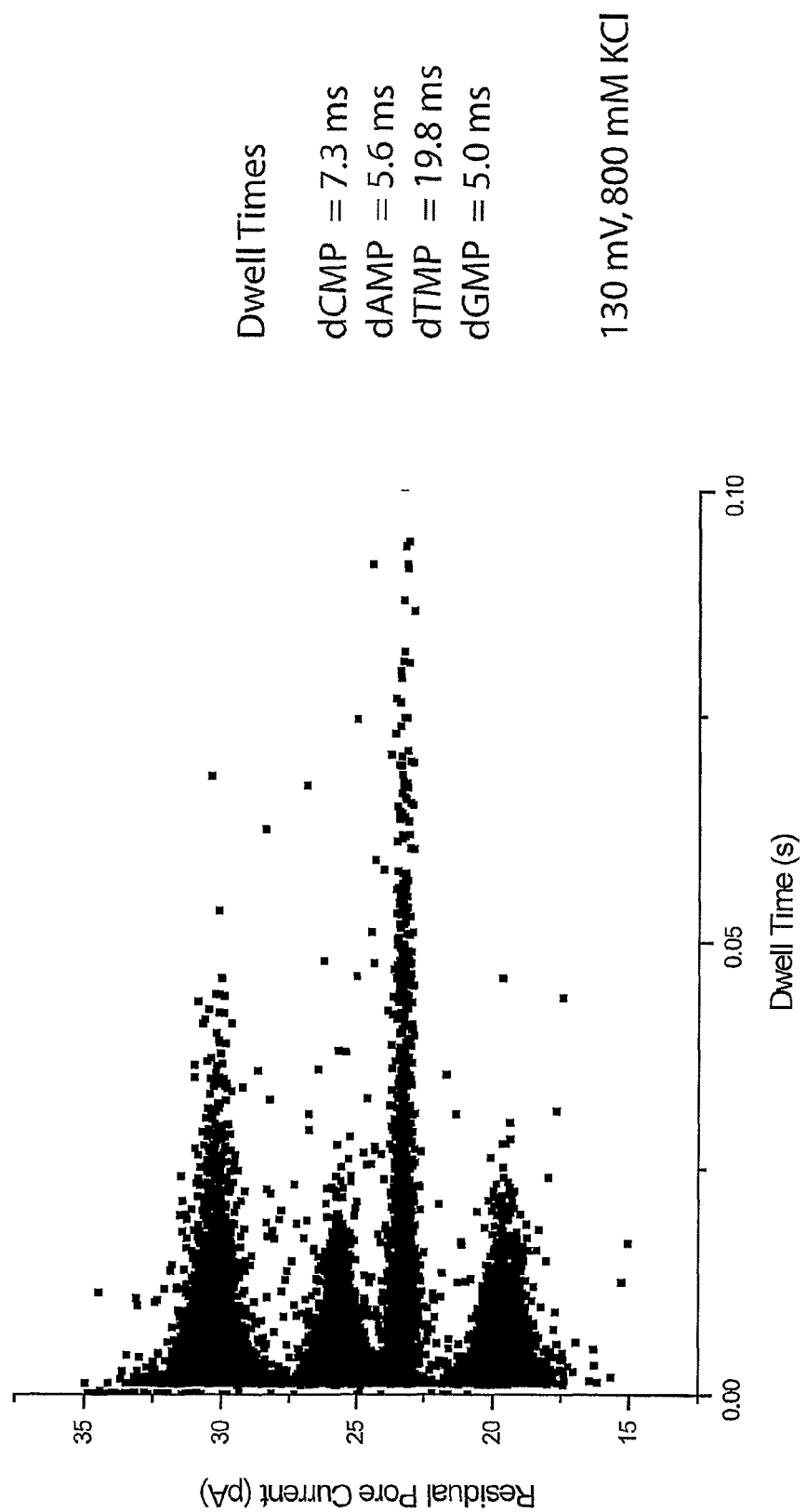
FIG. 20 shows the dwell time versus mean of residual pore current. Peaks from all four bases (G T A C, bottom to top) can be seen, as can the longer average dwell time of dTMP.

One feature of these plots is the sharpness of the dTMP peak. The dTMP binding is distinct from the other four bases in having a longer binding time in the construct (dwell time). This can be easily seen by plotting the dwell time of an event against the mean of the residual current through the modified pore (FIG. 20).

On average, the longer dwell time of the dTMP results in a larger number of data points being collected for each binding event. As the accuracy of the residual pore current is calculated from a mean of the data points, the more data points in an event, the more accurate the mean and hence the smaller the distribution of events in the residual current histogram. A long binding time is desirable for sequencing applications as the probability of dNMP misreads are reduced.

2.7 Low Salt Operating Conditions

All the data presented above was acquired at relatively high concentrations of salt, this is desirable as a high solution conductance increases the signal to noise ratio and allows the signals to be easily identified against a background of pore fluctuations. However, for sequencing applications, the base detection must operate under conditions that are favourable for enzyme function in order for dNMPs to be liberated from DNA.

Figure 21:
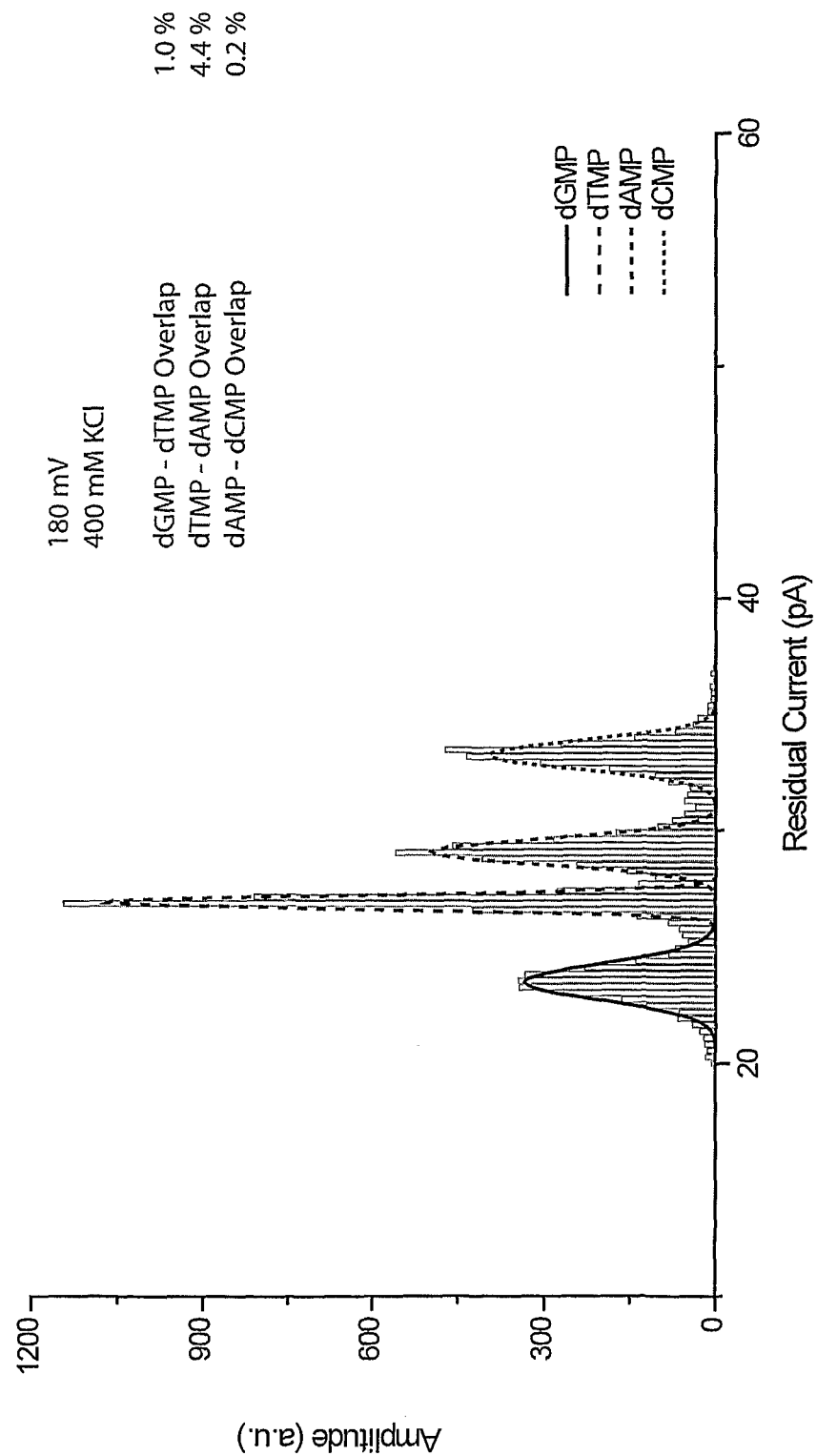
FIG. 21 shows a histogram for the HL-(M113R/N139Q)$_6$(M113R/N139Q/L135C-D8)$_1$ mutant. Good base discrimination can be seen at low salt (400 mM KCl, 180 mV, pH 7.5).

A series of salt conditions were investigated to find the lower limit for nucleotide detection and discrimination to favour enzyme operating conditions. Initial investigations focused at 500 mM, at this concentration of KCl, there appeared to be little difference in the base resolution compared to the 800 mM KCl runs (data not shown). Further studies conducted at 400 mM KCl showed that the four dNMP bases could be easily resolved with little increase in the overlap of current states, however the reduction in salt did effect the relative position of the four peaks, and a slightly higher applied potential was required to obtain the best peak separation (FIG. 21).

Figure 22:
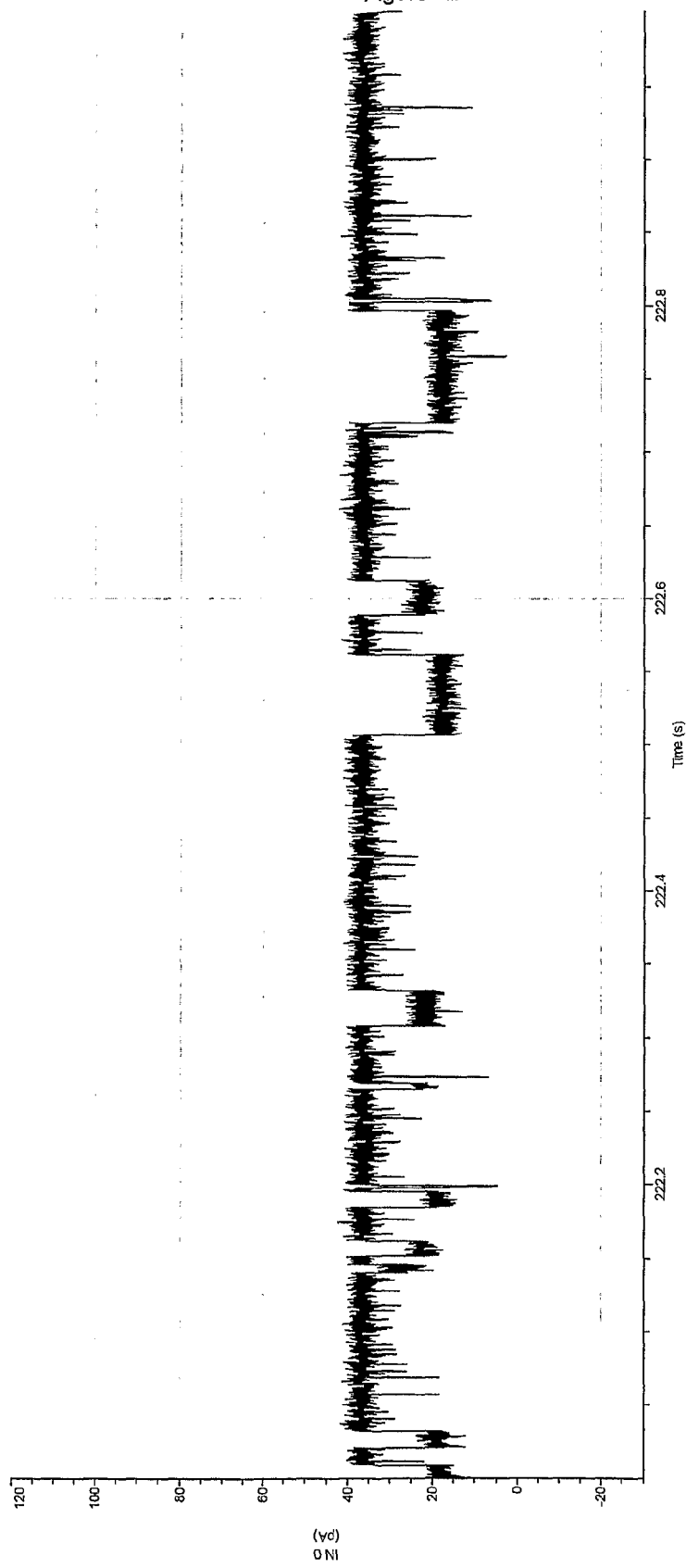
FIG. 22 shows single channel recording of the HL-(M113R/N139Q)$_6$(M113R/N139Q/L135C-D8)$_1$ mutant (5 kHz software filtered) reacted with the am$_6$amPDP$_1$-βCD after dNMPs were added (350 mM KCl, 180 mV, pH 7.5).

Having achieved a good baseline for experiments at low salt, the concentration of salt was further reduced to 300 and 350 mM. The runs at 350 mM did show relatively good base discrimination and four peaks could be distinguished, however, the signal to noise was low and peak picking the nucleotide events near the cyclodextrin level (dCMP binding) was challenging (FIG. 22).

Figure 23:
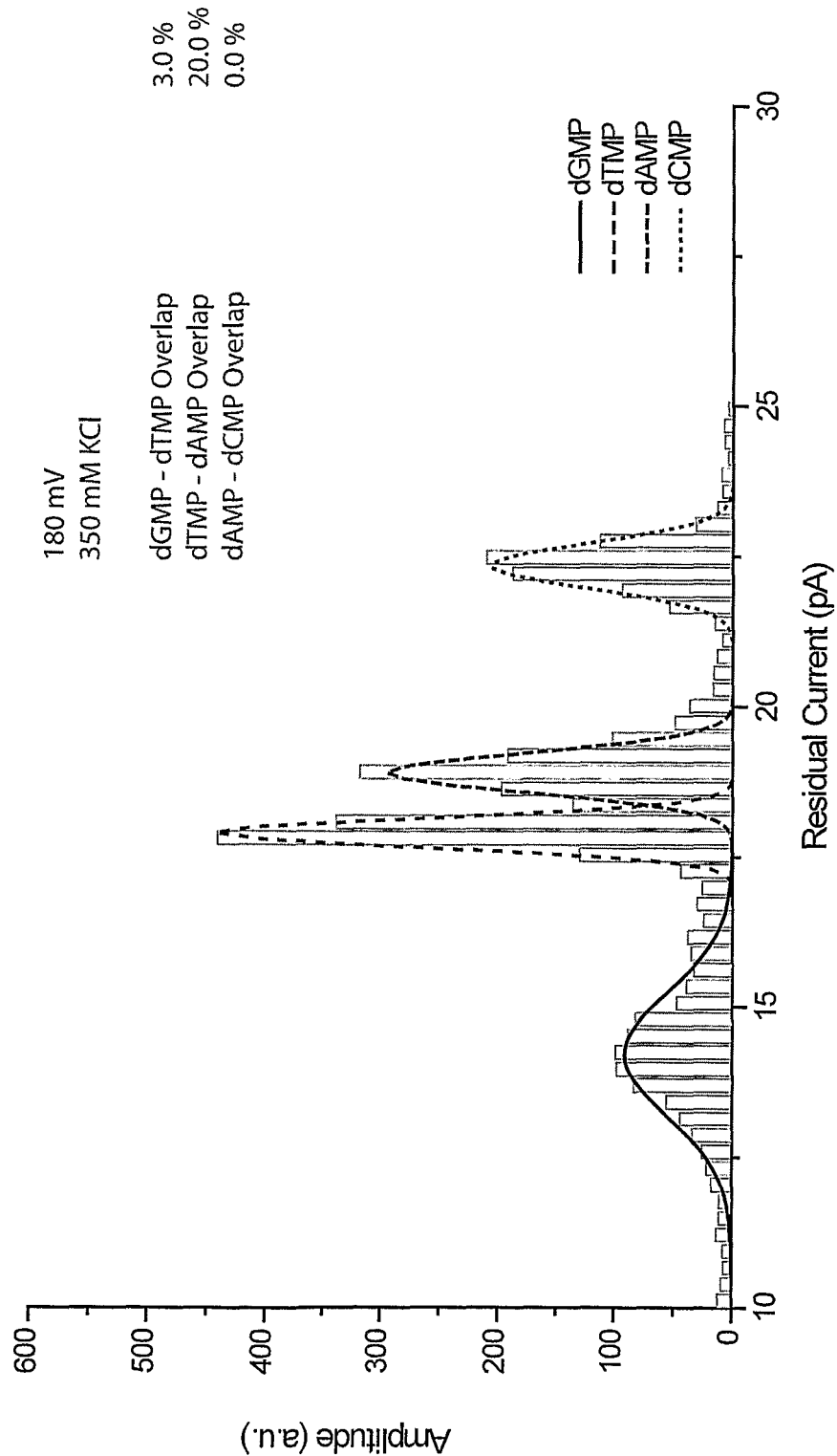
FIG. 23 shows a histogram for the HL-(M113R/N139Q)$_6$(M113R/N139Q/L135C-D8)1 mutant. Good base discrimination can be seen at low salt (350 mM KCl, 180 mV, pH 7.5).

As the four peaks could be easily resolved in a residual current histogram, each peak was fitted to a Gaussian and the overlaps calculated (FIG. 23). The peak overlap was slightly higher than the 400 mM KCl, showing a 20% area of overlap between the dTMP and dAMP, however, the other nucleotides were well resolved.

The salt concentration was further reduced to 300 mM KCl and run under the same conditions. Although base detection was achieved, the discrimination between the dNMPs was poor.

Different parameters were used for the data analysis, but the base resolution could not be improved. Although the reduction in salt leads to low conductivity and hence makes the base detection difficult, the position of the peaks and the large differences between the spectrum at 300 mM and 350 mM suggests that the change in salt may have effected the mechanism of base binding.

Figure 24:
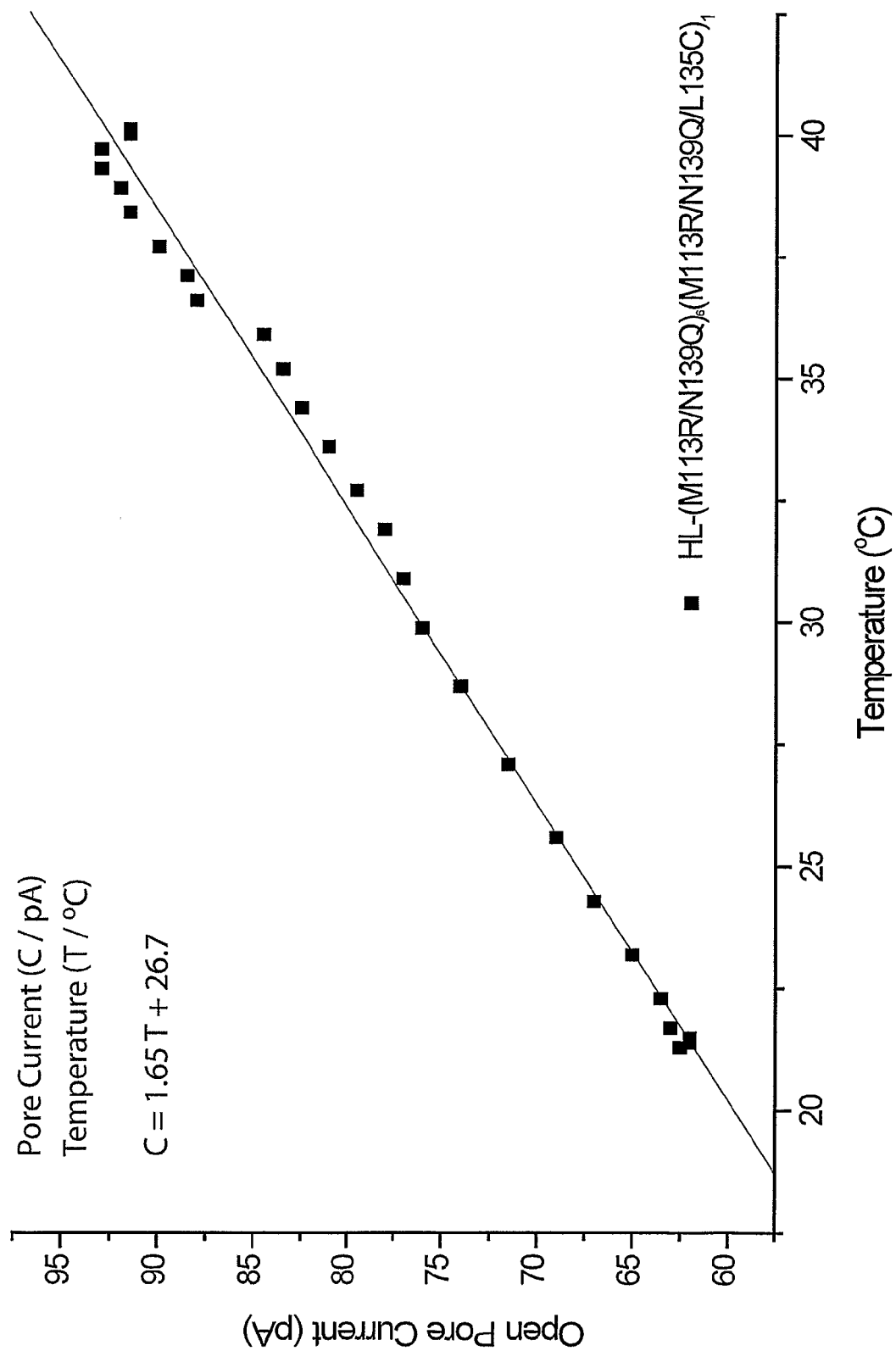
FIG. 24 shows a plot of hemolysin conductance versus solution temperature for a single channel in 300 mM KCl, 25 mM Tris, starting pH 7.5. An increase of 1.65 pA/° C. can be seen.

One way to increase the conductance is to raise the temperature of the solution. This has the added benefit of increasing the enzyme activity if the temperature is close to physiological conditions. To quantity the changes in solution conductance with temperature, the current through a single HL-(M113R/N139Q)$_6$(M113R/N139Q/L135C-D8)$_1$ mutant was measured as the temperature of a 300 mM solution was increased (FIG. 24).

Figure 25:
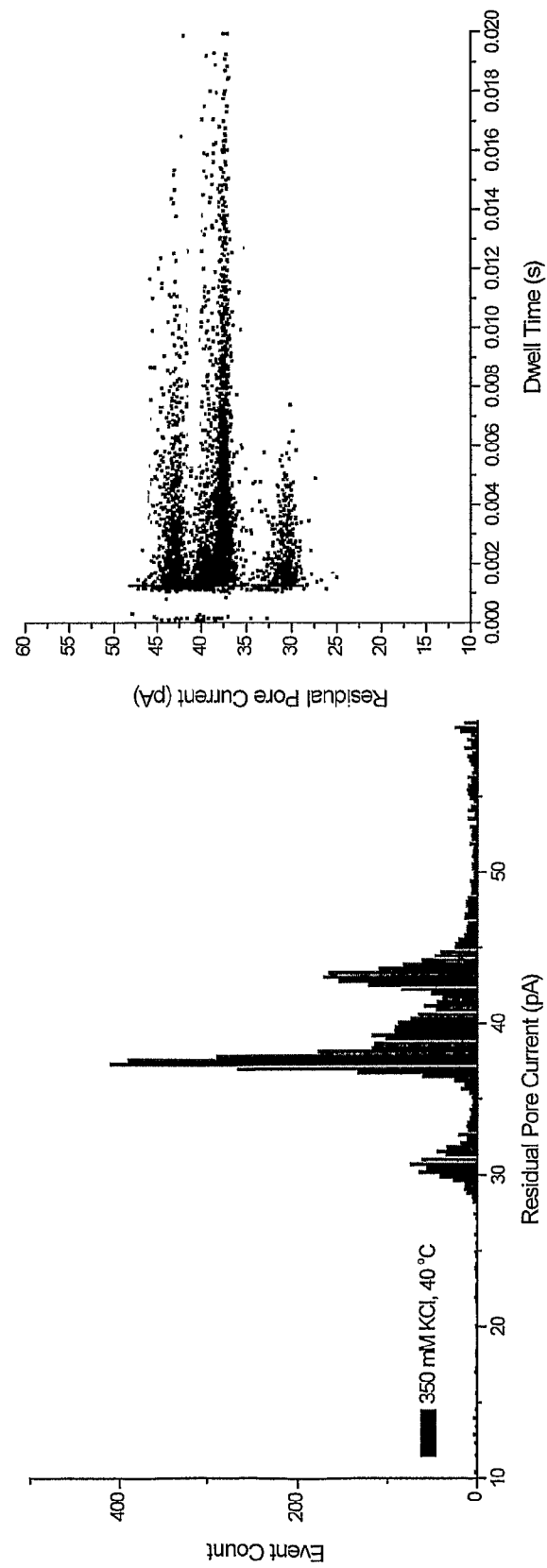
FIG. 25 shows a histogram for the HL-(M113R/N139Q)$_6$(M113R/N139Q/L135C-D8)$_1$ mutant showing good base detection at low salt and elevated temperature (300 mM KCl, 180 mV, pH 7.2, 40° C.) (left) and a plot of dwell time versus amplitude of the same data showing a short dwell time (right).

Increasing the solution temperature from 25 to 40° C. results in a change in pore conductance from 62.5 pA to 91.5 pA (46% increase in pore conductance). The base detection experiment at 300 mM KCl was repeated to examine the effects of temperature on the base discrimination (FIG. 25).

A clear difference between the residual current histograms at 40° C. and room temperature is the broadness in the distribution. This effect can be attributed to a reduction in the nucleotide dwell time at elevated temperatures (average dwell time of 2 ms at 40° C. compared to 9.4 ms at room temperature). As the accuracy of calculating the mean current level of a single binding event is related to the number of data points, the distribution of current levels becomes larger with shorter dwell times. Additionally, as the dwell time is reduced, the number of nucleotide binding events that are too short to observe is increased, requiring faster data acquisition rates to capture the same number of events.

In summary, the HL-(M113R/N139Q)$_6$(M113R/N139Q/L135C-D8)$_1$.am$_6$amPDP$_1$-βCD construct shows a wide range of operating conditions, some of which may be suitable for DNA processing enzymes, such as exonucleases. The salt concentration can be reduced to 350 mM at room temperature with good base discrimination and lower salt concentrations can be used if the temperature is increased, or if asymmetric salt conditions are employed.

2.8 Detection of Methyl-dCMP

In addition to the four nucleosides discussed above, there has been growing interest in the scientific community over the role of 5-methylcytosine (methyl-dCMP), a chemical change in the DNA structure that does not effect the base pairing properties (FIG. 26).

The presence of methyl-dCMP is important for epigenetics as spontaneous deamination of unmethylated cytosine forms uracil, which is recognized and removed by DNA repair enzymes, but when the dCMP is methylated, deamination results in thymine. This conversion of C to T can result in a transition mutation and is therefore of great importance to the understanding of genetic disease.

Figure 27:
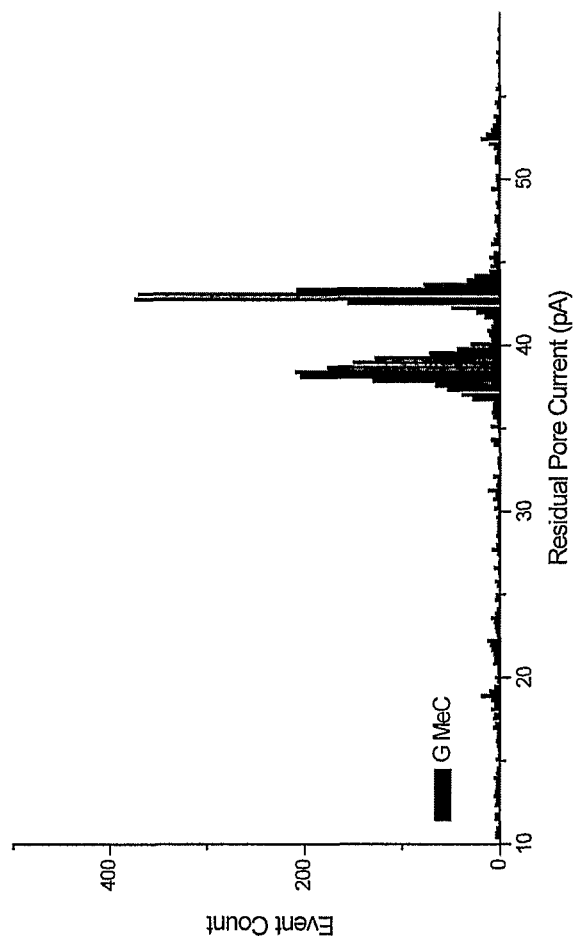
FIG. 27 shows a histogram for the HL-(M113R/N139Q)$_6$(M113R/N139Q/L135C-D8)$_1$ mutant. dGMP and methyl-dCMP base detection can be seen (800 mM KCl, 180 mV, pH 7.5).

The HL-(M113R/N139Q)$_6$(M113R/N139Q/L135C-D8) 1.am$_6$amPDP$_1$-βCD construct was used to see if methyl-dCMP could be detected with this technique. Initially methyl-dCMP was added to a solution containing dGMP as an internal calibrant (FIG. 27). Two distinct populations can be seen, one which corresponds to the known dGMP distribution, and the other from the binding of methyl-dCMP.

Having demonstrated that our baseline construct can detect methyl-dCMP and confirmed the peak position of this species, a solution containing all five nucleoside monophosphates (dGMP, dTMP, dAMP, dCMP and Methyl-dCMP) was tested and the physical conditions optimised. The optimal potential to achieve the lowest base overlap at 800 mM KCl was found to be 170 mV. This was then compared to a run containing the four standard nucleotides (no methyl-dCMP present) (FIG. 28).

Figure 29:
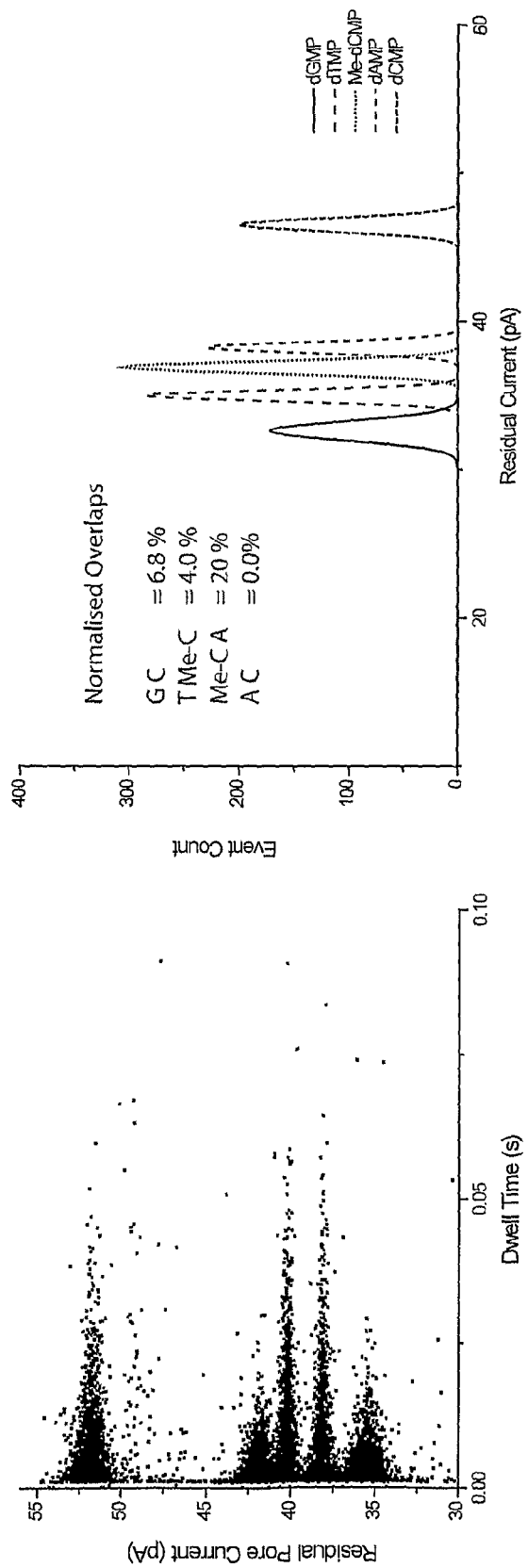
FIG. 29 shows dwell time versus mean of residual pore current. Peaks from all four bases and methyl-dCMP (left) and the Gaussian fits of the residual current histograms for the five bases (right) can be seen.

The dwell time of each event was plotted against the residual pore current to show the binding affinity of methyl-dCMP compared to the standard four bases (FIG. 29). This showed a longer dwell time for methyl-dCMP, which was more comparable to dTMP than dCMP. This suggests that the methyl group present in both dTMP and methyl-dCMP (FIG. 26) is important to long cyclodextrin binding.

Figure 30:
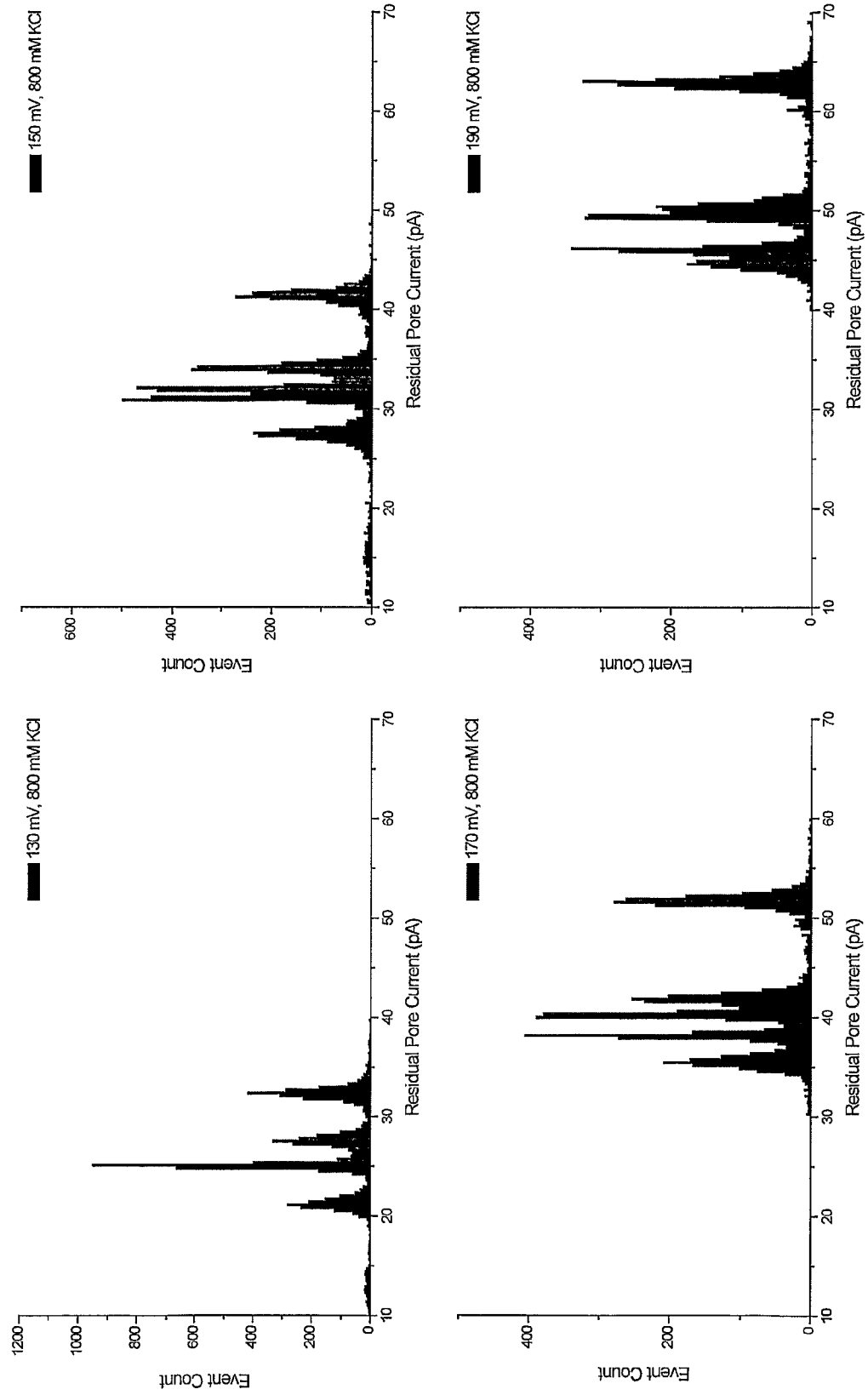
FIG. 30 shows the residual current histograms of dNMP binding for the HL-(M113R/N139Q)$_6$(M113R/N139Q/L135C-D8)$_1$ mutant at a range of applied potentials (130-170 mV). The changes in the relative positions of the four nucleotides with methyl-dCMP added can be seen.
Figure 33:
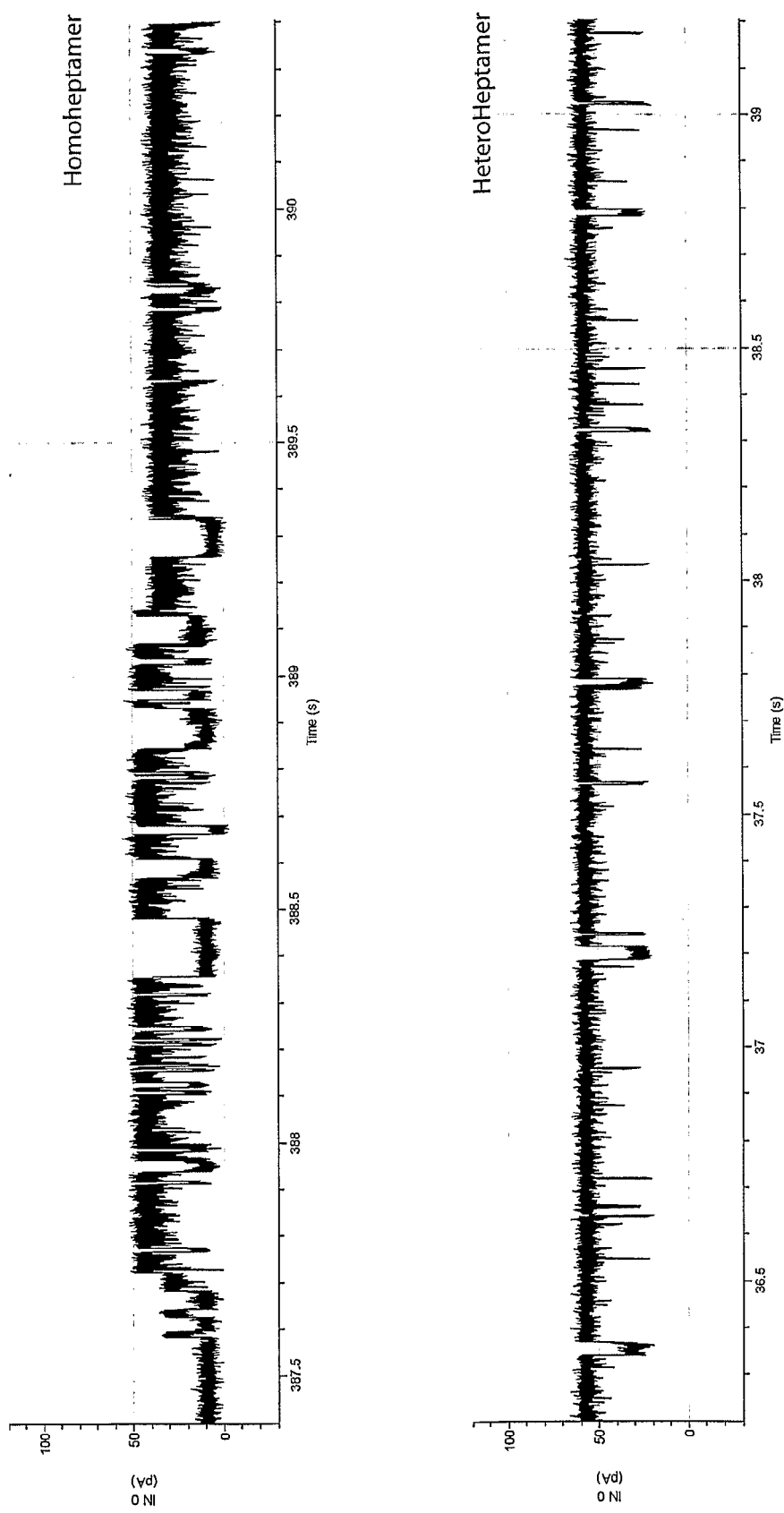
FIG. 33 shows single channel recordings for the homo-heptamer HL-(M113R/N139Q/N121C)$_7$ with am$_6$amPDP$_1$-βCD reacted at the 121 position.

All five nucleosides monophosphate peaks were fitted to Gaussians and the percentage of area overlap calculated (FIG. 33). The Gaussian overlaps for detection of all four bases was good, although a relatively large overlap was seen between Methyl-dCMP and dAMP. Again, the relative position of each of the bases could be controlled by varying the magnitude of the applied potential (FIG. 30).

The ability to detect methyl-dCMP is important for a wide range of applications, but is very difficult to achieve with conventional technologies. One reason for this is that many current strategies rely on amplifying the concentration of DNA with PCR or other common techniques. In amplifying the DNA, any methyl-dCMP will be converted to dCMP and hence information is lost. In contrast to many other technologies, nanopore sensing is a single molecule system and therefore has the potential to be used without amplifying DNA, making it the perfect candidate for extracting epigenetic information.

2.9 RNA Base Detection

The data presented on the baseline construct has so far been focused on the dNMP bases which are components of DNA, however, this system has the capacity to examine other nucleotides, in particular the ribose bases found in RNA. These bases differ from the corresponding dNMPs in two ways; the sugar unit contains an additional hydroxyl group and uracil replaces the thymine base (uracil being the unmethylated version of thymine) (FIG. 31).

Figure 32:
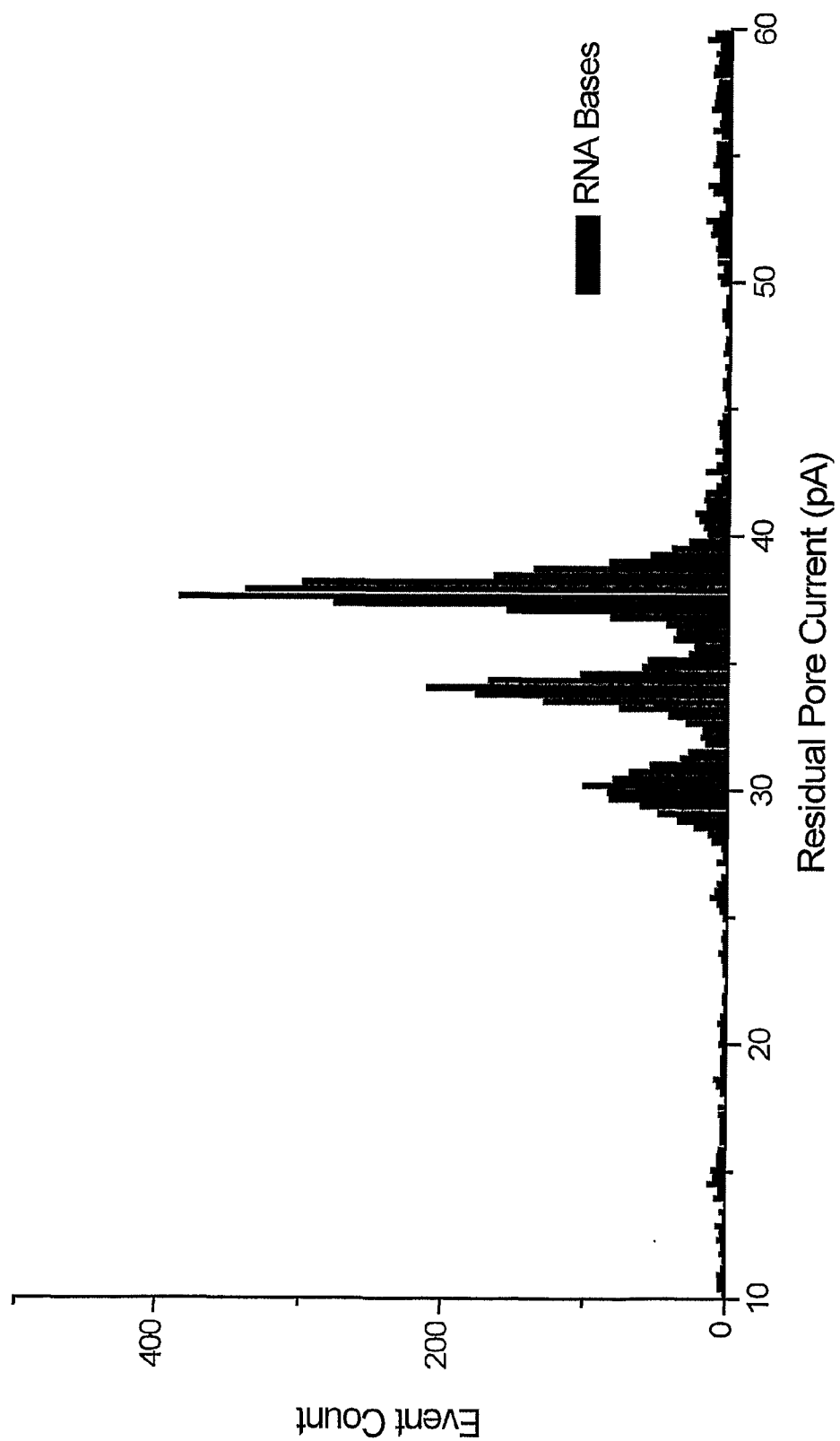
FIG. 32 shows the histogram for the HL-(M113R/N139Q)$_6$(M113R/N139Q/L135C-D8)$_1$ mutant. NMP base detection can be seen (800 mM KCl, 160 mV, pH 7.5)=.

The four main RNA bases, adenosine monophosphate (AMP), guanosine monophosphate (GMP), uridine monophosphate (UMP) and cytidine monophosphate (CMP) were testing using the HL-(M113R/N139Q)$_6$(M113R/N139Q/L135C-D8)$_1$.am$_6$amPDP$_1$-βCD construct to see if these species could be discriminated from each other. The first conditions chosen were the optimal conditions for the dNMP bases (800 mM KCl, 160 mV, pH 7.5). These results were plotted in a residual current histogram (FIG. 32).

The preliminary results for RNA base detection are good; with no specific optimisation for these bases, the histogram stilled shows three clear distributions. The identify of these peaks has yet to be verified, however, it seems likely that the order is similar to the dNMP bases under these conditions, with GMP showing the largest pore block (30 pA residual current), followed by AMP (34 pA residual current), with the smallest block resulting from CMP (38 pA residual current). The chemical structure of the uridine monophosphate is very similar to that of cytidine monophosphate and it seems likely that they could give rise to a similar level of pore blockage.

2.10 Hetero-Heptamer Versus Homo-Heptamer

A limiting factor in performing these experiments is the amount of time that the am$_6$amPDP$_1$-βCD takes to react, with some protein pores never reacting with the cyclodextrin. One explanation for this is that the single cysteine residues on the protein heteroheptamer has reacted with a contaminant, or oxidised. Once this occurs, it is difficult to restore the activity of this functional group.

One solution to this is to increase the number of cysteine groups in the pore. This can be done by changing the number of modified monomers in the heptamer, up to all seven resides. When all seven monomers of the heptamer complex are identical, the protein is referred to as a homo-heptamer (Table 5).

TABLE 5

Hetero-heptamers and corresponding homo-heptamers used in this study

| Position | Hetero-Heptamer | Homo-Heptamer |
| --- | --- | --- |
| 121 | HL-(M113R/N139Q)$_6$(M113R/N139Q/N121C-D8)$_1$ | HL-(M113R/N139Q/N121C)$_7$ |
| 123 | HL-(M113R/N139Q)$_6$(M113R/N139Q/N123C-D8)$_1$ | HL-(M113R/N139Q/N123C)$_7$ |
| 125 | HL-(M113R/N139Q)$_6$(M113R/N139Q/G125C-D8)$_1$ | HL-(M113R/N139Q/G125C)$_7$ |
| 133 | HL-(M113R/N139Q)$_6$(M113R/N139Q/T133C-D8)$_1$ | HL-(M113R/N139Q/T133C)$_7$ |
| 135 | HL-(M113R/N139Q)$_6$(M113R/N139Q/L135C-D8)$_1$ | HL-(M113R/N139Q/L135C)$_7$ |
| 137 | HL-(M113R/N139Q)$_6$(M113R/N139Q/G137C-D8)$_1$ | HL-(M113R/N139Q/G137C)$_7$ |

The homo-heptamers were reacted with the am$_6$amPDP$_1$-βCD and compared to the corresponding hetero-heptamers (FIG. 33). In general, the homo-heptamer pores showed much greater variability than the corresponding hetero-heptamers. Although most of these constructs reacted with the modified cyclodextrin, the homo-heptamers suffered from increased baseline fluctuations and it was difficult to obtain good base discrimination over the "noise" of the baseline.

One possible explanation for this is the chemical state of the other six un-reacted cysteines. Each of these groups could be in a number of different oxidation states. When oxidised, the cysteine group can take following forms; sulphenic acid (R—SOH), sulphinic (R—SO2-), or sulphonic (R—SO32-). Although the higher oxidation states are rare, the formation of such species can be catalysed by adjacent positively charged groups, such as the primary amines of the modified cyclodextrin. When oxidised, the cysteines are likely to interact with the positive charged groups of the cyclodextrin and affect the observed pore current.

2.11 Mechanistic Evaluation of the Biosensor

In order to better understand the baseline construct, a series of mutants were made to test each of the individual components of the protein when an adapter is attached at the L135C residue (Table 6). The series of proteins contained a mutant which lacks the arginines at the 113 residue, a mutant which lacks the glutamines at the 139 residue. In addition, the baseline mutant was tested with a chemically modified adapter that is capable of reacting with the pore, but lacks the primary amines of the am$_6$amPDP$_1$-βCD compound.

Figure 34:
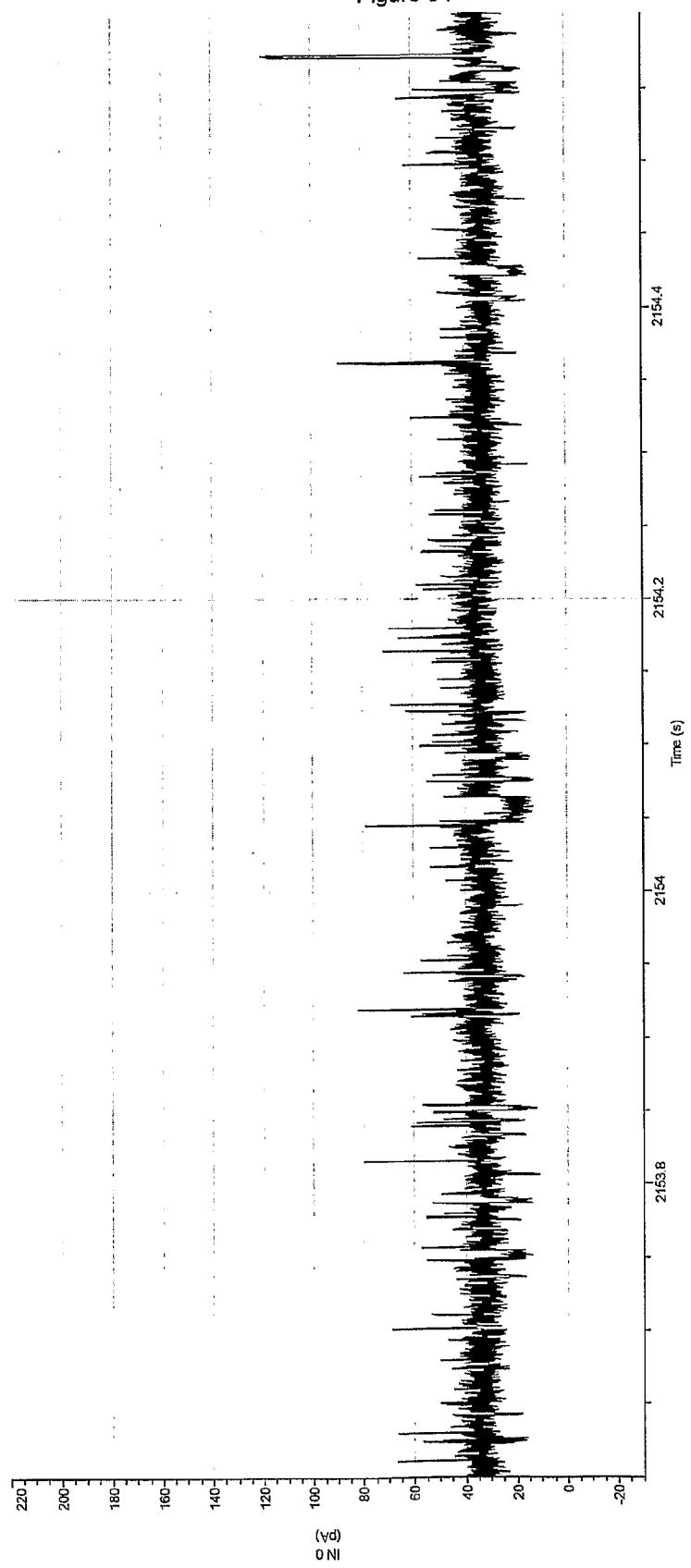
FIG. 34 shows single channel recording of the HL-(M113R/N139Q)$_6$(M113R/N139Q/L135C-D8)$_1$ mutant (5 kHz software filtered) reacted with the PDP$_1$-βCD after dGMP, dTMP, dAMP nd dCMP was added (800 mM KCl, pH 7.5, 160 mV, 5 kHz filter, 0.5 seconds shown).
Figure 35:
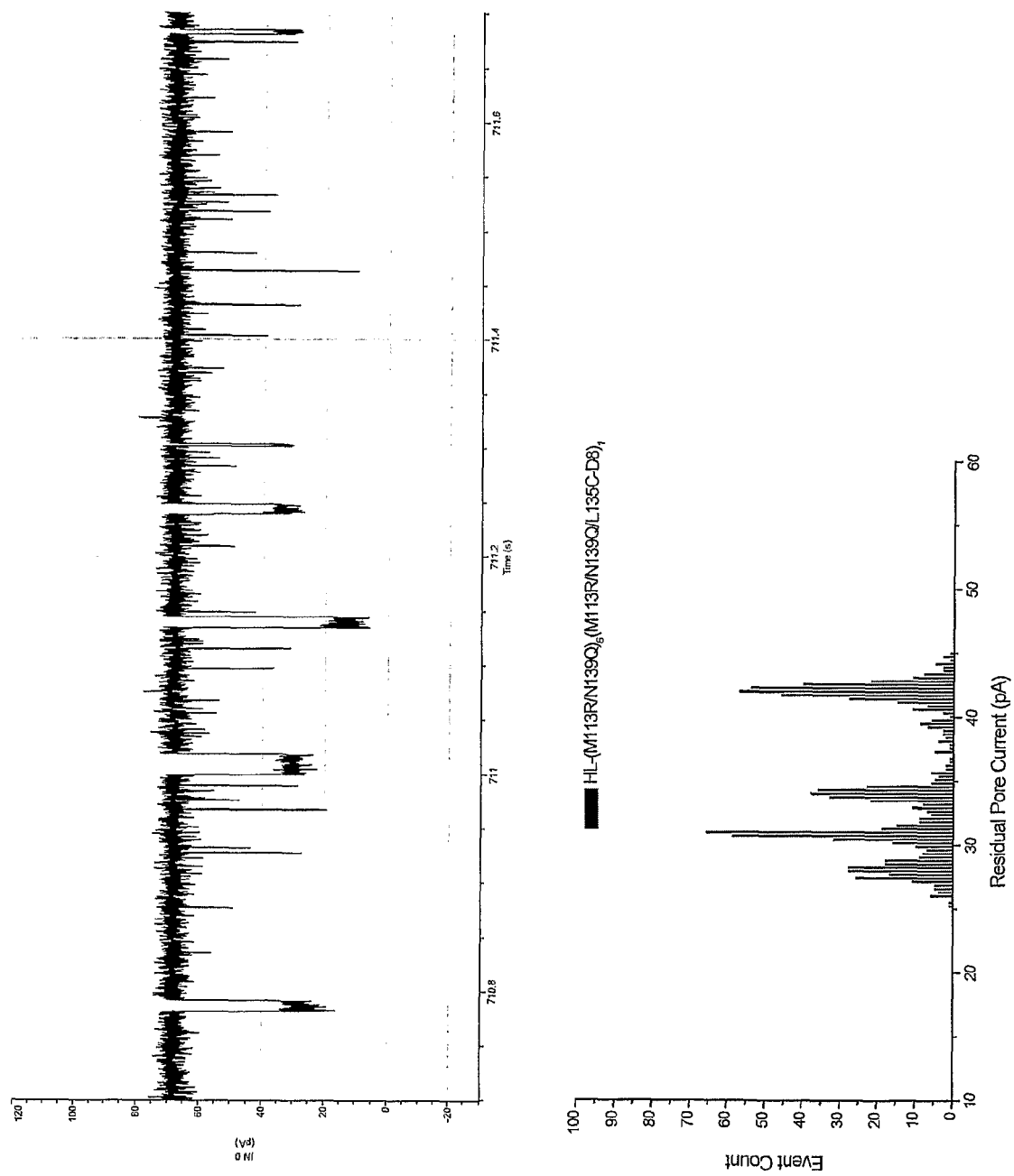
FIG. 35 shows single channel recording of the HL-(M113R/N139Q)$_6$(M113R/N139Q/L135C-D8)$_1$ mutant (5 kHz software filtered) reacted with the am$_6$amPDP$_1$-βCD after dGMP, dTMP, dAMP and dCMP was added (800 mM KCl, pH 7.5, 160 mV, 5 kHz filter, 0.5 seconds shown).

PDP$_1$-βCD (FIG. 34) and the other used the standard am$_6$amPDP1-βCD cyclodextrin (FIG. 35).

It is clear that the primary amine groups of the am$_6$-amPDP$_1$-βCD adapter are required for high resolution detection of dNMPs. The large change in the conductance between the amino-cyclodextrin (68 pA) and the hydroxyl-cyclodextrin (30 pA) demonstrates that the primary amines play a part in stabilising the reacted cyclodextrin compound. It also seems likely the charged amine groups can interact directly with the bases during binding.

Figure 36:
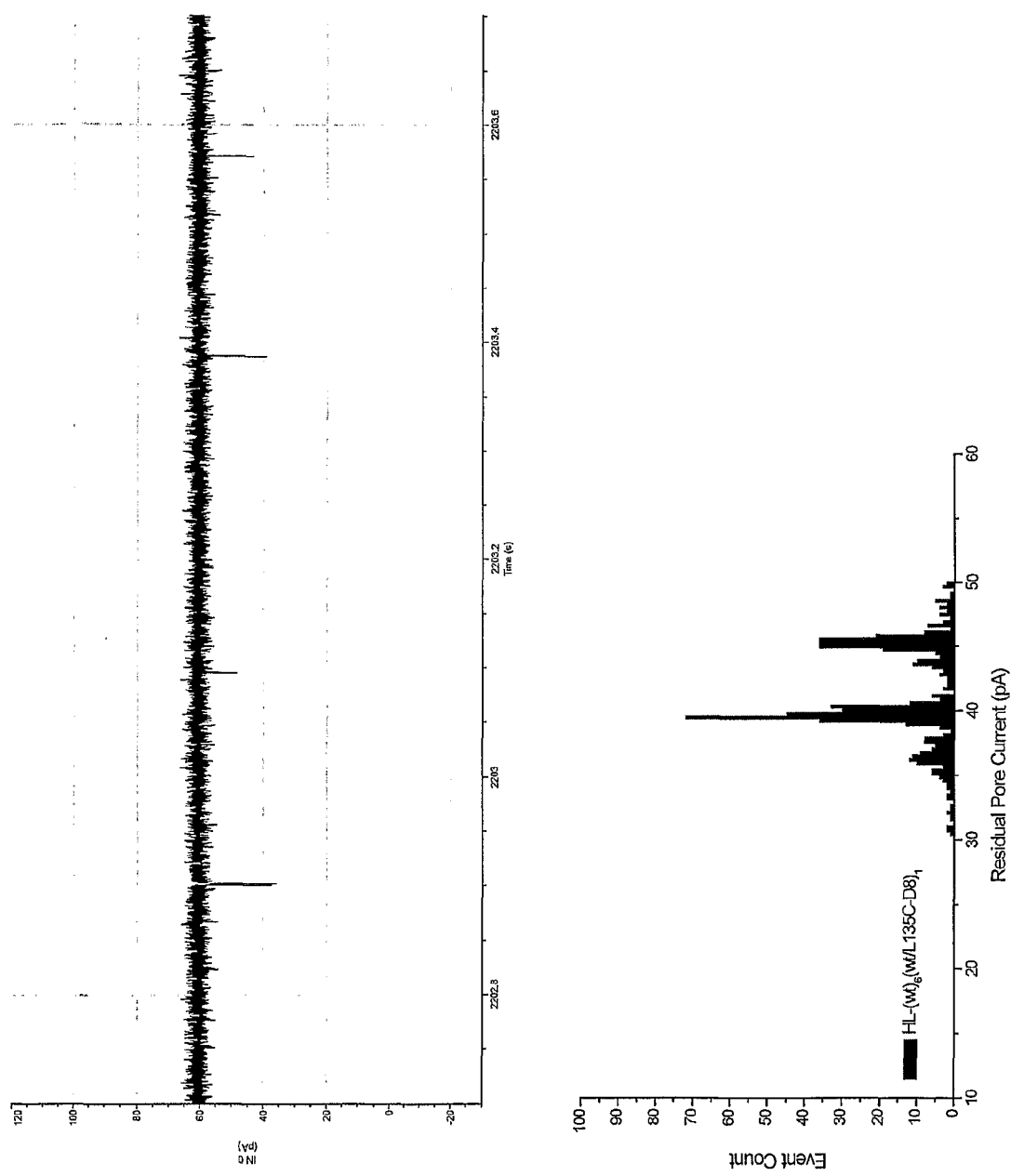
FIG. 36 shows single channel recording of the HL-(wt)$_6$(L135C-D8)$_1$ mutant (5 kHz software filtered) reacted with the am$_6$amPDP$_1$-βCD after dGMP, dTMP, dAMP and dCMP was added (800 mM KCl, pH 7.5, 160 mV, 5 kHz filter, 0.5 seconds shown) and the corresponding residual current histogram.

The next construct tested lacked both the arginines at the 113 residue and the glutamines at the 139 residue, but still kept the cyclodextrin attachment site at the L135C position. This mutant is essentially the wild-type protein, with a single cysteine. The amino-cyclodextrin was used and reacted well, however, the reacted level showed greater fluctuations than the baseline construct, even before the addition of nucleotides. Upon addition of all four standard nucleoside monophosphates some binding events were seen, but these were infrequent and discrimination between the bases was not possible (FIG. 36).

This shows that the arginines, the glutamines, or both mutations are required for accurate base discrimination. In order to determine this, a variant of the baseline mutant lacking the N139Q mutation was tested. This mutant is similar to the wild-type pore, but with a ring of arginines at the β-barrel constriction and a single cysteine for attachment of the cyclodextrin at the L135C position. The positively charged arginines are expected to interact with the negatively charged dNMPs, but may also influence the charges on the amino-cyclodextrin which may in turn affect the baseline signal.

TABLE 6

Mutants designed for the mechanistic study of the baseline construct

| Mutant Name | Cyclodextrin | Testing |
| --- | --- | --- |
| HL-(M113R/N139Q)$_6$(M113R/N139Q/L135C-D8)$_1$ | am$_6$amPDP$_1$-βCD | Baseline Construct |
| HL-(M113R/N139Q)$_6$(M113R/N139Q/L135C-D8)$_1$ | amPDP$_1$-βCD | Need for amines on the adapter |
| HL-(wt)$_6$(L135C-D8)$_1$ | am$_6$amPDP$_1$-βCD | Need for Arginines and Glutamines |
| HL-(M113R)$_6$(M113R/L135C-D8)$_1$ | am$_6$amPDP$_1$-βCD | Need for Glutamines at 139 |
| HL-(N139Q)$_6$(N139Q/L135C-D8)$_1$ | am$_6$amPDP$_1$-βCD | Need for Arginines at 113 |

The first modification to be examined was the primary amine groups of the cyclodextrin, the six amines are partially protonated at pH 7.5 and may interact with the negative phosphate group of the dNMP. The amino-cyclodextrin also has other benefits, the dwell time at positive potentials can be enhanced a thousand fold compared to the normal (hydroxyl) β-cyclodextrin. This increase in dwell time is helpful but not needed with covalent attachment of the adaptor.

Figure 37:
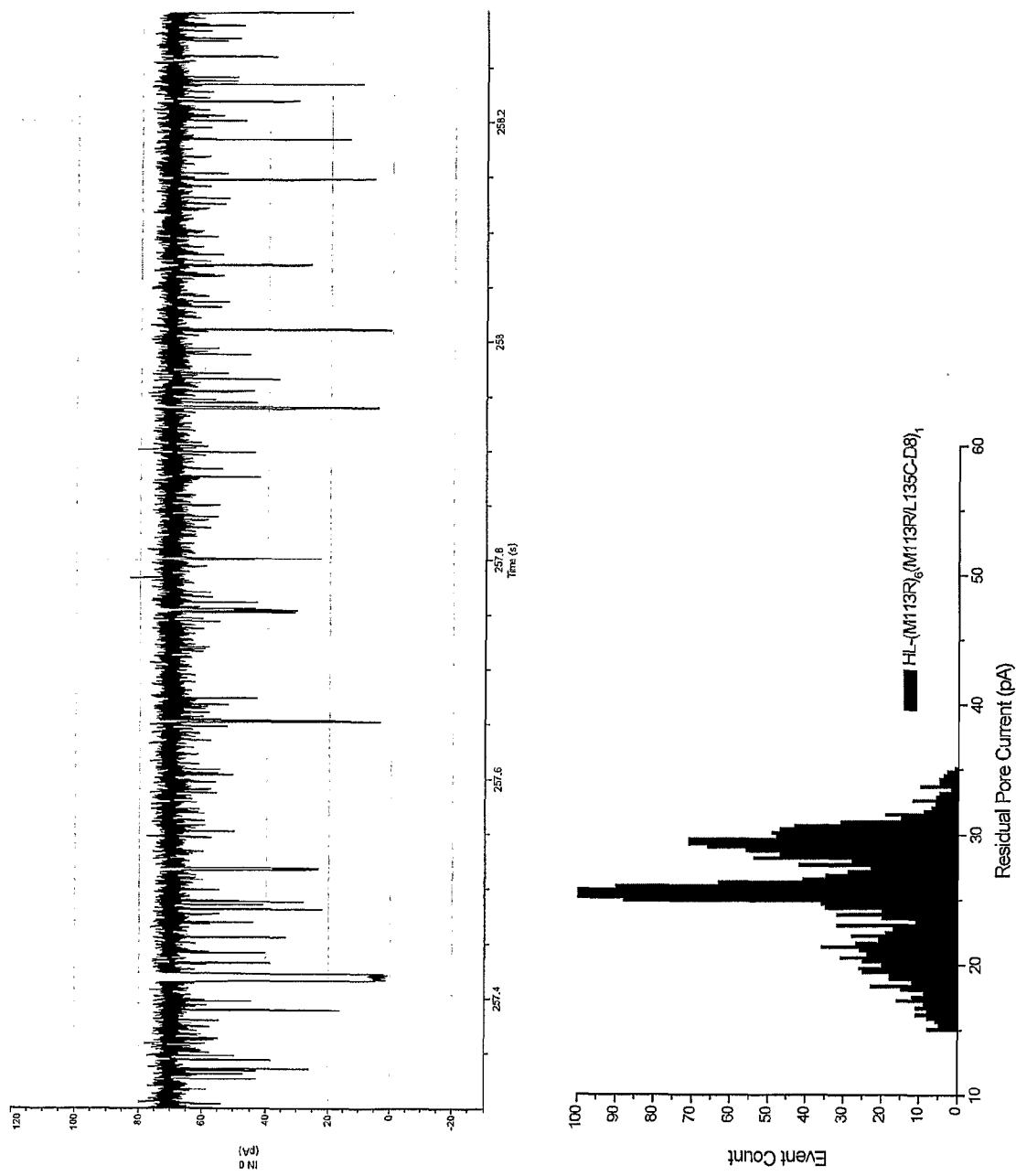
FIG. 37 shows single channel recording of the HL-(M113R)$_6$(M113R/L135C-D8)$_1$ mutant (5 kHz software filtered) reacted with the am$_6$amPDP$_1$-βCD after dGMP, dTMP, dAMP and dCMP was added (800 mM KCl, pH 7.5, 160 mV, 5 kHz filter, 0.5 seconds shown) and the corresponding residual current histogram.

The baseline mutant pore was tested under optimal conditions (800 mM KCl, pH 7.5, 160 mV), one run used the The reacted HL-(M113R)$_6$(M113R/L135C-D8)$_1$ mutant did show a cleaner baseline than the HL-(wt)$_6$(L135C-D8)$_1$ mutant after reaction with the amino-cyclodextrin. The addition of nucleotides caused binding events to be observed and additional spikes in the baseline were also observed. The binding was more frequent than the wild-type analogue, suggesting that the arginines may interact with the nucleotides. The residual current of nucleotide binding events was varied and the discrimination between bases was poor when plotted in a residual current histogram (FIG. 37).

One reason for this may be the stability of the attached cyclodextrin, the HL-(M113R)$_6$(M113R/L135C-D8)$_1$ mutant lacks the glutamines at the 139 position, which can hydrogen bond to the secondary hydroxyl face of the cyclodextrin and stabilise the construct. This data shows that, in order to achieve high resolution separation between the nucleotides, the cyclodextrin must be stabilised, this can be achieved with a hydrogen bonding residue, such as glutamines or asparagines.

The next protein to be tested was the HL-(N139Q)$_6$ (N139Q/L135C-D8)$_1$ mutant, which is similar to the baseline construct, but lacks the arginines at the constriction point. This mutant should be able to stabilise the attached amino-cyclodextrin with hydrogen bonding interactions, but may not be able to capture the bases without the charged arginines.

Figure 38:
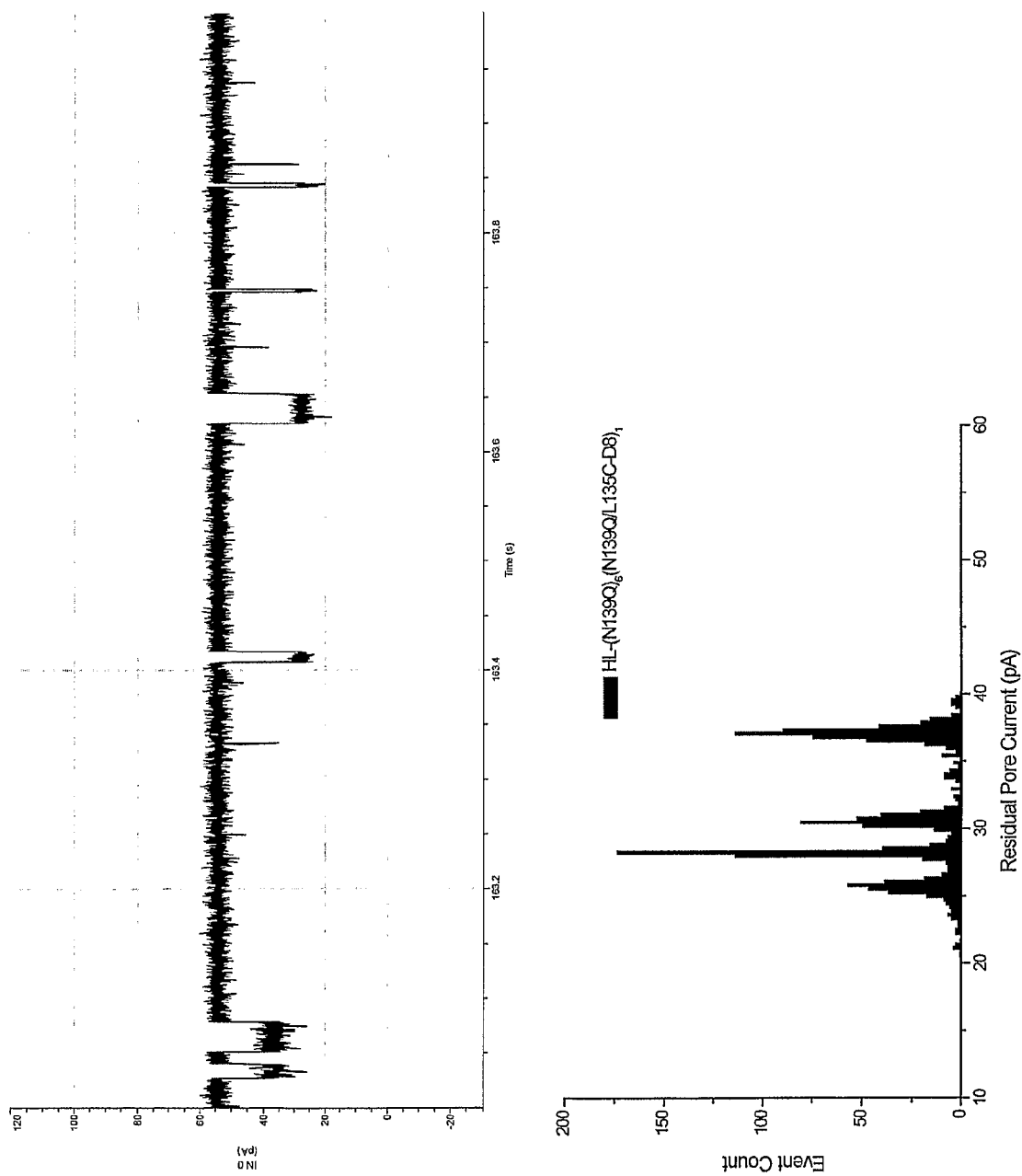
FIG. 38 shows single channel recording of the HL-(N139Q)$_6$(N139Q/L135C-D8)$_1$ mutant (5 kHz software filtered) reacted with the am$_6$amPDP$_1$-βCD after dGMP, dTMP, dAMP and dCMP was added (800 mM KCl, pH 7.5, 160 mV, 5 kHz filter, 0.5 seconds shown) and the corresponding residual current histogram.

The HL-(N139Q)$_6$(N139Q/L135C-D8)$_1$ mutant reacted with the cyclodextrin and gave a very quiet baseline. Upon the addition of bases, binding events could be seen with different amplitudes visible in the raw trace. A histogram of residual pore current showed four distinct peaks, almost identical to the HL-(M113R/N139Q)$_6$(M113R/N139Q/L135C-D8)$_1$ baseline mutant (FIG. 38).

This demonstrates that the arginines are not required to give the four base discrimination seen in the baseline construct. However, they may still influence the performance of the pore. There are a number of additional factors that are involved in the success of the construct; these include the detection rate of nucleotides and the yield for attachment of the adapter to the nanopore.

The arginine groups may help to attract the dNMP bases to the binding site and could increase the capture rate of nucleotides, which is desirable for sequencing applications. However, the arginine side chain is one of the more bulky of the amino acids found in proteins which could limit the capture rate via steric interactions (under investigation).

It is also possible that the arginine groups are involved in promoting the successful reaction of the cyclodextrin. As seen in the non-covalent adapter data, the HL-(M113R/N139Q)$_7$ mutant positions the cyclodextrin near the N139Q residue for base detection, an effect that is not seen when the arginines are removed (data not shown). As the reaction site at the L135C residue is close to the N139Q, then the arginines may aid the reaction of the cyclodextrin. Although infrequent, the cyclodextrin can react at the L135C position, but give a noisy baseline which is incapable of dNMP detection. It is possible that this is linked to the orientation of the cyclodextrin within the pore, which can be influenced by mutation.

Sequence Listing

```
                                                                    SEQ ID NO: 1
  1   ATGGCAGATT CTGATATTAA TATTAAAACC GGTACTACAG ATATTGGAAG CAATACTACA GTAAAAACAG

71   GTGATTTAGT CACTTATGAT AAAGAAAATG GCATGCACAA AAAAGTATTT TATAGTTTTA TCGATGATAA

141   AAATCACAAT AAAAAACTGC TAGTTATTAG AACAAAAGGT ACCATTGCTG GTCAATATAG AGTTTATAGC

211   GAAGAAGGTG CTAACAAAAG TGGTTTAGCC TGGCCTTCAG CCTTTAAGGT ACAGTTGCAA CTACCTGATA

281   ATGAAGTAGC TCAAATATCT GATTACTATC CAAGAAATTC GATTGATACA AAAGAGTATA TGAGTACTTT

351   AACTTATGGA TTCAACGGTA ATGTTACTGG TGATGATACA GGAAAAATTG GCGGCCTTAT TGGTGCAAAT

421   GTTTCGATTG GTCATACACT GAAATATGTT CAACCTGATT TCAAAACAAT TTTAGAGAGC CCAACTGATA

491   AAAAAGTAGG CTGGAAAGTG ATATTTAACA ATATGGTGAA TCAAAATTGG GGACCATACG ATCGAGATTC

561   TTGGAACCCG GTATATGGCA ATCAACTTTT CATGAAAACT AGAAATGGTT CTATGAAAGC AGCAGATAAC

631   TTCCTTGATC CTAACAAAGC AAGTTCTCTA TTATCTTCAG GGTTTTCACC AGACTTCGCT ACAGTTATTA

701   CTATGGATAG AAAAGCATCC AAACAACAAA CAAATATAGA TGTAATATAC GAACGAGTTC GTGATGATTA

771   CCAATTGCAT TGGACTTCAA CAAATTGGAA AGGTACCAAT ACTAAAGATA AATGGACAGA TCGTTCTTCA

841   GAAAGATATA AAATCGATTG GGAAAAAGAA GAAATGACAA AT

SEQ ID NO: 2
  1   ADSDINIKTG TTDIGSNTTV KTGDLVTYDK ENGMHKKVFY SFIDDKNHNK KLLVIRTKGT IAGQYRVYSE

71   EGANKSGLAW PSAFKVQLQL PDNEVAQISD YYPRNSIDTK EYMSTLTYGP NGNVTGDDTG KIGGLIGAQV

141   SIGHTLKYVQ PDFKTILESP TDKKVGWKVI FNNMVNQNWG PYDRDSWNPV YGNQLFMKTR NGSMKAADNF

211   LDPNKASSLL SSGFSPDFAT VITMDRKASK QQTNIDVIYE RVRDDYQLHW TSTNWKGTNT KDKWTDRSSE

281   RYKIDWEKEE MTN

SEQ ID NO: 3
  1   ATGGCAGATT CTGATATTAA TATTGCGACC GGTACTACAG ATATTGGAAG CAATACTACA GTAAAAACAG

71   GTGATTTAGT CACTTATGAT AAAGAAAATG GCATGCACAA AAAAGTATTT TATAGTTTTA TCGATGATAA

141   AAATCACAAT AAAAAACTGC TAGTTATTAG AACAAAAGGT ACCATTGCTG GTCAATATAG AGTTTATAGC

211   GAAGAAGGTG CTAACAAAAG TGGTTTAGCC TGGCCTTCAG CCTTTAAGGT ACAGTTGCAA CTACCTGATA

281   ATGAAGTAGC TCAAATATCT GATTACTATC CGCGGAATTC GATTGATACA AAAGAGTATA GGAGTACGTT
```

```
351 AACGTACGGA TTCAACGGTA ACCTTACTGG TGATGATACT AGTAAAATTG GAGGCCTTAT TGGGGCCCAG
421 GTTTCCCTAG GTCATACACT TAATTATGTT CAACCTGATT TCAAAACAAT TCTCGAGAGC CCAACTGATA
491 AAAAAGTAGG CTGGAAAGTG ATATTTAACA ATATGGTGAA TCAAAATTGG GGACCATACG ATCGAGATTC
561 TTGGAACCCG GTATATGGCA ATCAACTTTT CATGAAGACT AGAAATGGTT CTATGAAAGC AGCAGATAAC
631 TTCCTTGATC CTAACAAAGC AAGTTCCCTA TTATCTTCAG GGTTTTCACC AGACTTCGCT ACAGTTATTA
701 CTATGGATAG AAAAGCATCC AAACAACAAA CAAATATAGA TGTAATATAC GAACGAGTTC GTGATGATTA
771 CCAATTGCAT TGGACTTCAA CAAATTGGAA AGGTACCAAT ACTAAAGATA AATGGACAGA TCGTTCTTCA
841 GAAAGATATA AATCGATTG GGAAAAAGAA GAAATGACAA AT
```

SEQ ID NO: 4
```
  1 ADSDINIATG TTDIGSNTTV KTGDLVTYDK ENGMHKKVFY SFIDDKNHNK KLLVIRTKGT IAGQYRVYSE
 71 EGANKSGLAW PSAFKVQLQL PDNEVAQISD YYPRNSIDTK EYRSTLTYGF NGNLTGDDTS KIGGLIGAQV
141 SLGHTLNYVQ PDFKTILESP TDKKVGWKVI FNNMVNQNWG PYDRDSWNPV YGNQLFMKTR NGSMKAADNF
211 LDPNKASSLL SSGFSPDFAT VITMDRKASK QQTNIDVIYE RVRDDYQLHW TSTNWKGTNT KDKWTDRSSE
281 RYKIDWEKEE MTN
```

SEQ ID NO: 5
```
  1 ATGGCAGATT CTGATATTAA TATTAAAACC GGTACTACAG ATATTGGAAG CAATACTACA GTAAAAACAG
 71 GTGATTTAGT CACTTATGAT AAAGAAAATG GCATGCACAA AAAAGTATTT TATAGTTTTA TCGATGATAA
141 AAATCACAAT AAAAAACTGC TAGTTATTAG AACAAAAGGT ACCATTGCTG GTCAATATAG AGTTTATAGC
211 GAAGAAGGTG CTAACAAAAG TGGTTTAGCC TGGCCTTCAG CCTTTAAGGT ACAGTTGCAA CTACCTGATA
281 ATGAAGTAGC TCAAATATCT GATTACTATC CAAGAAATTC GATTGATACA AAAGAGTATA GGAGTACTTT
351 AACTTATGGA TTCAACGGTA ATGTTACTGG TGATGATACA GGAAAAATTG GCGGCCTTAT TGGTGCAAAT
421 GTTTCGATTG GTCATACACT GAAATATGTT CAACCTGATT TCAAAACAAT TTTAGAGAGC CCAACTGATA
491 AAAAAGTAGG CTGGAAAGTG ATATTTAACA ATATGGTGAA TCAAAATTGG GGACCATACG ATCGAGATTC
561 TTGGAACCCG GTATATGGCA ATCAACTTTT CATGAAAACT AGAAATGGTT CTATGAAAGC AGCAGATAAC
631 TTCCTTGATC CTAACAAAGC AAGTTCTCTA TTATCTTCAG GGTTTTCACC AGACTTCGCT ACAGTTATTA
701 CTATGGATAG AAAAGCATCC AAACAACAAA CAAATATAGA TGTAATATAC GAACGAGTTC GTGATGATTA
771 CCAATTGCAT TGGACTTCAA CAAATTGGAA AGGTACCAAT ACTAAAGATA AATGGACAGA TCGTTCTTCA
841 GAAAGATATA AATCGATTG GGAAAAAGAA GAAATGACAA AT
```

SEQ ID NO: 6
```
  1 ADSDINIKTG TTDIGSNTTV KTGDLVTYDK ENGMHKKVFY SFIDDKNHNK KLLVIRTKGT IAGQYRVYSE
 71 EGANKSGLAW PSAFKVQLQL PDNEVAQISD YYPRNSIDTK EYRSTLTYGF NGNVTGDDTG KIGGLIGANV
141 SIGHTLKYVQ PDFKTILESP TDKKVGWKVI FNNMVNQNWG PYDRDSWNPV YGNQLFMKTR NGSMKAADNF
211 LDPNKASSLL SSGFSPDFAT VITMDRKASK QQTNIDVIYE RVRDDYQLHW TSTNWKGTNT KDKWTDRSSE
281 RYKIDWEKEE MTN
```

SEQ ID NO: 7
```
  1 ATGGCAGATT CTGATATTAA TATTAAAACC GGTACTACAG ATATTGGAAG CAATACTACA GTAAAAACAG
 71 GTGATTTAGT CACTTATGAT AAAGAAAATG GCATGCACAA AAAAGTATTT TATAGTTTTA TCGATGATAA
141 AAATCACAAT AAAAAACTGC TAGTTATTAG AACAAAAGGT ACCATTGCTG GTCAATATAG AGTTTATAGC
211 GAAGAAGGTG CTAACAAAAG TGGTTTAGCC TGGCCTTCAG CCTTTAAGGT ACAGTTGCAA CTACCTGATA
281 ATGAAGTAGC TCAAATATCT GATTACTATC CAAGAAATTC GATTGATACA AAAGAGTATA GGAGTACTTT
351 AACTTATGGA TTCAACGGTA ATGTTACTGG TGATGATACA GGAAAAATTG GCGGCCTTAT TGGTGCACAA
421 GTTTCGATTG GTCATACACT GAAATATGTT CAACCTGATT TCAAAACAAT TTTAGAGAGC CCAACTGATA
491 AAAAAGTAGG CTGGAAAGTG ATATTTAACA ATATGGTGAA TCAAAATTGG GGACCATACG ATCGAGATTC
```

```
561  TTGGAACCCG GTATATGGCA ATCAACTTTT CATGAAAACT AGAAATGGTT CTATGAAAGC AGCAGATAAC
631  TTCCTTGATC CTAACAAAGC AAGTTCTCTA TTATCTTCAG GGTTTTCACC AGACTTCGCT ACAGTTATTA
701  CTATGGATAG AAAAGCATCC AAACAACAAA CAAATATAGA TGTAATATAC GAACGAGTTC GTGATGATTA
771  CCAATTGCAT TGGACTTCAA CAAATTGGAA AGGTACCAAT ACTAAAGATA AATGGACAGA TCGTTCTTCA
841  GAAAGATATA AAATCGATTG GGAAAAAGAA GAAATGACAA AT
```

SEQ ID NO: 8

```
  1  ADSDINIKTG TTDIGSNTTV KTGDLVTYDK ENGMHKKVFY SFIDDKNHNK KLLVIRTKGT IAGQYRVYSE
 71  EGANKSGLAW PSAFKVQLQL PDNEVAQISD YYPRNSIDTK EYRSTLTYGF NGNVTGDDTG KIGGLIGAQV
141  SIGHTLKYVQ PDFKTILESP TDKKVGWKVI FNNMVNQNWG PYDRDSWNPV YGNQLFMKTR NGSMKAADNF
211  LDPNKASSLL SSGFSPDFAT VITMDRKASK QQTNIDVIYE RVRDDYQLHW TSTNWKGTNT KDKWTDRSSE
281  RYKIDWEKEE MTN
```

SEQ ID NO: 9

```
  1  ATGGCAGATT CTGATATTAA TATTAAAACC GGTACTACAG ATATTGGAAG CAATACTACA GTAAAAACAG
 71  GTGATTTAGT CACTTATGAT AAAGAAAATG GCATGCACAA AAAAGTATTT TATAGTTTTA TCGATGATAA
141  AAATCACAAT AAAAAACTGC TAGTTATTAG AACAAAAGGT ACCATTGCTG GTCAATATAG AGTTTATAGC
211  GAAGAAGGTG CTAACAAAAG TGGTTTAGCC TGGCCTTCAG CCTTTAAGGT ACAGTTGCAA CTACCTGATA
281  ATGAAGTAGC TCAAATATCT GATTACTATC CAAGAAATTC GATTGATACA AAAGAGTATA GGAGTACTTT
351  AACTTATTGT TTCAACGGTA ATGTTACTGG TGATGATACA GGAAAAATTG GCGGCCTTAT TGGTGCACAA
421  GTTTCGATTG GTCATACACT GAAATATGTT CAACCTGATT TCAAAACAAT TTTAGAGAGC CCAACTGATA
491  AAAAAGTAGG CTGGAAAGTG ATATTTAACA ATATGGTGAA TCAAAATTGG GGACCATACG ATCGAGATTC
561  TTGGAACCCG GTATATGGCA ATCAACTTTT CATGAAAACT AGAAATGGTT CTATGAAAGC AGCAGATAAC
631  TTCCTTGATC CTAACAAAGC AAGTTCTCTA TTATCTTCAG GGTTTTCACC AGACTTCGCT ACAGTTATTA
701  CTATGGATAG AAAAGCATCC AAACAACAAA CAAATATAGA TGTAATATAC GAACGAGTTC GTGATGATTA
771  CCAATTGCAT TGGACTTCAA CAAATTGGAA AGGTACCAAT ACTAAAGATA AATGGACAGA TCGTTCTTCA
841  GAAAGATATA AAATCGATTG GGAAAAAGAA GAAATGACAA ATGATGACGA TGATGACGAC GATGAT
```

SEQ ID NO: 10

```
  1  ADSDINIKTG TTDIGSNTTV KTGDLVTYDK ENGMHKKVFY SFIDDKNHNK KLLVIRTKGT IAGQYRVYSE
 71  EGANKSGLAW PSAFKVQLQL PDNEVAQISD YYPRNSIDTK EYRSTLTYCF NGNVTGDDTG KIGGLIGAQV
141  SIGHTLKYVQ PDFKTILESP TDKKVGWKVI FNNMVNQNWG PYDRDSWNPV YGNQLFMKTR NGSMKAADNF
211  LDPNKASSLL SSGFSPDFAT VITMDRKASK QQTNIDVIYE RVRDDYQLHW TSTNWKGTNT KDKWTDRSSE
281  RYKIDWEKEE MTNDDDDDDD D
```

SEQ ID NO: 11

```
  1  ATGGCAGATT CTGATATTAA TATTAAAACC GGTACTACAG ATATTGGAAG CAATACTACA GTAAAAACAG
 71  GTGATTTAGT CACTTATGAT AAAGAAAATG GCATGCACAA AAAAGTATTT TATAGTTTTA TCGATGATAA
141  AAATCACAAT AAAAAACTGC TAGTTATTAG AACAAAAGGT ACCATTGCTG GTCAATATAG AGTTTATAGC
211  GAAGAAGGTG CTAACAAAAG TGGTTTAGCC TGGCCTTCAG CCTTTAAGGT ACAGTTGCAA CTACCTGATA
281  ATGAAGTAGC TCAAATATCT GATTACTATC CAAGAAATTC GATTGATACA AAAGAGTATA GGAGTACTTT
351  AACTTATGGA TTCTGTGGTA ATGTTACTGG TGATGATACA GGAAAAATTG GCGGCCTTAT TGGTGCACAA
421  GTTTCGATTG GTCATACACT GAAATATGTT CAACCTGATT TCAAAACAAT TTTAGAGAGC CCAACTGATA
491  AAAAAGTAGG CTGGAAAGTG ATATTTAACA ATATGGTGAA TCAAAATTGG GGACCATACG ATCGAGATTC
561  TTGGAACCCG GTATATGGCA ATCAACTTTT CATGAAAACT AGAAATGGTT CTATGAAAGC AGCAGATAAC
631  TTCCTTGATC CTAACAAAGC AAGTTCTCTA TTATCTTCAG GGTTTTCACC AGACTTCGCT ACAGTTATTA
```

```
701  CTATGGATAG AAAAGCATCC AAACAACAAA CAAATATAGA TGTAATATAC GAACGAGTTC GTGATGATTA
771  CCAATTGCAT TGGACTTCAA CAAATTGGAA AGGTACCAAT ACTAAAGATA ATGGACAGA TCGTTCTTCA
841  GAAAGATATA AAATCGATTG GGAAAAGAA GAAATGACAA ATGATGACGA TGATGACGAC GATGAT
```

SEQ ID NO: 12
```
  1  ADSDINIKTG TTDIGSNTTV KTGDLVTYDK ENGMHKKVFY SFIDDKNHNK KLLVIRTKGT IAGQYRVYSE
 71  EGANKSGLAW PSAFKVQLQL PDNEVAQISD YYPRNSIDTK EYRSTLTYGF CGNVTGDDTG KIGGLIGAQV
141  SIGHTLKYVQ PDFKTILESP TDKKVGWKVI FNNMVNQNWG PYDRDSWNPV YGNQLFMKTR NGSMKAADNF
211  LDPNKASSLL SSGFSPDFAT VITMDRKASK QQTNIDVIYE RVRDDYQLHW TSTNWKGTNT KDKWTDRSSE
281  RYKIDWEKEE MTNDDDDDD D
```

SEQ ID NO: 13
```
  1  ATGGCAGATT CTGATATTAA TATTAAAACC GGTACTACAG ATATTGGAAG CAATACTACA GTAAAAACAG
 71  GTGATTTAGT CACTTATGAT AAAGAAAATG GCATGCACAA AAAAGTATTT TATAGTTTTA TCGATGATAA
141  AAATCACAAT AAAAAACTGC TAGTTATTAG AACAAAAGGT ACCATTGCTG GTCAATATAG AGTTTATAGC
211  GAAGAAGGTG CTAACAAAAG TGGTTTAGCC TGGCCTTCAG CCTTTAAGGT ACAGTTGCAA CTACCTGATA
281  ATGAAGTAGC TCAAATATCT GATTACTATC CAAGAAATTC GATTGATACA AAAGAGTATA GGAGTACTTT
351  AACTTATGGA TTCAACGGTA ATGTTACTGG TGATGATACA GGAAAAATTG GCGGCTGTAT TGGTGCACAA
421  GTTTCGATTG GTCATACACT GAAATATGTT CAACCTGATT TCAAAACAAT TTTAGAGAGC CCAACTGATA
491  AAAAAGTAGG CTGGAAAGTG ATATTTAACA ATATGGTGAA TCAAAATTGG GGACCATACG ATCGAGATTC
561  TTGGAACCCG GTATATGGCA ATCAACTTTT CATGAAAACT AGAAATGGTT CTATGAAAGC AGCAGATAAC
631  TTCCTTGATC CTAACAAAGC AAGTTCTCTA TTATCTTCAG GTTTTCACC AGACTTCGCT ACAGTTATTA
701  CTATGGATAG AAAAGCATCC AAACAACAAA CAAATATAGA TGTAATATAC GAACGAGTTC GTGATGATTA
771  CCAATTGCAT TGGACTTCAA CAAATTGGAA AGGTACCAAT ACTAAAGATA ATGGACAGA TCGTTCTTCA
841  GAAAGATATA AAATCGATTG GGAAAAGAA GAAATGACAA ATGATGACGA TGATGACGAC GATGAT
```

SEQ ID NO: 14
```
  1  ADSDINIKTG TTDIGSNTTV KTGDLVTYDK ENGMHKKVFY SFIDDKNHNK KLLVIRTKGT IAGQYRVYSE
 71  EGANKSGLAW PSAFKVQLQL PDNEVAQISD YYPRNSIDTK EYRSTLTYGF NGNVTGDDTG KIGGCIGAQV
141  SIGHTLKYVQ PDFKTILESP TDKKVGWKVI FNNMVNQNWG PYDRDSWNPV YGNQLFMKTR NGSMKAADNF
211  LDPNKASSLL SSGFSPDFAT VITMDRKASK QQTNIDVIYE RVRDDYQLHW TSTNWKGTNT KDKWTDRSSE
281  RYKIDWEKEE MTNDDDDDD D
```

SEQ ID NO: 15
```
  1  ATGAAATTTG TCTCTTTTAA TATCAACGGC CTGCGCGCCA GACCTCACCA GCTTGAAGCC ATCGTCGAAA
 71  AGCACCAACC GGATGTGATT GGCCTGCAGG AGACAAAAGT TCATGACGAT ATGTTTCCGC TCGAAGAGGT
141  GGCGAAGCTC GGCTACAACG TGTTTTATCA CGGGCAGAAA GGCCATTATG GCGTGGCGCT GCTGACCAAA
211  GAGACGCCGA TTGCCGTGCG TCGCGGCTTT CCCGGTGACG ACGAAGAGGC GCAGCGGCGG ATTATTATGG
281  CGGAAATCCC CTCACTGCTG GTAATGTCA CCGTGATCAA CGGTTACTTC CCGCAGGGTG AAAGCCGCGA
351  CCATCCGATA AAATTCCCGG CAAAAGCGCA GTTTTATCAG AATCTGCAAA ACTACCTGGA AACCGAACTC
421  AAACGTGATA ATCCGGTACT GATTATGGGC GATATGAATA TCAGCCCTAC AGATCTGGAT ATCGGCATTG
491  GCGAAGAAAA CCGTAAGCGC TGGCTGCGTA CCGGTAAATG CTCTTTCCTG CCGGAAGAGC GCGAATGGAT
561  GGACAGGCTG ATGAGCTGGG GGTTGGTCGA TACCTTCCGC ATGCGAATC CGCAAACAGC AGATCGTTTC
631  TCATGGTTTG ATTACCGCTC AAAAGGTTTT GACGATAACC GTGGTCTGCG CATCGACCTG CTGCTCGCCA
701  GCCAACCGCT GGCAGAATGT TGCGTAGAAA CCGGCATCGA CTATGAAATC CGCAGCATGG AAAAACCGTC
771  CGATCACGCC CCCGTCTGGG CGACCTTCCG CCGC
```

SEQ ID NO: 16

```
  1 MKFVSFNING LRARPHQLEA IVEKHQPDVI GLQETKVHDD MFPLEEVAKL GYNVFYHGQK GHYGVALLTK

71 ETPIAVRRGF PGDDEEAQRR IIMAEIPSLL GNVTVINGYF PQGESRDHPI KFPAKAQFYQ NLQNYLETEL

141 KRDNPVLIMG DMNISPTDLD IGIGEENRKR WLRTGKCSFL PEEREWMDRL MSWGLVDTFR HANPQTADRF

211 SWFDYRSKGF DDNRGLRIDL LLASQPLAEC CVETGIDYEI RSMEKPSDHA PVWATFRR
```

SEQ ID NO: 17
```
  1 ATGATGAATG ACGGTAAGCA ACAATCTACC TTTTTGTTTC ACGATTACGA AACCTTTGGC ACGCACCCCG

71 CGTTAGATCG CCCTGCACAG TTCGCAGCCA TTCGCACCGA TAGCGAATTC AATGTCATCG GCGAACCCGA

141 AGTCTTTTAC TGCAAGCCCG CTGATGACTA TTTACCCCAG CCAGGAGCCG TATTAATTAC CGGTATTACC

211 CCGCAGGAAG CACGGGCGAA AGGAGAAAAC GAAGCCGCGT TTGCCGTGCG TATTCACTCG CTTTTTACCG

281 TACCGAAGAC CTGTATTCTG GGCTACAACA ATGTGCGTTT CGACGACGAA GTCACACGCA ACATTTTTTA

351 TCGTAATTTC TACGATCCTT ACGCCTGGAG CTGGCAGCAT GATAACTCGC GCTGGGATTT ACTGGATGTT

421 ATGCGTGCCT GTTATGCCCT GCGCCCGGAA GGAATAAACT GGCCTGAAAA TGATGACGGT CTACCGAGCT

491 TTCGCCTTGA GCATTTAACC AAAGCGAATG GTATTGAACA TAGCAACGCC CACGATGCGA TGGCTGATGT

561 GTACGCCACT ATTGCGATGG CAAAGCTGGT AAAAACGCGT CAGCCACGCC TGTTTGATTA TCTCTTTACC

631 CATCGTAATA AACACAAACT GATGGCGTTG ATTGATGTTC CGCAGATGAA ACCCCTGGTG CACGTTTCCG

701 GAATGTTTGG AGCATGGCGC GGCAATACCA GCTGGGTGGC ACCGCTGGCG TGGCATCCTG AAAATCGCAA

771 TGCCGTAATT ATGGTGGATT TGGCAGGAGA CATTTCGCCA TTACTGGAAC TGGATAGCGA CACATTGCGC

841 GAGCGTTTAT ATACCGCAAA AACCGATCTT GGCGATAACG CCGCCGTTCC GGTTAAGCTG GTGCATATCA

911 ATAAATGTCC GGTGCTGGCC CAGGCGAATA CGCTACGCCC GGAAGATGCC GACCGACTGG GAATTAATCG

981 TCAGCATTGC CTCGATAACC TGAAAATTCT GCGTGAAAAT CCGCAAGTGC GCGAAAAAGT GGTGGCGATA

1051 TTCGCGGAAG CCGAACCGTT TACGCCTTCA GATAACGTGG ATGCACAGCT TTATAACGGC TTTTTCAGTG

1121 ACGCAGATCG TGCAGCAATG AAAATTGTGC TGGAAACCGA GCCGCGTAAT TTACCGGCAC TGGATATCAC

1191 TTTTGTTGAT AAACGGATTG AAAAGCTGTT GTTCAATTAT CGGGCACGCA ACTTCCCGGG GACGCTGGAT

1261 TATGCCGAGC AGCAACGCTG GCTGGAGCAC CGTCGCCAGG TCTTCACGCC AGAGTTTTTG CAGGGTTATG

1331 CTGATGAATT GCAGATGCTG GTACAACAAT ATGCCGATGA CAAAGAGAAA GTGGCGCTGT AAAAGCACT

1401 TTGGCAGTAC GCGGAAGAGA TTGTC
```

SEQ ID NO: 18
```
  1 MMNDGKQQST FLFHDYETFG THPALDRFAQ FAAIRTDSEF NVIGEPEVFY CKPADDYLPQ PGAVLITGIT

71 PQEARAKGEN EAAFAARIHS LFTVPKTCIL GYNNVRFDDE VTRNIFYRNF YDPYAWSWQH DESRWALLDV

141 MRACYALRPE GINWPENDDG LPSFRLEHLT KANGIEHSNA HDAMADVYAT IAMAKLVKTR QPRLFDYLFT

211 HRNKHKLMAL IDVPQMKPLV HVSGMFGAWR GNTSWVAPLA WHPENRNAVI MVDLAGDISP LLELDSDTLR

281 ERLYTAKTDL GDNAAVPVKL VHINKCPVLA QANTLRPEDA DRLGINRQHC LDNLKILREN PQVREKVVAI

351 FAEAEPFTPS DNVDAQLYNG FFSDADRAAM KIVLETEPRN LPALDITFVD KRIEKLLFNY RARNFPGTLD

421 YAEQQRWLEH RRQVFTPEFL QGYADELQML VQQYADDKEK VALLKALWQY AEEIV
```

SEQ ID NO: 19
```
  1 TCCGGAAGCG GCTCTGGTAG TGGTTCTGGC ATGACACCGG ACATTATCCT GCAGCGTACC GGGATCGATG

71 TGAGAGCTGT CGAACAGGGG GATGATGCGT GGCACAAATT ACGGCTCGGC GTCATCACCG CTTCAGAAGT

141 TCACAACGTG ATAGCAAAAC CCCGCTCCGG AAAGAAGTGG CCTGACATGA AAATGTCCTA CTTCCACACC

211 CTGCTTGCTG AGGTTTGCAC CGGTGTGGCT CCGGAAGTTA ACGCTAAAGC ACTGGCCTGG GGAAAACAGT

281 ACGAGAACGA CGCCAGAACC CTGTTTGAAT TCACTTCCGG CGTGAATGTT ACTGAATCCC CGATCATCTA

351 TCGCGACGAA AGTATGCGTA CCGCCTGCTC TCCCGATGGT TTATGCAGTG ACGGCAACGG CCTTGAACTG

421 AAATGCCCGT TACCTCCCG GGATTTCATG AAGTTCCGGC TCGGTGGTTT CGAGGCCATA AAGTCAGCTT
```

```
491 ACATGGCCCA GGTGCAGTAC AGCATGTGGG TGACGCGAAA AATGCCTGG TACTTTGCCA ACTATGACCC

561 GCGTATGAAG CGTGAAGGCC TGCATTATGT CGTGATTGAG CGGGATGAAA AGTACATGGC GAGTTTTGAC

631 GAGATCGTGC CGGAGTTCAT CGAAAAAATG GACGAGGCAC TGGCTGAAAT TGGTTTTGTA TTTGGGGAGC

701 AATGGCGATC TGGCTCTGGT TCCGGCAGCG GTTCCGGA
```

SEQ ID NO: 20

```
  1 MTPDIILQRT GIDVRAVEQG DDAWHKLRLG VITASEVHNV IAKPRSGKKW PDMKMSYFHT LLAEVCTGVA

71 PEVNAKALAW GKQYENDART LFEFTSGVNV TESPIIYRDE SMRTACSPDG LCSAGNGLEL KCPFTSRDFM

141 KFRLGGFEAI KSAYMAQVQY SMWVTRKNAW YFANYDPRMK REGLHYVVIE RDEKYMASFD EIVPEFIEKM

211 DEALAEIGFV FGEQWR
```

---

The invention claimed is:

1. A α-hemolysin (α-HL) pore comprising:
   (a) seven subunits each comprising the sequence shown in SEQ ID NO: 2; and
   (b) a molecular adaptor that facilitates an interaction between the pore and the nucleotide(s),
   wherein one or more of the seven subunits is modified at position 139 of SEQ ID NO: 2 and/or at a position that is less than 15 angstroms from residue 139 of SEQ ID NO: 2 to facilitate positioning of the adaptor, and
   wherein the molecular adaptor is covalently attached to one or more of the subunits such that it is positioned in a horizontal plane that is less than 5 angstroms from the horizontal plane of residue 139 of SEQ ID NO: 2.

2. A α-HL pore according to claim 1, wherein (a) one or more of the seven subunits comprises a glutamine at position 139 of SEQ ID NO: 2 and/or at a position that is less than 15 angstroms from residue 139 of SEQ ID NO: 2 or (b) all seven subunits comprise a glutamine at position 139 of SEQ ID NO: 2 and/or at a position that is less than 15 angstroms from residue 139 of SEQ ID NO: 2.

3. A α-HL pore according to claim 2, wherein one or more of the seven subunits comprise a glutamine at one or more of residues 136, 137, 138, 139, 140, 141 and 142 of SEQ ID NO: 2.

4. A α-HL pore according to claim 1, wherein the adaptor is covalently attached to residue 119, 121 or 135 of SEQ ID NO: 2 in one or more of the subunits.

5. A α-HL pore according to claim 4, wherein residue 119, 121 or 135 is modified in one or more of the subunits to facilitate the covalent attachment of the adaptor.

6. A α-HL pore according to claim 5, wherein residue 119, 121 or 135 is modified by substitution with a cysteine residue.

7. A α-HL pore according to claim 1, wherein the molecular adaptor is a cyclodextrin.

8. A α-HL pore according to claim 7, wherein the cyclodextrin is heptakis-6-amino-β-cyclodextrin (am$_7$β-CD).

9. A α-HL pore according to claim 1, wherein the adaptor is covalently attached to the pore via a bifunctional cross-linker.

10. A method of producing a pore according to claim 1, comprising:
    (a) providing the pore; and
    (b) covalently attaching to the pore a molecular adaptor that facilitates an interaction between the pore and one or more nucleotide(s).

11. A method according to claim 10, wherein the providing in (a) comprises expressing in a host cell a polynucleotide sequence which encodes a subunit of α-HL having the sequence shown in SEQ ID NO: 2, wherein the subunit has a cysteine at residue 119, 121 or 135 of SEQ ID NO: 2.

12. A method according to claim 10, wherein the pore provided in step (a) comprises a protective leaving group and step (b) comprises displacing the leaving group from the pore.

13. A method according to claim 10, wherein the adaptor is attached to:
    one or more subunits of the pore before they oligomerise;
    one or more subunits of the pore as they oligomerise; or
    an oligomerised pore.

14. A method of identifying an individual nucleotide, comprising:
    (a) contacting the nucleotide with a pore according to any one of claim 1, 2, or 4-7 so that the nucleotide interacts with the pore; and
    (b) measuring the current passing through the pore during the interaction and thereby determining the identity of the nucleotide.

15. A method of sequencing a target nucleic acid sequence, comprising:
    (a) digesting an individual nucleotide from one end of the target sequence using an exonuclease;
    (b) contacting the nucleotide with a pore according to any one of claim 1, 2, or 4 7 claim 1 so that the nucleotide interacts with the adaptor;
    (c) measuring the current passing through the pore during the interaction and thereby determining the identity of the nucleotide; and
    (d) repeating steps (a) to (c) at the same end of the target sequence and thereby determining the sequence of the target sequence.

16. A kit for sequencing a nucleic acid, comprising:
    a pore according to claim 1; and
    an exonuclease.

17. A α-HL pore according to claim 1, wherein all seven subunits comprise a glutamine at residue 139 of SEQ ID NO: 2 and one subunit comprises a cysteine at position 135 of SEQ ID NO: 2.

18. A α-HL pore according to claim 2, wherein all seven subunits comprise a glutamine at residue 139 of SEQ ID NO: 2, wherein residue 119, 121 or 135 of SEQ ID NO: 2 is modified in one or more of the subunits by substitution with a cysteine residue and the molecular adaptor is a cyclodextrin.

19. A protein comprising:
(a) seven subunits each comprising the sequence shown in SEQ ID NO: 2 or a sequence that is at least 95% homologous to SEQ ID NO: 2 based on amino acid identity over the entire sequence; and
(b) a molecular adaptor that facilitates an interaction between the protein and the nucleotide(s),
wherein one or more of the seven subunits is modified at position 139 of SEQ ID NO: 2 and/or at a position that is less than 15 angstroms from residue 139 of SEQ ID NO: 2 to facilitate positioning of the adaptor, and
wherein the molecular adaptor is covalently attached to one or more of the subunits such that it is positioned in a horizontal plane that is less than 5 angstroms from the horizontal plane of residue 139 of SEQ ID NO: 2.

20. The protein according to claim 19, wherein (a) one or more of the seven subunits comprises a glutamine at position 139 of SEQ ID NO: 2 and/or at a position that is less than 15 angstroms from residue 139 of SEQ ID NO: 2 or (b) all seven subunits comprise a glutamine at position 139 of SEQ ID NO: 2 and/or at a position that is less than 15 angstroms from residue 139 of SEQ ID NO: 2.

21. The protein according to claim 20, wherein one or more of the seven subunits comprise a glutamine at one or more of residues 136, 137, 138, 139, 140, 141 and 142 of SEQ ID NO: 2.

22. The protein according to claim 19, wherein the adaptor is covalently attached to residue 119, 121 or 135 of SEQ ID NO: 2 in one or more of the subunits.

23. The protein according to claim 22, wherein residue 119, 121 or 135 is modified in one or more of the subunits to facilitate the covalent attachment of the adaptor.

24. The protein according to claim 23, wherein residue 119, 121 or 135 is modified by substitution with a cysteine residue.

25. The protein according to claim 19, wherein the molecular adaptor is a cyclodextrin.

26. The protein according to claim 25, wherein the cyclodextrin is heptakis-6-amino-β-cyclodextrin (am$_7$β-CD).

27. The protein according to claim 19, wherein the adaptor is covalently attached to the protein via a bifunctional crosslinker.

28. A kit for sequencing a nucleic acid, comprising:
a protein according to claim 19; and
an exonuclease.

29. A method of producing a protein according to claim 19, comprising:
(a) providing the protein; and
(b) covalently attaching to the protein a molecular adaptor that facilitates an interaction between the protein and one or more nucleotide(s).

30. A method according to claim 29, wherein the providing in (a) comprises expressing in a host cell a polynucleotide sequence which encodes a subunit of α-HL having the sequence shown in SEQ ID NO: 2 or a variant thereof, wherein the subunit has a cysteine at residue 119, 121 or 135 of SEQ ID NO: 2.

31. A method according to claim 29, wherein the protein provided in step (a) comprises a protective leaving group and step (b) comprises displacing the leaving group from the protein.

32. A method according to claim 29, wherein the adaptor is attached to:
one or more subunits of the protein before they oligomerise;
one or more subunits of the protein as they oligomerise; or
an oligomerised protein.

* * * * *

UNITED STATES PATENT AND TRADEMARK OFFICE
CERTIFICATE OF CORRECTION

PATENT NO. : 9,447,152 B2
APPLICATION NO. : 13/002717
DATED : September 20, 2016
INVENTOR(S) : James Anthony Clarke et al.

Page 1 of 1

It is certified that error appears in the above-identified patent and that said Letters Patent is hereby corrected as shown below:

In the Claims

At Column 92, Claim 14, Line 47:
"claim 1, 2, or 4-7" should read --claims 1, 2, or 3-6--

At Column 92, Claim 15, Line 57:
"any one of claim 1, 2, or 4-7 claim 1" should read --claim 1--

Signed and Sealed this
Fourteenth Day of February, 2017

Michelle K. Lee
*Director of the United States Patent and Trademark Office*

SEQUENCE LISTING

<160> NUMBER OF SEQ ID NOS: 20

<210> SEQ ID NO 1
<211> LENGTH: 882
<212> TYPE: DNA
<213> ORGANISM: Staphylococcus aureus
<220> FEATURE:
<221> NAME/KEY: CDS
<222> LOCATION: (4)..(882)

<400> SEQUENCE: 1

```
atg gca gat tct gat att aat att aaa acc ggt act aca gat att gga          48
    Ala Asp Ser Asp Ile Asn Ile Lys Thr Gly Thr Thr Asp Ile Gly
    1               5                  10                  15 agc aat act aca gta aaa aca ggt gat tta gtc act tat gat aaa gaa          96
Ser Asn Thr Thr Val Lys Thr Gly Asp Leu Val Thr Tyr Asp Lys Glu
                 20                  25                  30 aat ggc atg cac aaa aaa gta ttt tat agt ttt atc gat gat aaa aat         144
Asn Gly Met His Lys Lys Val Phe Tyr Ser Phe Ile Asp Asp Lys Asn
             35                  40                  45 cac aat aaa aaa ctg cta gtt att aga aca aaa ggt acc att gct ggt         192
His Asn Lys Lys Leu Leu Val Ile Arg Thr Lys Gly Thr Ile Ala Gly
         50                  55                  60 caa tat aga gtt tat agc gaa gaa ggt gct aac aaa agt ggt tta gcc         240
Gln Tyr Arg Val Tyr Ser Glu Glu Gly Ala Asn Lys Ser Gly Leu Ala
 65                  70                  75 tgg cct tca gcc ttt aag gta cag ttg caa cta cct gat aat gaa gta         288
Trp Pro Ser Ala Phe Lys Val Gln Leu Gln Leu Pro Asp Asn Glu Val
 80                  85                  90                  95 gct caa ata tct gat tac tat cca aga aat tcg att gat aca aaa gag         336
Ala Gln Ile Ser Asp Tyr Tyr Pro Arg Asn Ser Ile Asp Thr Lys Glu
                100                 105                 110 tat atg agt act tta act tat gga ttc aac ggt aat gtt act ggt gat         384
Tyr Met Ser Thr Leu Thr Tyr Gly Phe Asn Gly Asn Val Thr Gly Asp
            115                 120                 125 gat aca gga aaa att ggc ggc ctt att ggt gca aat gtt tcg att ggt         432
Asp Thr Gly Lys Ile Gly Gly Leu Ile Gly Ala Asn Val Ser Ile Gly
        130                 135                 140 cat aca ctg aaa tat gtt caa cct gat ttc aaa aca att tta gag agc         480
His Thr Leu Lys Tyr Val Gln Pro Asp Phe Lys Thr Ile Leu Glu Ser
    145                 150                 155 cca act gat aaa aaa gta ggc tgg aaa gtg ata ttt aac aat atg gtg         528
Pro Thr Asp Lys Lys Val Gly Trp Lys Val Ile Phe Asn Asn Met Val
160                 165                 170                 175 aat caa aat tgg gga cca tac gat cga gat tct tgg aac ccg gta tat         576
Asn Gln Asn Trp Gly Pro Tyr Asp Arg Asp Ser Trp Asn Pro Val Tyr
```

```
                        180                 185                 190
ggc aat caa ctt ttc atg aaa act aga aat ggt tct atg aaa gca gca      624
Gly Asn Gln Leu Phe Met Lys Thr Arg Asn Gly Ser Met Lys Ala Ala
        195                 200                 205 gat aac ttc ctt gat cct aac aaa gca agt tct cta tta tct tca ggg      672
Asp Asn Phe Leu Asp Pro Asn Lys Ala Ser Ser Leu Leu Ser Ser Gly
    210                 215                 220 ttt tca cca gac ttc gct aca gtt att act atg gat aga aaa gca tcc      720
Phe Ser Pro Asp Phe Ala Thr Val Ile Thr Met Asp Arg Lys Ala Ser
225                 230                 235 aaa caa caa aca aat ata gat gta ata tac gaa cga gtt cgt gat gat      768
Lys Gln Gln Thr Asn Ile Asp Val Ile Tyr Glu Arg Val Arg Asp Asp
240                 245                 250                 255 tac caa ttg cat tgg act tca aca aat tgg aaa ggt acc aat act aaa      816
Tyr Gln Leu His Trp Thr Ser Thr Asn Trp Lys Gly Thr Asn Thr Lys
                260                 265                 270 gat aaa tgg aca gat cgt tct tca gaa aga tat aaa atc gat tgg gaa      864
Asp Lys Trp Thr Asp Arg Ser Ser Glu Arg Tyr Lys Ile Asp Trp Glu
            275                 280                 285 aaa gaa gaa atg aca aat                                              882
Lys Glu Glu Met Thr Asn
            290

<210> SEQ ID NO 2
<211> LENGTH: 293
<212> TYPE: PRT
<213> ORGANISM: Staphylococcus aureus

<400> SEQUENCE: 2

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220
```

```
Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
        260                 265                 270

Lys Trp Thr Asp Arg Ser Ser Glu Arg Tyr Lys Ile Asp Trp Glu Lys
    275                 280                 285

Glu Glu Met Thr Asn
    290

<210> SEQ ID NO 3
<211> LENGTH: 882
<212> TYPE: DNA
<213> ORGANISM: Artificial sequence
<220> FEATURE:
<223> OTHER INFORMATION: alpha-HL M113R-RL2
<220> FEATURE:
<221> NAME/KEY: CDS
<222> LOCATION: (4)..(882)

<400> SEQUENCE: 3 atg gca gat tct gat att aat att gcg acc ggt act aca gat att gga      48
    Ala Asp Ser Asp Ile Asn Ile Ala Thr Gly Thr Thr Asp Ile Gly
    1               5                   10                  15 agc aat act aca gta aaa aca ggt gat tta gtc act tat gat aaa gaa      96
Ser Asn Thr Thr Val Lys Thr Gly Asp Leu Val Thr Tyr Asp Lys Glu
                20                  25                  30 aat ggc atg cac aaa aaa gta ttt tat agt ttt atc gat gat aaa aat     144
Asn Gly Met His Lys Lys Val Phe Tyr Ser Phe Ile Asp Asp Lys Asn
            35                  40                  45 cac aat aaa aaa ctg cta gtt att aga aca aaa ggt acc att gct ggt     192
His Asn Lys Lys Leu Leu Val Ile Arg Thr Lys Gly Thr Ile Ala Gly
        50                  55                  60 caa tat aga gtt tat agc gaa gaa ggt gct aac aaa agt ggt tta gcc     240
Gln Tyr Arg Val Tyr Ser Glu Glu Gly Ala Asn Lys Ser Gly Leu Ala
65                  70                  75 tgg cct tca gcc ttt aag gta cag ttg caa cta cct gat aat gaa gta     288
Trp Pro Ser Ala Phe Lys Val Gln Leu Gln Leu Pro Asp Asn Glu Val
80                  85                  90                  95 gct caa ata tct gat tac tat ccg cgg aat tcg att gat aca aaa gag     336
Ala Gln Ile Ser Asp Tyr Tyr Pro Arg Asn Ser Ile Asp Thr Lys Glu
                100                 105                 110 tat agg agt acg tta acg tac gga ttc aac ggt aac ctt act ggt gat     384
Tyr Arg Ser Thr Leu Thr Tyr Gly Phe Asn Gly Asn Leu Thr Gly Asp
            115                 120                 125 gat act agt aaa att gga ggc ctt att ggg gcc cag gtt tcc cta ggt     432
Asp Thr Ser Lys Ile Gly Gly Leu Ile Gly Ala Gln Val Ser Leu Gly
        130                 135                 140 cat aca ctt aat tat gtt caa cct gat ttc aaa aca att ctc gag agc     480
His Thr Leu Asn Tyr Val Gln Pro Asp Phe Lys Thr Ile Leu Glu Ser
    145                 150                 155 cca act gat aaa aaa gta ggc tgg aaa gtg ata ttt aac aat atg gtg     528
Pro Thr Asp Lys Lys Val Gly Trp Lys Val Ile Phe Asn Asn Met Val
160                 165                 170                 175 aat caa aat tgg gga cca tac gat cga gat tct tgg aac ccg gta tat     576
Asn Gln Asn Trp Gly Pro Tyr Asp Arg Asp Ser Trp Asn Pro Val Tyr
                180                 185                 190 ggc aat caa ctt ttc atg aag act aga aat ggt tct atg aaa gca gca     624
Gly Asn Gln Leu Phe Met Lys Thr Arg Asn Gly Ser Met Lys Ala Ala
```

```
                    195                 200                 205
gat aac ttc ctt gat cct aac aaa gca agt tcc cta tta tct tca ggg    672
Asp Asn Phe Leu Asp Pro Asn Lys Ala Ser Ser Leu Leu Ser Ser Gly
            210                 215                 220 ttt tca cca gac ttc gct aca gtt att act atg gat aga aaa gca tcc    720
Phe Ser Pro Asp Phe Ala Thr Val Ile Thr Met Asp Arg Lys Ala Ser
225                 230                 235 aaa caa caa aca aat ata gat gta ata tac gaa cga gtt cgt gat gat    768
Lys Gln Gln Thr Asn Ile Asp Val Ile Tyr Glu Arg Val Arg Asp Asp
240                 245                 250                 255 tac caa ttg cat tgg act tca aca aat tgg aaa ggt acc aat act aaa    816
Tyr Gln Leu His Trp Thr Ser Thr Asn Trp Lys Gly Thr Asn Thr Lys
                260                 265                 270 gat aaa tgg aca gat cgt tct tca gaa aga tat aaa atc gat tgg gaa    864
Asp Lys Trp Thr Asp Arg Ser Ser Glu Arg Tyr Lys Ile Asp Trp Glu
            275                 280                 285 aaa gaa gaa atg aca aat                                            882
Lys Glu Glu Met Thr Asn
            290
```

<210> SEQ ID NO 4
<211> LENGTH: 293
<212> TYPE: PRT
<213> ORGANISM: Artificial sequence
<220> FEATURE:
<223> OTHER INFORMATION: alpha-HL M113R-RL2

<400> SEQUENCE: 4

```
Ala Asp Ser Asp Ile Asn Ile Ala Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Glu Tyr
        100                 105                 110

Arg Ser Thr Leu Thr Tyr Gly Phe Asn Gly Asn Leu Thr Gly Asp Asp
    115                 120                 125

Thr Ser Lys Ile Gly Gly Leu Ile Gly Ala Gln Val Ser Leu Gly His
130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
        180                 185                 190

Asn Gln Leu Phe Met Lys Thr Arg Asn Gly Ser Met Lys Ala Ala Asp
    195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
```

```
                225                 230                 235                 240
Gln Gln Thr Asn Ile Asp Val Ile Tyr Glu Arg Val Arg Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
            275                 280                 285

Glu Glu Met Thr Asn
        290

<210> SEQ ID NO 5
<211> LENGTH: 882
<212> TYPE: DNA
<213> ORGANISM: Artificial sequence
<220> FEATURE:
<223> OTHER INFORMATION: alpha-HL M113R
<220> FEATURE:
<221> NAME/KEY: CDS
<222> LOCATION: (4)..(882)

<400> SEQUENCE: 5 atg gca gat tct gat att aat att aaa acc ggt act aca gat att gga        48
    Ala Asp Ser Asp Ile Asn Ile Lys Thr Gly Thr Thr Asp Ile Gly
    1               5                   10                  15 agc aat act aca gta aaa aca ggt gat tta gtc act tat gat aaa gaa        96
Ser Asn Thr Thr Val Lys Thr Gly Asp Leu Val Thr Tyr Asp Lys Glu
                20                  25                  30 aat ggc atg cac aaa aaa gta ttt tat agt ttt atc gat gat aaa aat       144
Asn Gly Met His Lys Lys Val Phe Tyr Ser Phe Ile Asp Asp Lys Asn
            35                  40                  45 cac aat aaa aaa ctg cta gtt att aga aca aaa ggt acc att gct ggt       192
His Asn Lys Lys Leu Leu Val Ile Arg Thr Lys Gly Thr Ile Ala Gly
        50                  55                  60 caa tat aga gtt tat agc gaa gaa ggt gct aac aaa agt ggt tta gcc       240
Gln Tyr Arg Val Tyr Ser Glu Glu Gly Ala Asn Lys Ser Gly Leu Ala
    65                  70                  75 tgg cct tca gcc ttt aag gta cag ttg caa cta cct gat aat gaa gta       288
Trp Pro Ser Ala Phe Lys Val Gln Leu Gln Leu Pro Asp Asn Glu Val
80                  85                  90                  95 gct caa ata tct gat tac tat cca aga aat tcg att gat aca aaa gag       336
Ala Gln Ile Ser Asp Tyr Tyr Pro Arg Asn Ser Ile Asp Thr Lys Glu
                100                 105                 110 tat agg agt act tta act tat gga ttc aac ggt aat gtt act ggt gat       384
Tyr Arg Ser Thr Leu Thr Tyr Gly Phe Asn Gly Asn Val Thr Gly Asp
            115                 120                 125 gat aca gga aaa att ggc ggc ctt att ggt gca aat gtt tcg att ggt       432
Asp Thr Gly Lys Ile Gly Gly Leu Ile Gly Ala Asn Val Ser Ile Gly
        130                 135                 140 cat aca ctg aaa tat gtt caa cct gat ttc aaa aca att tta gag agc       480
His Thr Leu Lys Tyr Val Gln Pro Asp Phe Lys Thr Ile Leu Glu Ser
    145                 150                 155 cca act gat aaa aaa gta ggc tgg aaa gtg ata ttt aac aat atg gtg       528
Pro Thr Asp Lys Lys Val Gly Trp Lys Val Ile Phe Asn Asn Met Val
160                 165                 170                 175 aat caa aat tgg gga cca tac gat cga gat tct tgg aac ccg gta tat       576
Asn Gln Asn Trp Gly Pro Tyr Asp Arg Asp Ser Trp Asn Pro Val Tyr
                180                 185                 190 ggc aat caa ctt ttc atg aaa act aga aat ggt tct atg aaa gca gca       624
Gly Asn Gln Leu Phe Met Lys Thr Arg Asn Gly Ser Met Lys Ala Ala
            195                 200                 205
```

-continued

```
gat aac ttc ctt gat cct aac aaa gca agt tct cta tta tct tca ggg     672
Asp Asn Phe Leu Asp Pro Asn Lys Ala Ser Ser Leu Leu Ser Ser Gly
        210                 215                 220 ttt tca cca gac ttc gct aca gtt att act atg gat aga aaa gca tcc     720
Phe Ser Pro Asp Phe Ala Thr Val Ile Thr Met Asp Arg Lys Ala Ser
225                 230                 235 aaa caa caa aca aat ata gat gta ata tac gaa cga gtt cgt gat gat     768
Lys Gln Gln Thr Asn Ile Asp Val Ile Tyr Glu Arg Val Arg Asp Asp
240                 245                 250                 255 tac caa ttg cat tgg act tca aca aat tgg aaa ggt acc aat act aaa     816
Tyr Gln Leu His Trp Thr Ser Thr Asn Trp Lys Gly Thr Asn Thr Lys
                260                 265                 270 gat aaa tgg aca gat cgt tct tca gaa aga tat aaa atc gat tgg gaa     864
Asp Lys Trp Thr Asp Arg Ser Ser Glu Arg Tyr Lys Ile Asp Trp Glu
            275                 280                 285 aaa gaa gaa atg aca aat                                             882
Lys Glu Glu Met Thr Asn
            290
```

<210> SEQ ID NO 6
<211> LENGTH: 293
<212> TYPE: PRT
<213> ORGANISM: Artificial sequence
<220> FEATURE:
<223> OTHER INFORMATION: alpha-HL M113R

<400> SEQUENCE: 6

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Arg Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240
```

-continued

```
Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
        260                 265                 270

Lys Trp Thr Asp Arg Ser Ser Glu Arg Tyr Lys Ile Asp Trp Glu Lys
    275                 280                 285

Glu Glu Met Thr Asn
    290

<210> SEQ ID NO 7
<211> LENGTH: 882
<212> TYPE: DNA
<213> ORGANISM: Artificial sequence
<220> FEATURE:
<223> OTHER INFORMATION: alpha-HL M113R/N139Q
<220> FEATURE:
<221> NAME/KEY: CDS
<222> LOCATION: (4)..(882)

<400> SEQUENCE: 7 atg gca gat tct gat att aat att aaa acc ggt act aca gat att gga      48
    Ala Asp Ser Asp Ile Asn Ile Lys Thr Gly Thr Thr Asp Ile Gly
    1               5                  10                  15 agc aat act aca gta aaa aca ggt gat tta gtc act tat gat aaa gaa      96
Ser Asn Thr Thr Val Lys Thr Gly Asp Leu Val Thr Tyr Asp Lys Glu
                20                  25                  30 aat ggc atg cac aaa aaa gta ttt tat agt ttt atc gat gat aaa aat     144
Asn Gly Met His Lys Lys Val Phe Tyr Ser Phe Ile Asp Asp Lys Asn
            35                  40                  45 cac aat aaa aaa ctg cta gtt att aga aca aaa ggt acc att gct ggt     192
His Asn Lys Lys Leu Leu Val Ile Arg Thr Lys Gly Thr Ile Ala Gly
        50                  55                  60 caa tat aga gtt tat agc gaa gaa ggt gct aac aaa agt ggt tta gcc     240
Gln Tyr Arg Val Tyr Ser Glu Glu Gly Ala Asn Lys Ser Gly Leu Ala
    65                  70                  75 tgg cct tca gcc ttt aag gta cag ttg caa cta cct gat aat gaa gta     288
Trp Pro Ser Ala Phe Lys Val Gln Leu Gln Leu Pro Asp Asn Glu Val
80                  85                  90                  95 gct caa ata tct gat tac tat cca aga aat tcg att gat aca aaa gag     336
Ala Gln Ile Ser Asp Tyr Tyr Pro Arg Asn Ser Ile Asp Thr Lys Glu
                100                 105                 110 tat agg agt act tta act tat gga ttc aac ggt aat gtt act ggt gat     384
Tyr Arg Ser Thr Leu Thr Tyr Gly Phe Asn Gly Asn Val Thr Gly Asp
            115                 120                 125 gat aca gga aaa att ggc ggc ctt att ggt gca caa gtt tcg att ggt     432
Asp Thr Gly Lys Ile Gly Gly Leu Ile Gly Ala Gln Val Ser Ile Gly
        130                 135                 140 cat aca ctg aaa tat gtt caa cct gat ttc aaa aca att tta gag agc     480
His Thr Leu Lys Tyr Val Gln Pro Asp Phe Lys Thr Ile Leu Glu Ser
    145                 150                 155 cca act gat aaa aaa gta ggc tgg aaa gtg ata ttt aac aat atg gtg     528
Pro Thr Asp Lys Lys Val Gly Trp Lys Val Ile Phe Asn Asn Met Val
160                 165                 170                 175 aat caa aat tgg gga cca tac gat cga gat tct tgg aac ccg gta tat     576
Asn Gln Asn Trp Gly Pro Tyr Asp Arg Asp Ser Trp Asn Pro Val Tyr
                180                 185                 190 ggc aat caa ctt ttc atg aaa act aga aat ggt tct atg aaa gca gca     624
Gly Asn Gln Leu Phe Met Lys Thr Arg Asn Gly Ser Met Lys Ala Ala
            195                 200                 205 gat aac ttc ctt gat cct aac aaa gca agt tct cta tta tct tca ggg     672
Asp Asn Phe Leu Asp Pro Asn Lys Ala Ser Ser Leu Leu Ser Ser Gly
```

```
                 210                 215                 220
ttt tca cca gac ttc gct aca gtt att act atg gat aga aaa gca tcc      720
Phe Ser Pro Asp Phe Ala Thr Val Ile Thr Met Asp Arg Lys Ala Ser
    225                 230                 235 aaa caa caa aca aat ata gat gta ata tac gaa cga gtt cgt gat gat      768
Lys Gln Gln Thr Asn Ile Asp Val Ile Tyr Glu Arg Val Arg Asp Asp
240                 245                 250                 255 tac caa ttg cat tgg act tca aca aat tgg aaa ggt acc aat act aaa      816
Tyr Gln Leu His Trp Thr Ser Thr Asn Trp Lys Gly Thr Asn Thr Lys
            260                 265                 270 gat aaa tgg aca gat cgt tct tca gaa aga tat aaa atc gat tgg gaa      864
Asp Lys Trp Thr Asp Arg Ser Ser Glu Arg Tyr Lys Ile Asp Trp Glu
        275                 280                 285 aaa gaa gaa atg aca aat                                              882
Lys Glu Glu Met Thr Asn
        290
```

<210> SEQ ID NO 8
<211> LENGTH: 293
<212> TYPE: PRT
<213> ORGANISM: Artificial sequence
<220> FEATURE:
<223> OTHER INFORMATION: alpha-HL M113R/N139Q

<400> SEQUENCE: 8

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Arg Ser Thr Leu Thr Tyr Gly Phe Asn Gly Asn Val Thr Gly Asp Asp
        115                 120                 125

Thr Gly Lys Ile Gly Gly Leu Ile Gly Ala Gln Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255
```

```
Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 9
<211> LENGTH: 906
<212> TYPE: DNA
<213> ORGANISM: Artificial sequence
<220> FEATURE:
<223> OTHER INFORMATION: alpha-HL M113R/N139Q/G119C-D8
<220> FEATURE:
<221> NAME/KEY: CDS
<222> LOCATION: (4)..(906)

<400> SEQUENCE: 9
```

| | | | | | | | | | | | | | | | | |
|---|---|---|---|---|---|---|---|---|---|---|---|---|---|---|---|---|
| atg | gca | gat | tct | gat | att | aat | att | aaa | acc | ggt | act | aca | gat | att | gga | 48 |
| | Ala | Asp | Ser | Asp | Ile | Asn | Ile | Lys | Thr | Gly | Thr | Thr | Asp | Ile | Gly | |
| | 1 | | | 5 | | | | | 10 | | | | | 15 | | |
| agc | aat | act | aca | gta | aaa | aca | ggt | gat | tta | gtc | act | tat | gat | aaa | gaa | 96 |
| Ser | Asn | Thr | Thr | Val | Lys | Thr | Gly | Asp | Leu | Val | Thr | Tyr | Asp | Lys | Glu | |
| | | | 20 | | | | | 25 | | | | | 30 | | | |
| aat | ggc | atg | cac | aaa | aaa | gta | ttt | tat | agt | ttt | atc | gat | gat | aaa | aat | 144 |
| Asn | Gly | Met | His | Lys | Lys | Val | Phe | Tyr | Ser | Phe | Ile | Asp | Asp | Lys | Asn | |
| | | | 35 | | | | | 40 | | | | | 45 | | | |
| cac | aat | aaa | aaa | ctg | cta | gtt | att | aga | aca | aaa | ggt | acc | att | gct | ggt | 192 |
| His | Asn | Lys | Lys | Leu | Leu | Val | Ile | Arg | Thr | Lys | Gly | Thr | Ile | Ala | Gly | |
| | 50 | | | | | 55 | | | | | 60 | | | | | |
| caa | tat | aga | gtt | tat | agc | gaa | gaa | ggt | gct | aac | aaa | agt | ggt | tta | gcc | 240 |
| Gln | Tyr | Arg | Val | Tyr | Ser | Glu | Glu | Gly | Ala | Asn | Lys | Ser | Gly | Leu | Ala | |
| | 65 | | | | | 70 | | | | | 75 | | | | | |
| tgg | cct | tca | gcc | ttt | aag | gta | cag | ttg | caa | cta | cct | gat | aat | gaa | gta | 288 |
| Trp | Pro | Ser | Ala | Phe | Lys | Val | Gln | Leu | Gln | Leu | Pro | Asp | Asn | Glu | Val | |
| 80 | | | | | 85 | | | | | 90 | | | | | 95 | |
| gct | caa | ata | tct | gat | tac | tat | cca | aga | aat | tcg | att | gat | aca | aaa | gag | 336 |
| Ala | Gln | Ile | Ser | Asp | Tyr | Tyr | Pro | Arg | Asn | Ser | Ile | Asp | Thr | Lys | Glu | |
| | | | 100 | | | | | 105 | | | | | 110 | | | |
| tat | agg | agt | act | tta | act | tat | tgt | ttc | aac | ggt | aat | gtt | act | ggt | gat | 384 |
| Tyr | Arg | Ser | Thr | Leu | Thr | Tyr | Cys | Phe | Asn | Gly | Asn | Val | Thr | Gly | Asp | |
| | | | 115 | | | | | 120 | | | | | 125 | | | |
| gat | aca | gga | aaa | att | ggc | ggc | ctt | att | ggt | gca | caa | gtt | tcg | att | ggt | 432 |
| Asp | Thr | Gly | Lys | Ile | Gly | Gly | Leu | Ile | Gly | Ala | Gln | Val | Ser | Ile | Gly | |
| | | 130 | | | | | 135 | | | | | 140 | | | | |
| cat | aca | ctg | aaa | tat | gtt | caa | cct | gat | ttc | aaa | aca | att | tta | gag | agc | 480 |
| His | Thr | Leu | Lys | Tyr | Val | Gln | Pro | Asp | Phe | Lys | Thr | Ile | Leu | Glu | Ser | |
| | | 145 | | | | | 150 | | | | | 155 | | | | |
| cca | act | gat | aaa | aaa | gta | ggc | tgg | aaa | gtg | ata | ttt | aac | aat | atg | gtg | 528 |
| Pro | Thr | Asp | Lys | Lys | Val | Gly | Trp | Lys | Val | Ile | Phe | Asn | Asn | Met | Val | |
| 160 | | | | | 165 | | | | | 170 | | | | | 175 | |
| aat | caa | aat | tgg | gga | cca | tac | gat | cga | gat | tct | tgg | aac | ccg | gta | tat | 576 |
| Asn | Gln | Asn | Trp | Gly | Pro | Tyr | Asp | Arg | Asp | Ser | Trp | Asn | Pro | Val | Tyr | |
| | | | 180 | | | | | 185 | | | | | 190 | | | |
| ggc | aat | caa | ctt | ttc | atg | aaa | act | aga | aat | ggt | tct | atg | aaa | gca | gca | 624 |
| Gly | Asn | Gln | Leu | Phe | Met | Lys | Thr | Arg | Asn | Gly | Ser | Met | Lys | Ala | Ala | |
| | | | 195 | | | | | 200 | | | | | 205 | | | |
| gat | aac | ttc | ctt | gat | cct | aac | aaa | gca | agt | tct | cta | tta | tct | tca | ggg | 672 |
| Asp | Asn | Phe | Leu | Asp | Pro | Asn | Lys | Ala | Ser | Ser | Leu | Leu | Ser | Ser | Gly | |
| | | | | 210 | | | | | 215 | | | | | 220 | | |

```
ttt tca cca gac ttc gct aca gtt att act atg gat aga aaa gca tcc    720
Phe Ser Pro Asp Phe Ala Thr Val Ile Thr Met Asp Arg Lys Ala Ser
    225                 230                 235 aaa caa caa aca aat ata gat gta ata tac gaa cga gtt cgt gat gat    768
Lys Gln Gln Thr Asn Ile Asp Val Ile Tyr Glu Arg Val Arg Asp Asp
240                 245                 250                 255 tac caa ttg cat tgg act tca aca aat tgg aaa ggt acc aat act aaa    816
Tyr Gln Leu His Trp Thr Ser Thr Asn Trp Lys Gly Thr Asn Thr Lys
                260                 265                 270 gat aaa tgg aca gat cgt tct tca gaa aga tat aaa atc gat tgg gaa    864
Asp Lys Trp Thr Asp Arg Ser Ser Glu Arg Tyr Lys Ile Asp Trp Glu
            275                 280                 285 aaa gaa gaa atg aca aat gat gac gat gat gac gac gat gat            906
Lys Glu Glu Met Thr Asn Asp Asp Asp Asp Asp Asp Asp
        290                 295                 300
```

<210> SEQ ID NO 10
<211> LENGTH: 301
<212> TYPE: PRT
<213> ORGANISM: Artificial sequence
<220> FEATURE:
<223> OTHER INFORMATION: alpha-HL M113R/N139Q/G119C-D8

<400> SEQUENCE: 10

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Arg Ser Thr Leu Thr Tyr Cys Phe Asn Gly Asn Val Thr Gly Asp Asp
        115                 120                 125

Thr Gly Lys Ile Gly Gly Leu Ile Gly Ala Gln Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
```

```
              260                 265                 270
Lys Trp Thr Asp Arg Ser Ser Glu Arg Tyr Lys Ile Asp Trp Glu Lys
                275                 280                 285

Glu Glu Met Thr Asn Asp Asp Asp Asp Asp Asp Asp
        290                 295                 300

<210> SEQ ID NO 11
<211> LENGTH: 906
<212> TYPE: DNA
<213> ORGANISM: Artificial sequence
<220> FEATURE:
<223> OTHER INFORMATION: alpha-HL M113R/N139Q/N121C-D8
<220> FEATURE:
<221> NAME/KEY: CDS
<222> LOCATION: (4)..(906)

<400> SEQUENCE: 11 atg gca gat tct gat att aat att aaa acc ggt act aca gat att gga        48
    Ala Asp Ser Asp Ile Asn Ile Lys Thr Gly Thr Thr Asp Ile Gly
    1               5                   10                  15 agc aat act aca gta aaa aca ggt gat tta gtc act tat gat aaa gaa        96
Ser Asn Thr Thr Val Lys Thr Gly Asp Leu Val Thr Tyr Asp Lys Glu
                20                  25                  30 aat ggc atg cac aaa aaa gta ttt tat agt ttt atc gat gat aaa aat       144
Asn Gly Met His Lys Lys Val Phe Tyr Ser Phe Ile Asp Asp Lys Asn
            35                  40                  45 cac aat aaa aaa ctg cta gtt att aga aca aaa ggt acc att gct ggt       192
His Asn Lys Lys Leu Leu Val Ile Arg Thr Lys Gly Thr Ile Ala Gly
        50                  55                  60 caa tat aga gtt tat agc gaa gaa ggt gct aac aaa agt ggt tta gcc       240
Gln Tyr Arg Val Tyr Ser Glu Glu Gly Ala Asn Lys Ser Gly Leu Ala
65                  70                  75                  80 tgg cct tca gcc ttt aag gta cag ttg caa cta cct gat aat gaa gta       288
Trp Pro Ser Ala Phe Lys Val Gln Leu Gln Leu Pro Asp Asn Glu Val
                85                  90                  95 gct caa ata tct gat tac tat cca aga aat tcg att gat aca aaa gag       336
Ala Gln Ile Ser Asp Tyr Tyr Pro Arg Asn Ser Ile Asp Thr Lys Glu
            100                 105                 110 tat agg agt act tta act tat gga ttc tgt ggt aat gtt act ggt gat       384
Tyr Arg Ser Thr Leu Thr Tyr Gly Phe Cys Gly Asn Val Thr Gly Asp
        115                 120                 125 gat aca gga aaa att ggc ggc ctt att ggt gca caa gtt tcg att ggt       432
Asp Thr Gly Lys Ile Gly Gly Leu Ile Gly Ala Gln Val Ser Ile Gly
    130                 135                 140 cat aca ctg aaa tat gtt caa cct gat ttc aaa aca att tta gag agc       480
His Thr Leu Lys Tyr Val Gln Pro Asp Phe Lys Thr Ile Leu Glu Ser
145                 150                 155 cca act gat aaa aaa gta ggc tgg aaa gtg ata ttt aac aat atg gtg       528
Pro Thr Asp Lys Lys Val Gly Trp Lys Val Ile Phe Asn Asn Met Val
160                 165                 170                 175 aat caa aat tgg gga cca tac gat cga gat tct tgg aac ccg gta tat       576
Asn Gln Asn Trp Gly Pro Tyr Asp Arg Asp Ser Trp Asn Pro Val Tyr
                180                 185                 190 ggc aat caa ctt ttc atg aaa act aga aat ggt tct atg aaa gca gca       624
Gly Asn Gln Leu Phe Met Lys Thr Arg Asn Gly Ser Met Lys Ala Ala
            195                 200                 205 gat aac ttc ctt gat cct aac aaa gca agt tct cta tta tct tca ggg       672
Asp Asn Phe Leu Asp Pro Asn Lys Ala Ser Ser Leu Leu Ser Ser Gly
        210                 215                 220 ttt tca cca gac ttc gct aca gtt att act atg gat aga aaa gca tcc       720
Phe Ser Pro Asp Phe Ala Thr Val Ile Thr Met Asp Arg Lys Ala Ser
225                 230                 235                 240
```

```
                  225                 230                 235
aaa caa caa aca aat ata gat gta ata tac gaa cga gtt cgt gat gat    768
Lys Gln Gln Thr Asn Ile Asp Val Ile Tyr Glu Arg Val Arg Asp Asp
240                 245                 250                 255 tac caa ttg cat tgg act tca aca aat tgg aaa ggt acc aat act aaa    816
Tyr Gln Leu His Trp Thr Ser Thr Asn Trp Lys Gly Thr Asn Thr Lys
                260                 265                 270 gat aaa tgg aca gat cgt tct tca gaa aga tat aaa atc gat tgg gaa    864
Asp Lys Trp Thr Asp Arg Ser Ser Glu Arg Tyr Lys Ile Asp Trp Glu
            275                 280                 285 aaa gaa gaa atg aca aat gat gac gat gat gac gac gat gat            906
Lys Glu Glu Met Thr Asn Asp Asp Asp Asp Asp Asp Asp Asp
        290                 295                 300

<210> SEQ ID NO 12
<211> LENGTH: 301
<212> TYPE: PRT
<213> ORGANISM: Artificial sequence
<220> FEATURE:
<223> OTHER INFORMATION: alpha-HL M113R/N139Q/N121C-D8

<400> SEQUENCE: 12

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Arg Ser Thr Leu Thr Tyr Gly Phe Cys Gly Asn Val Thr Gly Asp Asp
        115                 120                 125

Thr Gly Lys Ile Gly Gly Leu Ile Gly Ala Gln Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270
```

```
                Lys Trp Thr Asp Arg Ser Ser Glu Arg Tyr Lys Ile Asp Trp Glu Lys
                                275                 280                 285

Glu Glu Met Thr Asn Asp Asp Asp Asp Asp Asp Asp
                290                 295                 300

<210> SEQ ID NO 13
<211> LENGTH: 906
<212> TYPE: DNA
<213> ORGANISM: Artificial sequences
<220> FEATURE:
<223> OTHER INFORMATION: alpha-HL M113R/N139Q/L135C-D8
<220> FEATURE:
<221> NAME/KEY: CDS
<222> LOCATION: (4)..(906)

<400> SEQUENCE: 13 atg gca gat tct gat att aat att aaa acc ggt act aca gat att gga           48
    Ala Asp Ser Asp Ile Asn Ile Lys Thr Gly Thr Thr Asp Ile Gly
    1               5                   10                  15 agc aat act aca gta aaa aca ggt gat tta gtc act tat gat aaa gaa           96
Ser Asn Thr Thr Val Lys Thr Gly Asp Leu Val Thr Tyr Asp Lys Glu
                20                  25                  30 aat ggc atg cac aaa aaa gta ttt tat agt ttt atc gat gat aaa aat         144
Asn Gly Met His Lys Lys Val Phe Tyr Ser Phe Ile Asp Asp Lys Asn
            35                  40                  45 cac aat aaa aaa ctg cta gtt att aga aca aaa ggt acc att gct ggt         192
His Asn Lys Lys Leu Leu Val Ile Arg Thr Lys Gly Thr Ile Ala Gly
        50                  55                  60 caa tat aga gtt tat agc gaa gaa ggt gct aac aaa agt ggt tta gcc         240
Gln Tyr Arg Val Tyr Ser Glu Glu Gly Ala Asn Lys Ser Gly Leu Ala
65                  70                  75 tgg cct tca gcc ttt aag gta cag ttg caa cta cct gat aat gaa gta         288
Trp Pro Ser Ala Phe Lys Val Gln Leu Gln Leu Pro Asp Asn Glu Val
80                  85                  90                  95 gct caa ata tct gat tac tat cca aga aat tcg att gat aca aaa gag         336
Ala Gln Ile Ser Asp Tyr Tyr Pro Arg Asn Ser Ile Asp Thr Lys Glu
                100                 105                 110 tat agg agt act tta act tat gga ttc aac ggt aat gtt act ggt gat         384
Tyr Arg Ser Thr Leu Thr Tyr Gly Phe Asn Gly Asn Val Thr Gly Asp
            115                 120                 125 gat aca gga aaa att ggc ggt tgt att ggt gca caa gtt tcg att ggt         432
Asp Thr Gly Lys Ile Gly Gly Cys Ile Gly Ala Gln Val Ser Ile Gly
        130                 135                 140 cat aca ctg aaa tat gtt caa cct gat ttc aaa aca att tta gag agc         480
His Thr Leu Lys Tyr Val Gln Pro Asp Phe Lys Thr Ile Leu Glu Ser
    145                 150                 155 cca act gat aaa aaa gta ggc tgg aaa gtg ata ttt aac aat atg gtg         528
Pro Thr Asp Lys Lys Val Gly Trp Lys Val Ile Phe Asn Asn Met Val
160                 165                 170                 175 aat caa aat tgg gga cca tac gat cga gat tct tgg aac ccg gta tat         576
Asn Gln Asn Trp Gly Pro Tyr Asp Arg Asp Ser Trp Asn Pro Val Tyr
                180                 185                 190 ggc aat caa ctt ttc atg aaa act aga aat ggt tct atg aaa gca gca         624
Gly Asn Gln Leu Phe Met Lys Thr Arg Asn Gly Ser Met Lys Ala Ala
            195                 200                 205 gat aac ttc ctt gat cct aac aaa gca agt tct cta tta tct tca ggg         672
Asp Asn Phe Leu Asp Pro Asn Lys Ala Ser Ser Leu Leu Ser Ser Gly
        210                 215                 220 ttt tca cca gac ttc gct aca gtt att act atg gat aga aaa gca tcc         720
Phe Ser Pro Asp Phe Ala Thr Val Ile Thr Met Asp Arg Lys Ala Ser
225                 230                 235
```

```
aaa caa caa aca aat ata gat gta ata tac gaa cga gtt cgt gat gat    768
Lys Gln Gln Thr Asn Ile Asp Val Ile Tyr Glu Arg Val Arg Asp Asp
240                 245                 250                 255 tac caa ttg cat tgg act tca aca aat tgg aaa ggt acc aat act aaa    816
Tyr Gln Leu His Trp Thr Ser Thr Asn Trp Lys Gly Thr Asn Thr Lys
                260                 265                 270 gat aaa tgg aca gat cgt tct tca gaa aga tat aaa atc gat tgg gaa    864
Asp Lys Trp Thr Asp Arg Ser Ser Glu Arg Tyr Lys Ile Asp Trp Glu
            275                 280                 285 aaa gaa gaa atg aca aat gat gac gat gat gac gac gat gat            906
Lys Glu Glu Met Thr Asn Asp Asp Asp Asp Asp Asp Asp Asp
        290                 295                 300
```

<210> SEQ ID NO 14
<211> LENGTH: 301
<212> TYPE: PRT
<213> ORGANISM: Artificial sequences
<220> FEATURE:
<223> OTHER INFORMATION: alpha-HL M113R/N139Q/L135C-D8

<400> SEQUENCE: 14

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Arg Ser Thr Leu Thr Tyr Gly Phe Asn Gly Asn Val Thr Gly Asp Asp
        115                 120                 125

Thr Gly Lys Ile Gly Gly Cys Ile Gly Ala Gln Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285
```

```
Glu Glu Met Thr Asn Asp Asp Asp Asp Asp Asp Asp
    290             295             300

<210> SEQ ID NO 15
<211> LENGTH: 804
<212> TYPE: DNA
<213> ORGANISM: E. coli
<220> FEATURE:
<221> NAME/KEY: CDS
<222> LOCATION: (1)..(804)

<400> SEQUENCE: 15 atg aaa ttt gtc tct ttt aat atc aac ggc ctg cgc gcc aga cct cac      48
Met Lys Phe Val Ser Phe Asn Ile Asn Gly Leu Arg Ala Arg Pro His
1               5                   10                  15 cag ctt gaa gcc atc gtc gaa aag cac caa ccg gat gtg att ggc ctg      96
Gln Leu Glu Ala Ile Val Glu Lys His Gln Pro Asp Val Ile Gly Leu
                20                  25                  30 cag gag aca aaa gtt cat gac gat atg ttt ccg ctc gaa gag gtg gcg    144
Gln Glu Thr Lys Val His Asp Asp Met Phe Pro Leu Glu Glu Val Ala
            35                  40                  45 aag ctc ggc tac aac gtg ttt tat cac ggg cag aaa ggc cat tat ggc    192
Lys Leu Gly Tyr Asn Val Phe Tyr His Gly Gln Lys Gly His Tyr Gly
        50                  55                  60 gtg gcg ctg ctg acc aaa gag acg ccg att gcc gtg cgt cgc ggc ttt    240
Val Ala Leu Leu Thr Lys Glu Thr Pro Ile Ala Val Arg Arg Gly Phe
65                  70                  75                  80 ccc ggt gac gac gaa gag gcg cag cgg cgg att att atg gcg gaa atc    288
Pro Gly Asp Asp Glu Glu Ala Gln Arg Arg Ile Ile Met Ala Glu Ile
                85                  90                  95 ccc tca ctg ctg ggt aat gtc acc gtg atc aac ggt tac ttc ccg cag    336
Pro Ser Leu Leu Gly Asn Val Thr Val Ile Asn Gly Tyr Phe Pro Gln
                100                 105                 110 ggt gaa agc cgc gac cat ccg ata aaa ttc ccg gca aaa gcg cag ttt    384
Gly Glu Ser Arg Asp His Pro Ile Lys Phe Pro Ala Lys Ala Gln Phe
            115                 120                 125 tat cag aat ctg caa aac tac ctg gaa acc gaa ctc aaa cgt gat aat    432
Tyr Gln Asn Leu Gln Asn Tyr Leu Glu Thr Glu Leu Lys Arg Asp Asn
        130                 135                 140 ccg gta ctg att atg ggc gat atg aat atc agc cct aca gat ctg gat    480
Pro Val Leu Ile Met Gly Asp Met Asn Ile Ser Pro Thr Asp Leu Asp
145                 150                 155                 160 atc ggc att ggc gaa gaa aac cgt aag cgc tgg ctg cgt acc ggt aaa    528
Ile Gly Ile Gly Glu Glu Asn Arg Lys Arg Trp Leu Arg Thr Gly Lys
                165                 170                 175 tgc tct ttc ctg ccg gaa gag cgc gaa tgg atg gac agg ctg atg agc    576
Cys Ser Phe Leu Pro Glu Glu Arg Glu Trp Met Asp Arg Leu Met Ser
                180                 185                 190 tgg ggg ttg gtc gat acc ttc cgc cat gcg aat ccg caa aca gca gat    624
Trp Gly Leu Val Asp Thr Phe Arg His Ala Asn Pro Gln Thr Ala Asp
            195                 200                 205 cgt ttc tca tgg ttt gat tac cgc tca aaa ggt ttt gac gat aac cgt    672
Arg Phe Ser Trp Phe Asp Tyr Arg Ser Lys Gly Phe Asp Asp Asn Arg
        210                 215                 220 ggt ctg cgc atc gac ctg ctg ctc gcc agc caa ccg ctg gca gaa tgt    720
Gly Leu Arg Ile Asp Leu Leu Leu Ala Ser Gln Pro Leu Ala Glu Cys
225                 230                 235                 240 tgc gta gaa acc ggc atc gac tat gaa atc cgc agc atg gaa aaa ccg    768
Cys Val Glu Thr Gly Ile Asp Tyr Glu Ile Arg Ser Met Glu Lys Pro
                245                 250                 255
```

```
tcc gat cac gcc ccc gtc tgg gcg acc ttc cgc cgc           804
Ser Asp His Ala Pro Val Trp Ala Thr Phe Arg Arg
        260                 265
```

<210> SEQ ID NO 16
<211> LENGTH: 268
<212> TYPE: PRT
<213> ORGANISM: E. coli

<400> SEQUENCE: 16

```
Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

<210> SEQ ID NO 17
<211> LENGTH: 1425
<212> TYPE: DNA
<213> ORGANISM: E. coli
<220> FEATURE:
<221> NAME/KEY: CDS
<222> LOCATION: (1)..(1425)

<400> SEQUENCE: 17

```
atg atg aat gac ggt aag caa caa tct acc ttt ttg ttt cac gat tac    48
Met Met Asn Asp Gly Lys Gln Gln Ser Thr Phe Leu Phe His Asp Tyr
1               5                   10                  15 gaa acc ttt ggc acg cac ccc gcg tta gat cgc cct gca cag ttc gca    96
Glu Thr Phe Gly Thr His Pro Ala Leu Asp Arg Pro Ala Gln Phe Ala
```

```
                Glu Thr Phe Gly Thr His Pro Ala Leu Asp Arg Pro Ala Gln Phe Ala
                            20                  25                  30 gcc att cgc acc gat agc gaa ttc aat gtc atc ggc gaa ccc gaa gtc        144
Ala Ile Arg Thr Asp Ser Glu Phe Asn Val Ile Gly Glu Pro Glu Val
            35                  40                  45 ttt tac tgc aag ccc gct gat gac tat tta ccc cag cca gga gcc gta        192
Phe Tyr Cys Lys Pro Ala Asp Asp Tyr Leu Pro Gln Pro Gly Ala Val
 50                  55                  60 tta att acc ggt att acc ccg cag gaa gca cgg gcg aaa gga gaa aac        240
Leu Ile Thr Gly Ile Thr Pro Gln Glu Ala Arg Ala Lys Gly Glu Asn
 65                  70                  75                  80 gaa gcc gcg ttt gcc gcc cgt att cac tcg ctt ttt acc gta ccg aag        288
Glu Ala Ala Phe Ala Ala Arg Ile His Ser Leu Phe Thr Val Pro Lys
                85                  90                  95 acc tgt att ctg ggc tac aac aat gtg cgt ttc gac gac gaa gtc aca        336
Thr Cys Ile Leu Gly Tyr Asn Asn Val Arg Phe Asp Asp Glu Val Thr
            100                 105                 110 cgc aac att ttt tat cgt aat ttc tac gat cct tac gcc tgg agc tgg        384
Arg Asn Ile Phe Tyr Arg Asn Phe Tyr Asp Pro Tyr Ala Trp Ser Trp
            115                 120                 125 cag cat gat aac tcg cgc tgg gat tta ctg gat gtt atg cgt gcc tgt        432
Gln His Asp Asn Ser Arg Trp Asp Leu Leu Asp Val Met Arg Ala Cys
        130                 135                 140 tat gcc ctg cgc ccg gaa gga ata aac tgg cct gaa aat gat gac ggt        480
Tyr Ala Leu Arg Pro Glu Gly Ile Asn Trp Pro Glu Asn Asp Asp Gly
145                 150                 155                 160 cta ccg agc ttt cgc ctt gag cat tta acc aaa gcg aat ggt att gaa        528
Leu Pro Ser Phe Arg Leu Glu His Leu Thr Lys Ala Asn Gly Ile Glu
                165                 170                 175 cat agc aac gcc cac gat gcg atg gct gat gtg tac gcc act att gcg        576
His Ser Asn Ala His Asp Ala Met Ala Asp Val Tyr Ala Thr Ile Ala
            180                 185                 190 atg gca aag ctg gta aaa acg cgt cag cca cgc ctg ttt gat tat ctc        624
Met Ala Lys Leu Val Lys Thr Arg Gln Pro Arg Leu Phe Asp Tyr Leu
            195                 200                 205 ttt acc cat cgt aat aaa cac aaa ctg atg gcg ttg att gat gtt ccg        672
Phe Thr His Arg Asn Lys His Lys Leu Met Ala Leu Ile Asp Val Pro
        210                 215                 220 cag atg aaa ccc ctg gtg cac gtt tcc gga atg ttt gga gca tgg cgc        720
Gln Met Lys Pro Leu Val His Val Ser Gly Met Phe Gly Ala Trp Arg
225                 230                 235                 240 ggc aat acc agc tgg gtg gca ccg ctg gcg tgg cat cct gaa aat cgc        768
Gly Asn Thr Ser Trp Val Ala Pro Leu Ala Trp His Pro Glu Asn Arg
                245                 250                 255 aat gcc gta att atg gtg gat ttg gca gga gac att tcg cca tta ctg        816
Asn Ala Val Ile Met Val Asp Leu Ala Gly Asp Ile Ser Pro Leu Leu
            260                 265                 270 gaa ctg gat agc gac aca ttg cgc gag cgt tta tat acc gca aaa acc        864
Glu Leu Asp Ser Asp Thr Leu Arg Glu Arg Leu Tyr Thr Ala Lys Thr
        275                 280                 285 gat ctt ggc gat aac gcc gcc gtt ccg gtt aag ctg gtg cat atc aat        912
Asp Leu Gly Asp Asn Ala Ala Val Pro Val Lys Leu Val His Ile Asn
        290                 295                 300 aaa tgt ccg gtg ctg gcc cag gcg aat acg cta cgc ccg gaa gat gcc        960
Lys Cys Pro Val Leu Ala Gln Ala Asn Thr Leu Arg Pro Glu Asp Ala
305                 310                 315                 320 gac cga ctg gga att aat cgt cag cat tgc ctc gat aac ctg aaa att       1008
Asp Arg Leu Gly Ile Asn Arg Gln His Cys Leu Asp Asn Leu Lys Ile
                325                 330                 335
```

```
ctg cgt gaa aat ccg caa gtg cgc gaa aaa gtg gtg gcg ata ttc gcg   1056
Leu Arg Glu Asn Pro Gln Val Arg Glu Lys Val Val Ala Ile Phe Ala
        340                 345                 350 gaa gcc gaa ccg ttt acg cct tca gat aac gtg gat gca cag ctt tat   1104
Glu Ala Glu Pro Phe Thr Pro Ser Asp Asn Val Asp Ala Gln Leu Tyr
    355                 360                 365 aac ggc ttt ttc agt gac gca gat cgt gca gca atg aaa att gtg ctg   1152
Asn Gly Phe Phe Ser Asp Ala Asp Arg Ala Ala Met Lys Ile Val Leu
370                 375                 380 gaa acc gag ccg cgt aat tta ccg gca ctg gat atc act ttt gtt gat   1200
Glu Thr Glu Pro Arg Asn Leu Pro Ala Leu Asp Ile Thr Phe Val Asp
385                 390                 395                 400 aaa cgg att gaa aag ctg ttg ttc aat tat cgg gca cgc aac ttc ccg   1248
Lys Arg Ile Glu Lys Leu Leu Phe Asn Tyr Arg Ala Arg Asn Phe Pro
            405                 410                 415 ggg acg ctg gat tat gcc gag cag caa cgc tgg ctg gag cac cgt cgc   1296
Gly Thr Leu Asp Tyr Ala Glu Gln Gln Arg Trp Leu Glu His Arg Arg
        420                 425                 430 cag gtc ttc acg cca gag ttt ttg cag ggt tat gct gat gaa ttg cag   1344
Gln Val Phe Thr Pro Glu Phe Leu Gln Gly Tyr Ala Asp Glu Leu Gln
        435                 440                 445 atg ctg gta caa caa tat gcc gat gac aaa gag aaa gtg gcg ctg tta   1392
Met Leu Val Gln Gln Tyr Ala Asp Asp Lys Glu Lys Val Ala Leu Leu
450                 455                 460 aaa gca ctt tgg cag tac gcg gaa gag att gtc                       1425
Lys Ala Leu Trp Gln Tyr Ala Glu Glu Ile Val
465                 470                 475

<210> SEQ ID NO 18
<211> LENGTH: 475
<212> TYPE: PRT
<213> ORGANISM: E. coli

<400> SEQUENCE: 18

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190
```

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val
465                 470                 475

<210> SEQ ID NO 19
<211> LENGTH: 738
<212> TYPE: DNA
<213> ORGANISM: Bacteriophage sp.
<220> FEATURE:
<221> NAME/KEY: CDS
<222> LOCATION: (31)..(708)

<400> SEQUENCE: 19
tccggaagcg gctctggtag tggttctggc atg aca ccg gac att atc ctg cag      54
                                 Met Thr Pro Asp Ile Ile Leu Gln
                                   1               5 cgt acc ggg atc gat gtg aga gct gtc gaa cag ggg gat gat gcg tgg     102
Arg Thr Gly Ile Asp Val Arg Ala Val Glu Gln Gly Asp Asp Ala Trp
         10                  15                  20 cac aaa tta cgg ctc ggc gtc atc acc gct tca gaa gtt cac aac gtg     150
His Lys Leu Arg Leu Gly Val Ile Thr Ala Ser Glu Val His Asn Val
 25                  30                  35                  40 ata gca aaa ccc cgc tcc gga aag aag tgg cct gac atg aaa atg tcc     198

```
              Ile Ala Lys Pro Arg Ser Gly Lys Lys Trp Pro Asp Met Lys Met Ser
                          45                  50                  55 tac ttc cac acc ctg ctt gct gag gtt tgc acc ggt gtg gct ccg gaa        246
Tyr Phe His Thr Leu Leu Ala Glu Val Cys Thr Gly Val Ala Pro Glu
                60                  65                  70 gtt aac gct aaa gca ctg gcc tgg gga aaa cag tac gag aac gac gcc        294
Val Asn Ala Lys Ala Leu Ala Trp Gly Lys Gln Tyr Glu Asn Asp Ala
            75                  80                  85 aga acc ctg ttt gaa ttc act tcc ggc gtg aat gtt act gaa tcc ccg        342
Arg Thr Leu Phe Glu Phe Thr Ser Gly Val Asn Val Thr Glu Ser Pro
        90                  95                  100 atc atc tat cgc gac gaa agt atg cgt acc gcc tgc tct ccc gat ggt        390
Ile Ile Tyr Arg Asp Glu Ser Met Arg Thr Ala Cys Ser Pro Asp Gly
    105                 110                 115                 120 tta tgc agt gac ggc aac ggc ctt gaa ctg aaa tgc ccg ttt acc tcc        438
Leu Cys Ser Asp Gly Asn Gly Leu Glu Leu Lys Cys Pro Phe Thr Ser
                125                 130                 135 cgg gat ttc atg aag ttc cgg ctc ggt ggt ttc gag gcc ata aag tca        486
Arg Asp Phe Met Lys Phe Arg Leu Gly Gly Phe Glu Ala Ile Lys Ser
            140                 145                 150 gct tac atg gcc cag gtg cag tac agc atg tgg gtg acg cga aaa aat        534
Ala Tyr Met Ala Gln Val Gln Tyr Ser Met Trp Val Thr Arg Lys Asn
        155                 160                 165 gcc tgg tac ttt gcc aac tat gac ccg cgt atg aag cgt gaa ggc ctg        582
Ala Trp Tyr Phe Ala Asn Tyr Asp Pro Arg Met Lys Arg Glu Gly Leu
    170                 175                 180 cat tat gtc gtg att gag cgg gat gaa aag tac atg gcg agt ttt gac        630
His Tyr Val Val Ile Glu Arg Asp Glu Lys Tyr Met Ala Ser Phe Asp
185                 190                 195                 200 gag atc gtg ccg gag ttc atc gaa aaa atg gac gag gca ctg gct gaa        678
Glu Ile Val Pro Glu Phe Ile Glu Lys Met Asp Glu Ala Leu Ala Glu
                205                 210                 215 att ggt ttt gta ttt ggg gag caa tgg cga tctggctctg gttccggcag         728
Ile Gly Phe Val Phe Gly Glu Gln Trp Arg
            220                 225 cggttccgga                                                             738

<210> SEQ ID NO 20
<211> LENGTH: 226
<212> TYPE: PRT
<213> ORGANISM: Bacteriophage sp.

<400> SEQUENCE: 20

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
                20                  25                  30

Thr Ala Ser Glu Val His Asn Val Ile Ala Lys Pro Arg Ser Gly Lys
            35                  40                  45

Lys Trp Pro Asp Met Lys Met Ser Tyr Phe His Thr Leu Leu Ala Glu
        50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
                100                 105                 110

Arg Thr Ala Cys Ser Pro Asp Gly Leu Cys Ser Asp Gly Asn Gly Leu
```

```
                 115                 120                 125
Glu Leu Lys Cys Pro Phe Thr Ser Arg Asp Phe Met Lys Phe Arg Leu
        130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
        210                 215                 220

Trp Arg
225
```